US005977386A

United States Patent [19]
Staab et al.

[11] Patent Number: 5,977,386
[45] Date of Patent: Nov. 2, 1999

[54] 6-THIO-SUBSTITUTED PACLITAXELS

[75] Inventors: Andrew J. Staab, Middletown; John F. Kadow, Wallingford; Dolatrai M. Vyas, Madison; Mark D. Wittman, Cheshire; Harold A. Mastalerz, Guilford, all of Conn.

[73] Assignee: Bristol-Myers Squibb Company, Princeton, N.J.

[21] Appl. No.: 08/979,139

[22] Filed: Nov. 26, 1997

Related U.S. Application Data

[60] Provisional application No. 60/036,351, Jan. 23, 1997, and provisional application No. 60/033,419, Dec. 24, 1996.

[51] Int. Cl.$^6$ .......................... C07D 305/14; A61K 31/38
[52] U.S. Cl. .......................... 549/510; 514/449; 514/438; 514/444; 549/59; 549/60; 549/510; 549/511
[58] Field of Search ...................... 549/510, 60; 514/449, 514/444

[56]     References Cited

U.S. PATENT DOCUMENTS

| | | | |
|---|---|---|---|
| 4,814,470 | 3/1989 | Colin et al. | 514/449 |
| 4,876,399 | 10/1989 | Holton et al. | 568/817 |
| 4,960,790 | 10/1990 | Stella et al. | 549/540 |
| 5,254,580 | 10/1993 | Chen et al. | 514/449 |
| 5,272,171 | 12/1993 | Ueda et al. | 514/449 |
| 5,294,637 | 3/1994 | Chen et al. | 514/449 |
| 5,352,806 | 10/1994 | Gunawardana et al. | 549/510 |
| 5,714,512 | 2/1998 | Bastart et al. | 514/449 |

FOREIGN PATENT DOCUMENTS

| | | |
|---|---|---|
| 600517A1 | 6/1994 | European Pat. Off. . |
| 0604910A1 | 7/1994 | European Pat. Off. . |
| 617034A1 | 9/1994 | European Pat. Off. . |
| 764643A1 | 3/1997 | European Pat. Off. . |
| WO93/06093 | 4/1993 | WIPO . |
| WO94/08984 | 4/1994 | WIPO . |
| WO94/14787 | 7/1994 | WIPO . |
| WO94/20485 | 9/1994 | WIPO . |
| WO94/29288 | 12/1994 | WIPO . |
| WO96/00724 | 1/1996 | WIPO . |
| WO96/03394 | 2/1996 | WIPO . |

OTHER PUBLICATIONS

Physian's Desk Reference, 49th Edition, Medical Economics, p. 682, 1995.
T.L. Riss et al., Mol. Biol. Cell 3 (supp.), 184a, 1992.
Hester et al., (CA 121: 280920, WO 9413655).
E. K. Rowinsky and R. C. Donehower, "The Clinical Pharmacology and Use of Antimicrotubule Agents in Cancer Chemotherapeutics," Pharmac. Ther., 52: 35–84, 1991.
C. M. Spencer and D. Faulds, "Paclitaxel, A Review of its Pharmacodynamic and Pharmacokinetic Properties and Therapeutic Potential in the Treatment of Cancer," Drugs, 48(5), 794–847, 1994.
K.C. Nicolaou, et al, "Chemistry and Biology of Taxol," Angew. Chem., Int. Ed. Engl., 33: 15–44, 1994.
Greene and Wuts, Protective Groups in Organic Synthesis, 2nd Ed., John Wiley & Sons, and McOmie, 1991.

S.–H. Chen, et al, "First Syntheses of Novel Paclitaxel (Taxol) Analogs Modified at the C4–Position," J. Org. Chem., 59, pp. 6156–6158, 1994.
S.–H. Chen, et al, "Structure–Activity Relationships of Taxol: Synthesis and Biological Evaluation of C2 Taxol Analogs," Bioorganic and Medicinal Chemistry Letters, vol. 4, No. 3, pp. 479–482, 1994.
R.A. Johnson, "Taxol Chemistry. 7–O–Triflates as Precursors to Olefins and Cyclopropanes," Tetrahedron Letters, vol. 35, No. 43, pp. 7893–7896, 1994.
X. Liang and G.I. Kingston, "Synthesis and Biological Evaluation of Paclitaxel Analogs Modified in Ring C," Tetrahedron Letters, vol. 36, No. 17, pp. 2901–2904, 1995.
G. Roth, et al, "Reaction of Paclitaxel and 10–Desacetyl Baccatin III with Diethylamino Sulfurtrifluoride," Tetrahedron Letters, vol. 36, No. 10, pp. 1609–1612, 1995.
S.–H. Chen, et al, "The Chemistry of Taxanes: Reaction of Taxol and Baccatin Derivatives with Lewis Acids in Aprotic and Protic Media," Tetrahedron, vol. 49, No. 14, pp. 2805–2828, 1993.
L.L. Klein, "Synthesis of 9–Dihydrotaxol: A Novel Bioactive Taxane," Tetrahedron Letters, vol. 34, No. 13, pp. 2047–2050, 1993.
J. Kant, et al, "A Chemoselective Approach to Functionalize the C–10 Position of 10–Deacetylbaccatin III. Synthesis and Biological Properties of Novel C–10 Taxel Analogues," Tetrahedron Letters, 35, No. 31, pp. 5543–5546, 1994.
S.G. Arbuck, et al, Taxol® Science and Applications, edited by M. Suffness, 1995 (CRC Press Inc., Boca Raton, Florida), pp. 379–415.
K. C. Nicolaou, et al, "Chemical Synthesis and Biological Evaluation of C–2 Taxoids," J. Am. Chem. Soc., 117, pp. 2409–2420, 1995.
K. V. Rao, et al, "Synthesis and Evaluation of Some 10–Mono– and 2',10–Diesters of 10–Deacetylpaclitaxel," J. Med. Chem., 38, pp. 3411–3414, 1995.
G. I. Georg, et al, "Stereoselective Synthesis of 9β–Hydroxytaxanes Via Reduction With Samarium Diiodide," Tetrahedron Letters, 36(11), pp. 1783–1786, 1995.
F.A. Holmes, et al, Taxane Anticancer Agents Basic Science and Current Status, edited by G.I. Georg, et al, 1995, American Chemical Society, Washington, D.C. 31–57.
X. Liang, et al, "Synthesis, Structure Elucidation and Biological Evaluation of C–Norpaclitaxel," Tetrahedron Letters, 36(43), pp. 7795–7798, 1995.
J. W. Wilt, et al, "Absolute Rate Constants for Some Intermolecular and Intramolecular Reactions of a α–, β–, and γ–Silicon–Sutstituted Radicals," J. Am. Chem. Soc., 110, pp. 281–287, 1988.

(List continued on next page.)

*Primary Examiner*—Jose' G. Dees
*Assistant Examiner*—Sabiha N. Qazi
*Attorney, Agent, or Firm*—Samuel J. DuBoff

[57]     ABSTRACT

The present invention concerns novel paclitaxel derivatives, their use as antitumor agents, and pharmaceutical formulations.

10 Claims, No Drawings

OTHER PUBLICATIONS

F. K. Brown, et al, "Matrix Metalloproteinase Inhibitors Containing a (Carboxyalkyl)Amino Zinc Ligand: Modification of the P1 and P2' Residues," J. Med. Chem., 37, p. 674–688, 1994.

W. Rose, "Evaluation of Madison 109 Lung Carcinoma as a Model for Screening Antitumor Drugs," Cancer Treatment Reports, 65, No. 3–4, pp. 299–312, 1981.

W. Rose, "Evaluation of Platinol Analogs Using the M5076 Murine Sarcoma," Anticancer Res., 6, pp. 557–562, 1986.

W. Rose, et al, "In Vivo Model Development of Cisplatin–Resistant and Sensitive A2780 Human Ovarian Carcinomas," In–Vivo, 4, pp. 391–396, 1990.

6-THIO-SUBSTITUTED PACLITAXELS

This application claims the benefit of U.S. Provisional Application No. 60/036,351 filed Jan. 23, 1997 and Ser. No. 60/033,419 filed Dec. 24, 1996.

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the bark of Pacific yew trees, *Taxus brevifolia*. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," *Pharmac. Ther.*, 52:35–84, 1991; by Spencer and Faulds in "Paclitaxel, A Review of its Pharmacodynamic and Pharmacokinetic Properties and Therapeutic Potential in the Treatment of Cancer," *Drugs*, 48 (5) 794–847, 1994; by K. C. Nicolaou et al. in "Chemistry and Biology of Taxol," *Angew. Chem., Int. Ed. Engl.*, 33:15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also been found to have good antitumor activity. The structures of paclitaxel and Taxotere® are shown below along with the conventional numbering system for molecules belonging to the class; such numbering system is also employed in this application.

Taxol®: R=Ph; R'=acetyl
Taxotere®: R=t-butoxy; R'=hydrogen

SUMMARY OF THE INVENTION

This invention describes novel antitumor compounds in which the C-6 position of the taxane core is linked by a direct bond to a sulfur atom. This invention relates to novel antitumor compounds represented by formula I, or pharmaceutically acceptable salts thereof A compound of formula I, or a pharmaceutically acceptable salt thereof wherein:

R is aryl, substituted aryl, $C_{1-6}$ alkyl, $C_{2-6}$ alkenyl, $C_{3-6}$ cycloalkyl, or heteroaryl;

$R^A$ is hydrogen;

$R^B$ is —NHC(O)-aryl, —NHC(O)-substituted aryl, —NHC(O)-heteroaryl, —NHC(O)OCH$_2$Ph, —NHC(O)O—($C_{1-6}$ alkyl), or —NHC(O)O—($C_{3-6}$ cycloalkyl);

$R^C$ is hydrogen;

$R^D$ is hydroxy, —OC(O)R$^X$, —OC(O)OR$^X$, OP(O)(OH)$_2$, OCH$_2$OP(O)(OH)$_2$, —OCH$_2$OCH$_2$OP(=O)(OH)$_2$, OP(O)(OH)$_2$ base, OCH$_2$OP(O)(OH)$_2$ base, —OCH$_2$OCH$_2$OP(=O)(OH)$_2$ base, —(OCH$_2$)$_m$OC=OCH$_2$NHR$^X$, —(OCH$_2$)$_m$OC(=O)CH(R") NR'$_6$R'$_7$, —OCOCH$_2$CH$_2$NH$_3$$^+$HCOO$^-$, —OCOCH$_2$CH$_2$COOH, —OCO(CH$_2$)$_3$COOH, —OC(O)(CH$_2$)$_a$NR$^F$R$^G$, where a is 0–3, —OC(O)CH$_2$CH$_2$C(O)OCH$_2$CH$_2$OH or —OC(O)—Z—C(O)—R';

Z is —CH$_2$CH$_2$—, —CH$_2$CH$_2$CH$_2$—, —CH=CH—, 1,2-cyclohexane or 1,2-phenylene;

R' is —OH, —OH base, —NR'$_2$R'$_3$, —OR'$_3$, —SR'$_3$, or —OCH$_2$C(O)NR'$_4$R'$_5$;

R'$_2$ is —H or —CH$_3$;

R'$_3$ is —(CH$_2$)$_j$NR'$_6$R'$_7$ or (CH$_2$)$_n$N$^+$R'$_6$R'$_7$R'$_8$X$^-$, where j is 1–3;

R'$_4$ is —H or —C$_1$–C$_4$ alkyl;

R'$_5$ is —H, —C$_1$–C$_4$ alkyl, benzyl, hydroxyethyl, —CH$_2$CO$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X$^-$ is halide;

base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH;

R$^F$ and R$^G$ are independently —H or —C$_1$–C$_3$ alkyl, or R$^F$ and R$^G$ taken together with the nitrogen of NR$^F$R$^G$ form a pyrrolidino, piperidino, morpholino or N-methylpiperizino groups;

R" is —H, —CH$_3$, —CH$_2$CH(CH$_3$)$_2$, —CH(CH$_3$) CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O)

NHCH$_2$CH$_2$SO$_3$—Y+ or —OC(O)CH$_2$CH$_2$C(O)NHCH$_2$CH$_2$CH$_2$SO$_3$—Y+;

Y+ is Na+ or N+(Bu)$_4$;

R$^2$ is phenyl or substituted phenyl;

R$^4$ is C$_{1-4}$ alkyl, C$_{3-5}$ cycloalkyl or —O—(C$_1$–C$_4$ alkyl);

L is O or S;

R$^6$ and R$^{6'}$ are independently hydrogen, —SH, —S-[C$_{1-6}$ alkyl(OH)$_m$], —S-ethenyl, —S-substituted ethenyl, —S(O)$_n$CH$_2$CN, —S(O)$_n$CH$_2$C(O)Q, —SCH$_2$ halogen, —SC(O)-[C$_{1-6}$ alkyl(OH)$_m$], —SC(O)O(C$_1$–C$_6$ alkyl), —SC(O)N(W)$_2$, —SC(S)—(C$_1$–C$_6$ alkyl), —SC(S)O(C$_1$–C$_6$ alkyl), —SC(S)N(W)$_2$, —S(O)$_n$-[C$_{1-6}$ alkyl(OH)$_m$], —S(C$_1$–C$_6$ alkyl)$_2$$^+$X$^-$, —S(O)$_2$OH, —S(O)$_2$NH[C$_{1-6}$ alkyl(OH)$_m$], —S(O)$_2$N[C$_{1-6}$ alkyl(OH)$_m$]$_2$, —S—S-[C$_{1-6}$ alkyl(OH)$_m$], —S—S-substituted phenyl, —S(O)—CN, —S(O)$_2$—CN, —SCH$_2$O[C$_{1-6}$ alkyl(OH)$_m$], —SCH(C$_1$–C$_6$ alkyl)O[C$_{1-6}$ alkyl(OH)$_m$], —SCH$_2$OCH$_2$OCH$_3$, —SCH$_2$S[C$_{1-6}$ alkyl(OH)$_m$], —SCH$_2$S(O)[C$_{1-6}$ alkyl(OH)$_m$], —SCH$_2$S(O)$_2$[C$_{1-6}$ alkyl(OH)$_m$], —S-heteroaryl or —SCN;

m is 0, 1, 2 or 3;

n is 0, 1, or 2;

S-substituted ethenyl is —S—C(R$^H$)=C(R$^J$)(R$^K$), wherein two of R$^H$, R$^J$ and R$^K$ are each H and the other of R$^H$, R$^J$ and R$^K$ is C$_{1-3}$ alkyl, CN, COOC$_{1-3}$ alkyl, S(O)$_2$CH$_3$ or C(O)CH$_3$;

W is H or C$_{1-6}$ alkyl;

Q is -[C$_{1-6}$ alkyl(OH)$_m$], —O(C$_{1-6}$ alkyl), —OCH$_2$CCl$_3$, —N(W)$_2$ or —C(O)OH;

R$^{7'}$ is hydrogen;

R$^7$ is hydrogen, hydroxy or when taken together with R$^{19}$ forms a cyclopropane ring;

R$^9$ and R$^{9'}$ are independently hydrogen or hydroxy or R$^9$ and R$^{9'}$ together form an oxo (keto) group;

R$^{10}$ is hydrogen, hydroxy or —OC(O)—(C$_1$–C$_6$ alkyl);

R$^{10'}$ is hydrogen;

R$^{14}$ is hydrogen or hydroxy; and

R$^{19}$ is methyl or when taken together with R$^7$ forms a cyclopropane ring.

A preferred embodiment are compounds with the structure I or pharmaceutically acceptable salts thereof wherein:

R is phenyl, p-fluorophenyl, p-chlorophenyl, p-hydroxyphenyl, p-tolyl, isopropyl, isopropenyl, isobutenyl, isobutyl, cyclopropyl, furyl, or thienyl;

R$^2$ is phenyl;

L is O;

R$^{6'}$ is hydrogen;

R$^6$ is —SH, —S-[C$_{1-6}$ alkyl(OH)$_m$], —S-ethenyl, —S-substituted ethenyl, —S(O)$_n$CH$_2$CN, —S(O)$_n$CH$_2$C(O)Q, —SCH$_2$ halogen, —SC(O)-[C$_{1-6}$ alkyl(OH)$_m$], —SC(O)O(C$_1$–C$_6$ alkyl), —SC(O)N(W)$_2$, —SC(S)—(C$_1$–C$_6$ alkyl), —SC(S)O(C$_1$14 C$_6$ alkyl), —SC(S)N(W)$_2$, —S(O)$_n$-[C$_{1-6}$ alkyl(OH)$_m$], —S(C$_1$–C$_6$ alkyl)$_2$$^+$X$^-$, —S(O)$_2$OH, —S(O)$_2$NH[C$_{1-6}$ alkyl(OH)$_m$], —S(O)$_2$N[C$_{1-6}$ alkyl(OH)$_m$]$_2$, —S—S-[C$_{1-6}$ alkyl(OH)$_m$], —S—S-substituted phenyl, —S(O)—CN, —S(O)$_2$—CN, —SCH$_2$O[C$_{1-6}$ alkyl(OH)$_m$], —SCH(C$_1$–C$_6$ alkyl)O[C$_{1-6}$ alkyl(OH)$_m$], —SCH$_2$OCH$_2$OCH$_3$, —SCH$_2$S[C$_{1-6}$ alkyl(OH)$_m$], —SCH$_2$S(O) [C$_{1-6}$ alkyl(OH)$_m$], —SCH$_2$S(O)$_2$[C$_{1-6}$ alkyl(OH)$_m$], —S-heteroaryl or —SCN;

m is 0, 1, 2 or 3;

n is 0, 1, or 2;

W is H or C$_{1-6}$ alkyl;

R$^9$ and R$^{9'}$ together form an oxo (keto) group;

R$^{10}$ is hydroxy or —OC(O)CH$_3$; and

R$^{14}$ is hydrogen.

Another preferred embodiment are compounds with the structure I or pharmaceutically acceptable salts thereof wherein:

R$^6$ is —SH, —S-[C$_{1-6}$ alkyl(OH)$_m$], —S(O)$_n$-[C$_{1-6}$ alkyl(OH)$_m$], —S-ethenyl, —S-substituted ethenyl, —SCH$_2$CN, —S(O)CH$_2$CN, —SCH$_2$C(O)Q, —SC(O)-[C$_{1-6}$ alkyl(OH)$_m$], —SCH$_2$O[C$_{1-6}$ alkyl(OH)$_m$], —SCH(C$_1$–C$_6$ alkyl)O[C$_{1-6}$ alkyl(OH)$_m$], —SCH$_2$OCH$_2$OCH$_3$, —SCH$_2$S[C$_{1-6}$ alkyl(OH)$_m$], —SCH$_2$S(O)[C$_{1-6}$ alkyl(OH)$_m$], —SCH$_2$S(O)$_2$[C$_{1-6}$ alkyl(OH)$_m$], or —SCN.

Another preferred embodiment are compounds with the structure I or pharmaceutically acceptable salts thereof wherein:

R$^B$ is —NHC(O)-Ph or —NHC(O)O—(C$_{1-6}$ alkyl);

R$^D$ is hydroxy;

R$^4$ is methyl;

R$^6$ is —S-[C$_{1-6}$ alkyl(OH)$_m$], —S-ethenyl, —S-substituted ethenyl, —SCH$_2$CN, —S(O)CH$_2$CN, —SCH$_2$C(O)Q, —S(O)(C$_{1-6}$ alkyl), —SC(O)-[C$_{1-6}$ alkyl(OH)$_m$], —SCH$_2$OCH$_3$, —SCH$_2$OCH$_2$OCH$_3$, —SCH$_2$S(C$_{1-6}$ alkyl), —SCH$_2$S(O)(C$_{1-6}$ alkyl), or —SCN; and R$^7$ is hydrogen or when taken together with R$^{19}$ forms a cyclopropane ring.

Another preferred embodiment are compounds with the structure I or pharmaceutically acceptable salts thereof wherein:

R$^7$ is hydrogen; and

R$^{19}$ is methyl.

Another preferred embodiment are compounds with structure I or pharmaceutically acceptable salts thereof wherein:

R is phenyl;

R$^6$ is —S-methyl, —S-ethyl, —S-ethenyl, —SCH$_2$CN, —S(O)CH$_2$CN, —SCH$_2$C(O)—(C$_{1-6}$ alkyl), —S(O)—(C$_{1-6}$ alkyl), —SC(O)-[C$_{1-6}$ alkyl(OH)$_m$], —SCH$_2$OCH$_3$, —SCH$_2$OCH$_2$OCH$_3$, —SCH$_2$SCH$_3$, —SCH$_2$S(O)(CH$_3$), or —SCN; and R$^{10}$ is —OC(O)CH$_3$.

Another preferred embodiment are compounds with structure I or pharmaceutically acceptable salts thereof wherein:

R is phenyl or substituted phenyl;

R$^A$ is hydrogen;

R$^B$ is —NHC(O)Ph or —NHC(O)O(C$_{1-6}$ alkyl);

R$^C$ is hydrogen;

R$^D$ is hydroxy;

R$^2$ is phenyl;

R$^4$ is methyl;

L is O;

R$^{6'}$ is hydrogen;

R$^6$ is —SH, —S(C$_{1-3}$ alkyl), —SCN, —S-ethenyl, —SCH$_2$CN, —SCH$_2$CH$_2$OH, —SCH$_2$(O)-[C$_{1-6}$ alkyl (OH)$_m$] or —S—(2-thienyl);

R$^{7'}$ and R$^7$ are each hydrogen;

$R^9$ and $R^{9'}$ together form an oxo (keto) group;

$R^{10}$ is —OC(O)CH$_3$ or OH;

$R^{10'}$ is hydrogen;

$R^{14}$ is hydrogen; and $R^{19}$ is methyl.

Another preferred embodiment are compounds with structure I or pharmaceutically acceptable salts thereof wherein:

R is phenyl, p-chlorophenyl, p-methylphenyl, p-fluorophenyl or p-hydroxyphenyl.

Another aspect of the present invention provides a method for inhibiting tumor in a mammalian host which comprises administering to said mammalian host an antitumor effective amount of any of the aforementioned compounds of formula I.

Yet, another aspect of the present invention provides a pharmaceutical formulation which comprises an antitumor effective amount of any of the aforementioned compounds of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group can contain. For example "C$_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "C$_{1-6}$ alkyl" can also refer to C$_{1-6}$ alkylene which bridges two groups; examples include propane-1,3-diyl, butane-1,4-diyl, 2-methyl-butane-1,4-diyl, etc. "C$_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "C$_{2-6}$ alkenyl" can also refer to C$_{2-6}$ alkenediyl which bridges two groups; examples include ethylene-1,2-diyl (vinylene), 2-methyl-2-butene-1,4-diyl, 2-hexene-1,6-diyl, etc. "C$_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl independently substituted with one to five (but preferably one to three) groups selected from C$_{1-6}$ alkanoyloxy, hydroxy, halogen, C$_{1-6}$ alkyl, trifluoromethyl, C$_{1-6}$ alkoxy, aryl, C$_{2-6}$ alkenyl, C$_{1-6}$ alkanoyl, nitro, amino, cyano, azido, C$_{1-6}$ alkylamino, di-C$_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press.

"Ph" means phenyl; "ipr" means isopropyl; "DAST" means diethylamino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

The term "taxane" or "taxane core" refers to moieties with a framework of the structure:

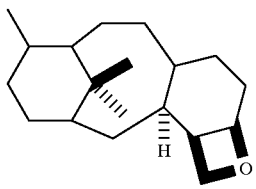

The cyclopropane group which can be constituted from R$^7$ and R$^{19}$ of formula I can alternatively be referred to as "7b,8b-methano" group as in Tetrahedron Letters, Vol 35, No 43, pp 7893–7896 (1994) or as "cyclopropa" group as in U.S. Pat. No. 5,254,580 issued Oct. 19, 1993.

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire.

Schemes I–XII, which depict processes that compounds within the scope of formula I can be made, are only shown for the purpose of illustration and are not to be construed as limiting the processes to make the compounds by any other methods.

The procedures for preparing taxane derivatives which contain a hydroxy group at C-6 and which are deoxygenated at C-7 are disclosed in our colleague's co-pending application Ser. No. 60/019,493 filed Jun. 6, 1996; the disclosure of which is herein incorporated by reference in its entirety. Schemes I and II illustrate the chemistry from this application which is utilized to synthesize 7-deoxy-6-alpha-hydroxy-paclitaxel analogs. Although the protecting group used to protect the 2' hydroxy group in the sidechain in this scheme is a trialkyl silyl ether, other protecting groups which are well known in the taxane art could be utilized.

The preparation of a diol intermediate is shown in Scheme I. The starting material is a taxane analog suitably protected to leave the most reactive hydroxy group at C-7. Compound 1 in Scheme I is protected at the 2' hydroxy group at the sidechain with a triethylsilyl ether. The preparation of intermediates such as 1 are now well known in the art. The synthesis of diol 4 utilizes precursor 6,7-olefin analogs 3 which is also now well known in the art. Compound 3 can be formed directly from intermediate's 1 upon treatment with a reagent such as DAST as described in the U.S. Pat. No. 5,380,751. The synthesis of olefin 3 described in Scheme I proceeds through the 7-trifluoromethanesulfonate (triflate) intermediates 2 which are prepared as shown in step A. Elimination of the triflate (step B) provides the desired olefins 3. The preparation of 7-O triflates and their conversion into cyclopropanes and olefins has been divulged by Johnson, R. A., et al., Taxol chemistry. 7-O-Triflates as precursors to olefins and cyclopropanes. *Tetrahedron Letters*, 1994. 35(43): p. 7893–7896 & by the same authors in WO 94/29288.

The olefin 3 is then hydroxylated with Osmium tetroxide (step C) which is used in either stoichiometric quantities or catalytically in the presence of a cooxidant such as N-methyl morpholine-N oxide (NMO). A patent application on such diol intermediates which includes some methods of its preparation has been published: Roth et. al. 6,7 EP 0 600 517 A1. A protected taxane diol intermediate has also been described in the literature by Liang et. al. *Tetrahedron Letters* 1995, 36(17) 2901–2904. and ibid. 1995, 36(43) 7795–7798. The osmium reagent only reacts from the face of the double bond which is down or alpha as the taxane core is depicted in this document. Thus this reaction provides only one stereoisomer.

The preferred approach to the initial 7-deoxy-substituted taxanes is shown in Scheme II. An advantage of this approach is it avoids the need for a selective protection of the starting 6,7 diol 4. A new cyclic thiocarbonate 5 is formed (step D) upon reaction with thiocarbonyldiimidazole (or alternatively thiophosgene could be used) under standard conditions of amine base and optional inert solvent. Other standard organic chemistry bases could also be utilized. Reduction of the thiocarbonate 5 (step E) with most preferably, a trialkyl germane such as tri-n-butyl germane provides the C-7 deoxy compound 6 with little, if any, competitive formation of the C-6 deoxy material. Alternatively, a trialkyl tin hydride could be utilized in place of the germanium reagent. The use of the tin hydride reagent also results in competitive deoxygenation at C-10 which produces mixtures which must be separated. The tin reagent is the method of choice for producing C 7 and 10 deoxy-6-substituted analogs if these are the desired targets. The use of trialkyl germane to suppress an unwanted side reaction is not precedented. This reagent has been studied by physical chemists in other radical reactions. J. W. Wilt et.al. *J. Am. Chem. Soc.* 1988,110, 281–287. The product of step E is a 7-deoxy-6-alpha-hydroxy intermediate 6 which is protected at the sidechain. The above reactions are demonstrated in Example 1.

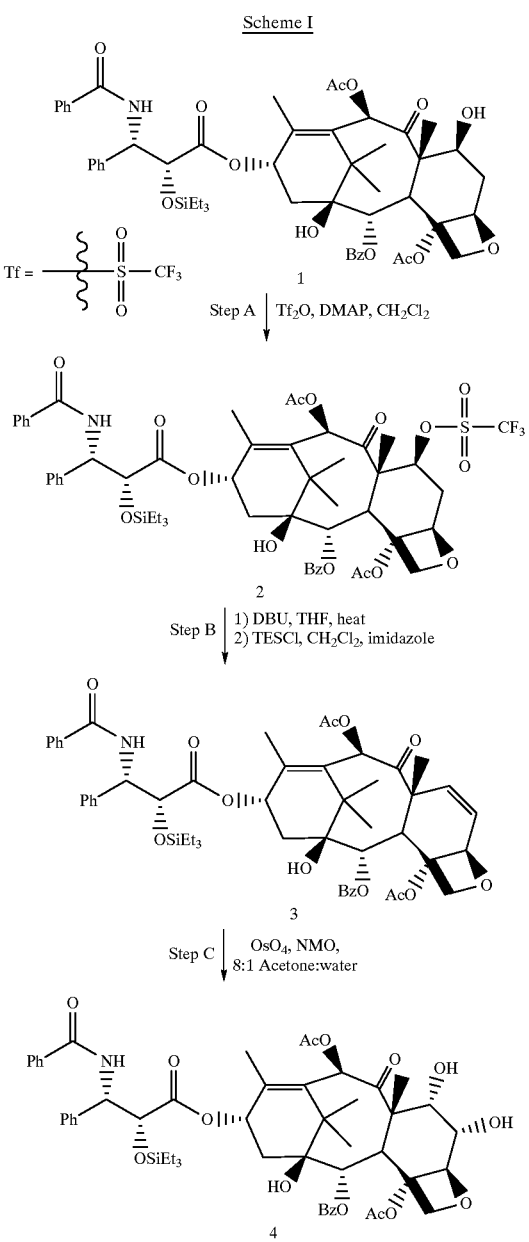

Scheme I

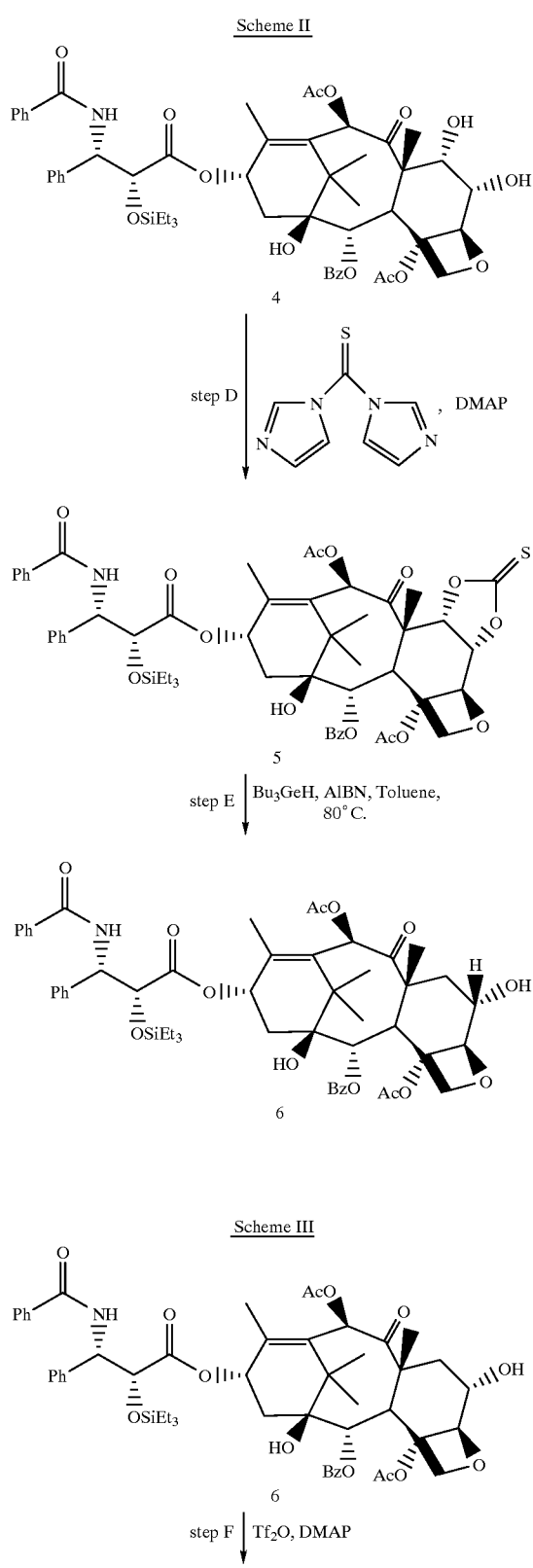

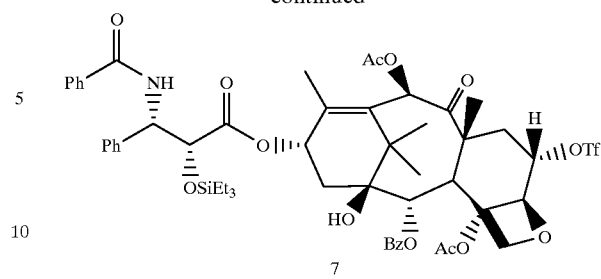

Scheme III illustrates the preparation of the C-6 trifluoromethanesulfonate (triflate or Tf) 7 from the C-6 hydroxy compound 6. The conversion is carried out as shown in Step f using Triflic anhydride and 4-N,N-Dimethylamino pyridine (DMAP) as a catalyst. Although other amine bases could be utilized, the conditions described in the experimental are preferred. While a number of nonprotic organic solvents can be utilized successfully for this reaction, the preferred solvent is dichloromethane.

Scheme IV, step G illustrates a direct displacement of the trifluromethanesulfonate of Compound 7 to produce the methyl sulfide 8. Lithium or potassium mercaptides could also be utilized. 15 Although a number of organic solvents such as DMSO, DMF, THF, dioxane or others could be utilized for this transformation, the preferred solvent is DMF. The mercaptide derived from methyl mercaptan is depicted in this scheme, but mercaptides derived from other alkyl and aromatic thiols can be used similarly. The products from this reaction can be purified using preparative HPLC or chromatography. Although the trifluoromethanesulfonate derivative is used in this reaction sequence, the corresponding p-tolylsulfonate or methanesulfonate derivatives could be used similarly.

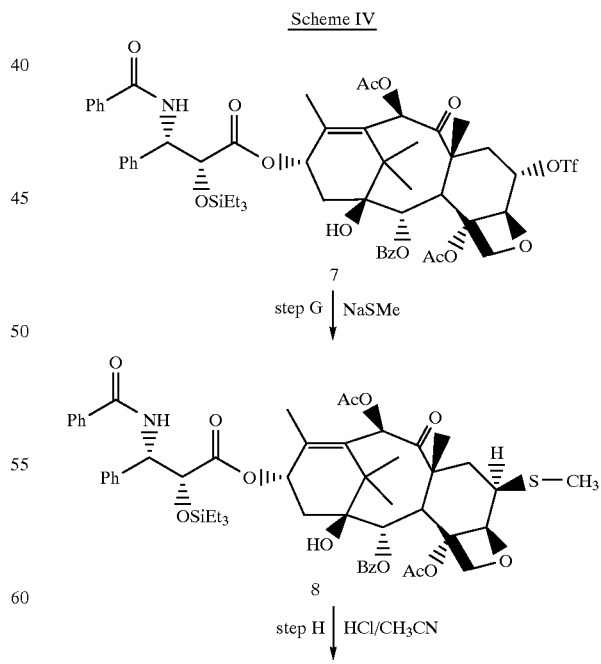

-continued

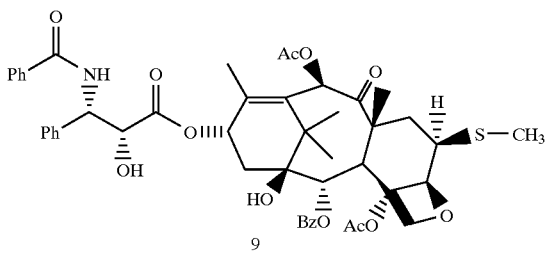

As shown in step H of Scheme 4, the 2' triethylsilyl protecting group present in sulfide 8 can be removed using aqueous HCl in acetonitrile to provide 9 which is a compound claimed in this invention. These are standard conditions for removing silyl protecting groups from taxanes and other standard conditions such as fluoride sources could also have been utilized.

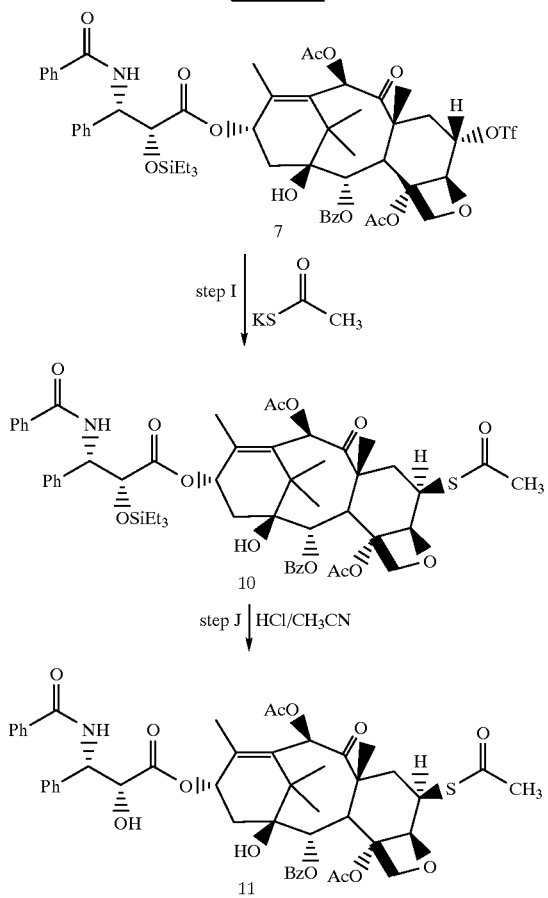

As shown in Scheme V, the triflate intermediate 7 reacts quite efficiently with the potassium salt of thioacetic acid in DMF to provide the thioester analog 10. The salts of other thio acids could be utilized similarly. Other solvents as discussed above can also be employed. An alternative synthesis of thioester 10 could be realized by reacting alcohol 6 with thioacetic acid in the presence of DEAD (diethyl azodicarboxylate) and triphenylphosphine. These and other variations of the Mitsunobu reaction (J. Med. Chem. 1994, 37, 674) could be employed. Step J describes the standard deprotection step to produce analog 11 which is a compound claimed in this patent and which has useful antitumor properties.

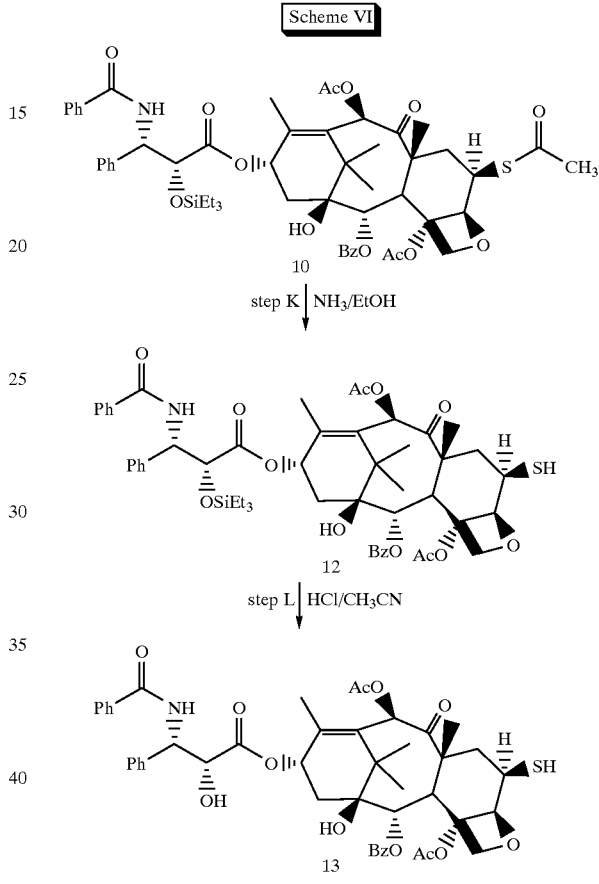

Scheme VI, step K depicts the ammonolysis of the thioester at position 6 of 10 to produce the C-6 mercaptan 12. Although other hydrolysis conditions such as aqueous base in the presence of an organic cosolvent can be utilized the depicted ammonolysis is the preferred method. As shown in step L, standard deprotection produces 13 which is a compound with useful antitumor properties.

Mercaptan intermediate 12 can be alkylated or acylated with typical electrophiles to produce new analogs. For example Scheme VII illustrates the formation of methyl sulfide 8 via alkylation (step M). Deprotection as already described in step H of Scheme IV produces sulfide 9. This is the preferred method for synthesizing methyl sulfide 9. Other thiol alkylation conditions which are well known in the art could also be used to accomplish similar reactions.

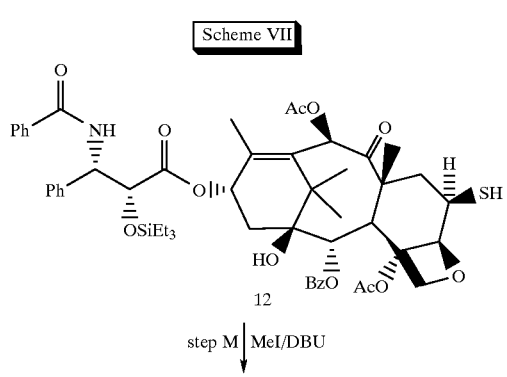
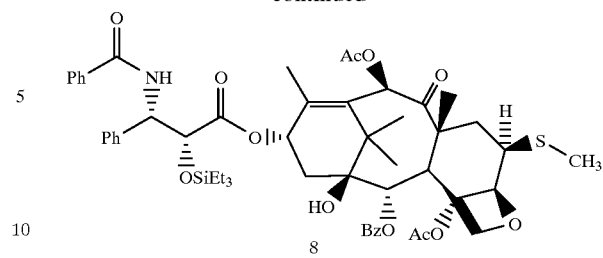
Scheme VIII, step N illustrates the reaction of thiol 12 with ethylene oxide in the presence of catalytic DBU to produce the 2-hydroxyethyl sulfide derivative 14. Standard removal of the 2' protecting group provides hydroxy sulfide 15 which is a compound with useful antitumor properties.
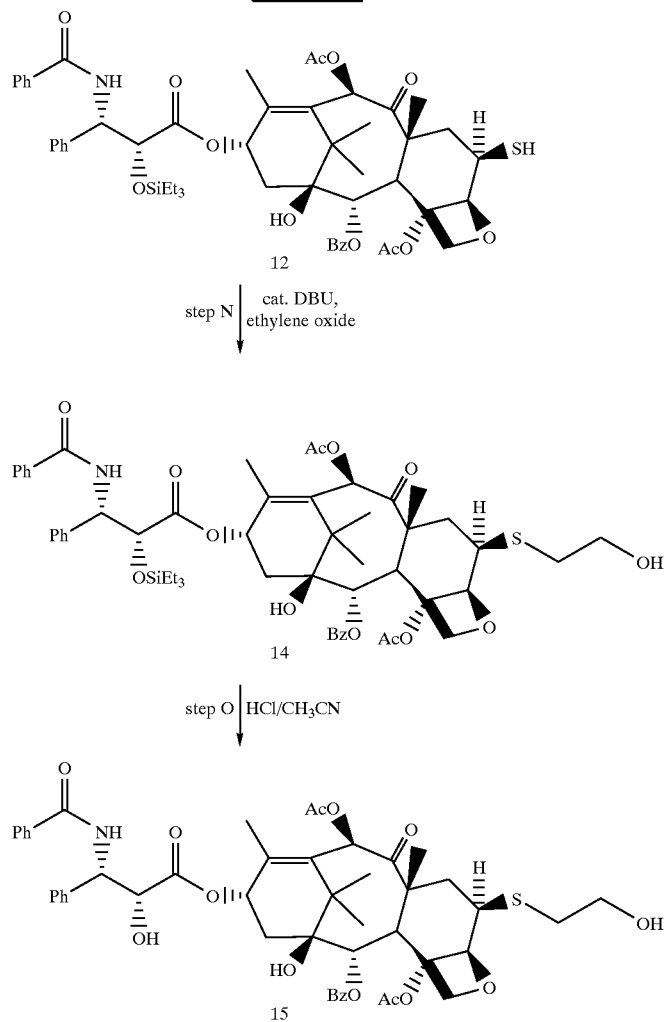

Reaction of triflate 7 (Scheme IX) with potassium thiocyanate in a suitable solvent such as DMF at an elevated temperature of approximately 100° provided the thiocyanate intermediate 16 as well as the deprotected compound 17. Standard deprotection provided 17, which is a compound with useful antitumor properties.

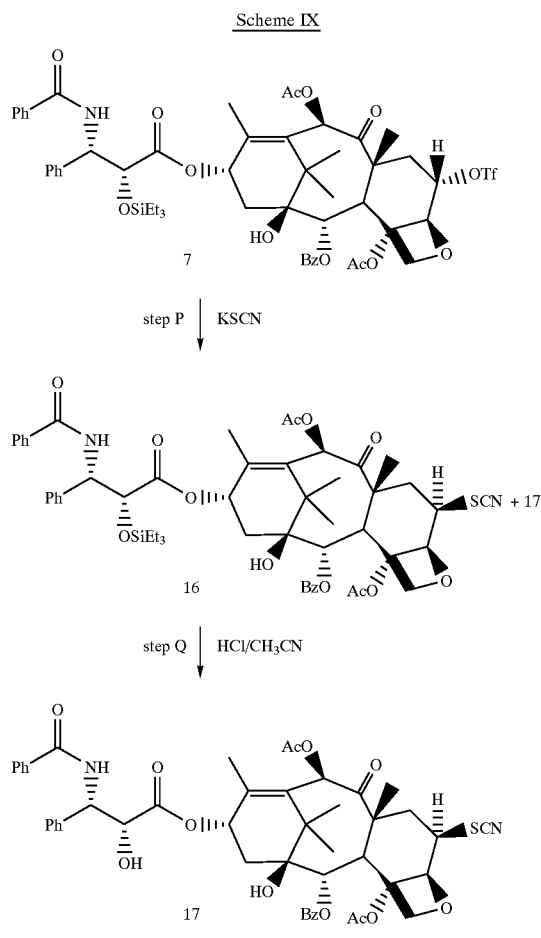

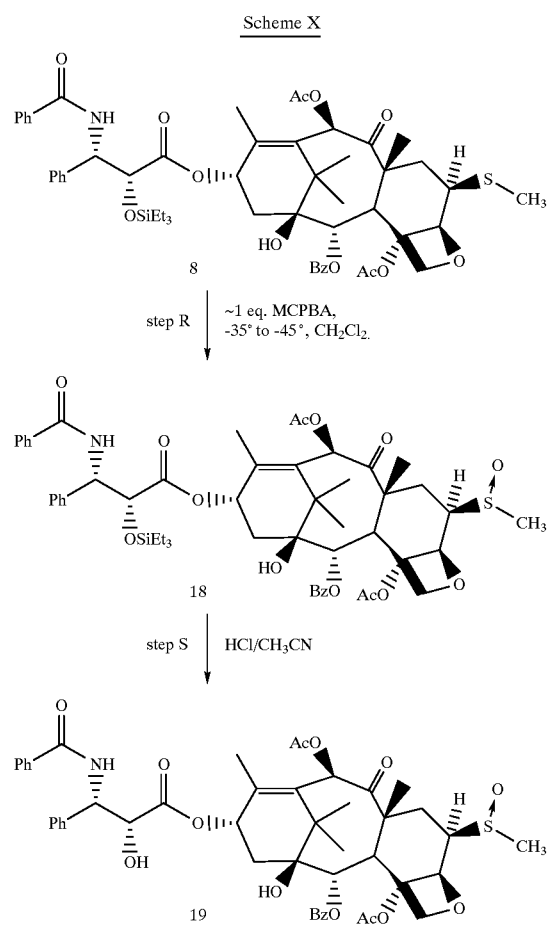

As shown in Scheme X and Scheme XI C-6 sulfide derivatives can be oxidized to produce either sulfoxides (both diastereoisomers) or sulfones. Using 1 eq. of MCPBA (Step R) produces sulfoxide 18 which can be deprotected to provide 19. It is likely that reversing the sequence of these steps could also result in the same outcome. Similarly, as shown in Scheme XI, use of two equivalents of oxidizing agent (step T) results in the formation of a sulfone 20 which after deprotection provides the target compound 21. Other peracids or standard oxidizing agents for sulfur should work similarly.

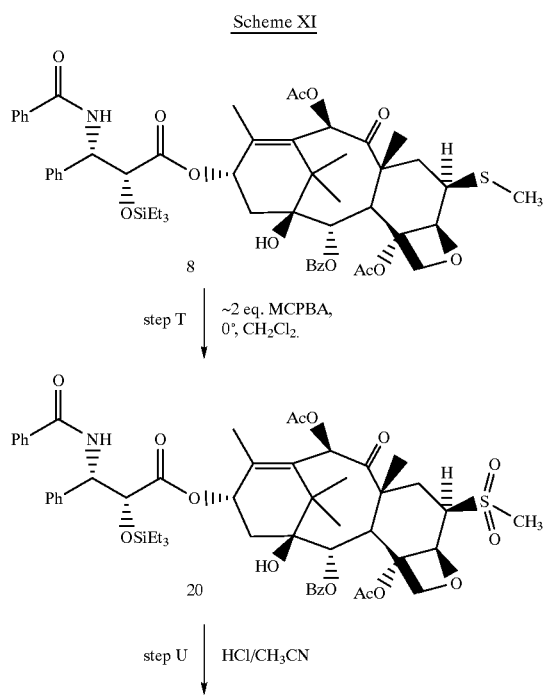

17

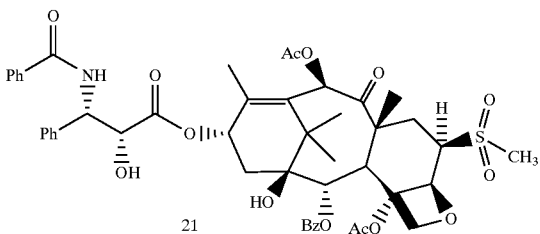

21

Scheme XII

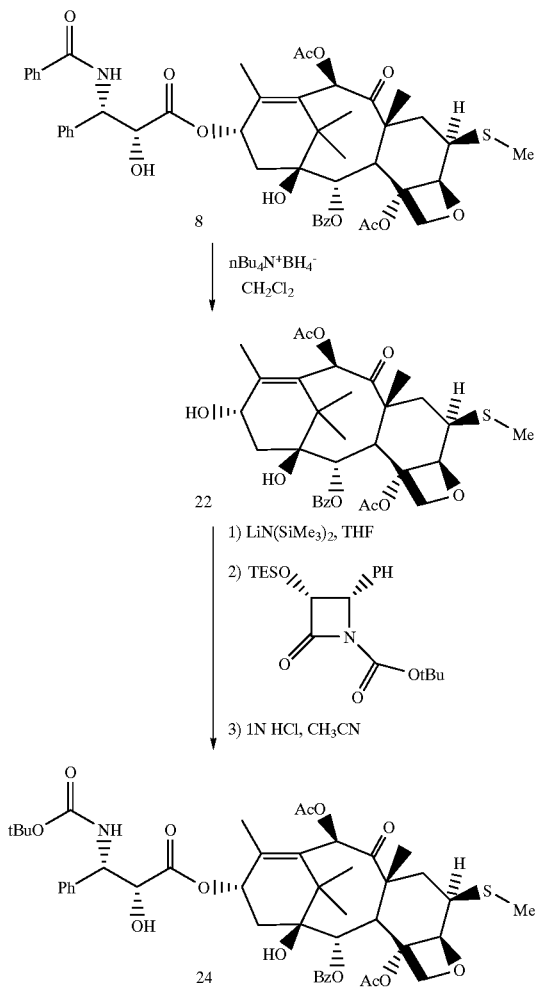

The examples shown in Schemes I–XI describe compounds containing a paclitaxel sidechain. It is well known in the art that chemistry that works with a paclitaxel sidechain works with other standard sidechains or on baccatin III analogs which contain a suitably protected C-13 hydroxy group. Examples of suitable C-13 protecting groups include trialkylsilyl, TROC, or phenoxy acetate.

Scheme XII illustrates the preparation of a taxane analog having a modified paclitaxel side chain.

Some of the schemes refer to a hydroxy protecting group, preferably trialkylsilyl group. It is to be understood that hydroxy protecting group may be a carbonate or ester group —C(O)OR$^x$ or —C(O)R$^x$. Thus when such a group is employed as a hydroxy protecting group, it may either be removed to generate the free hydroxy protecting group or it may remain as a part of the final product.

By now there are many publications teaching the introduction of a wide variety of groups onto a taxane core. By using these well established methods or obvious variants thereof, the starting taxanes of formula VII, or hydroxy protected analogues thereof, can be readily made. For example, for transforming C4-acetoxy into other functional groups see, S. H. Chen et al., *J. Organic Chemistry*, 59, pp 6156–6158 (1994) and PCT application WO 94/14787 published Jul. 7, 1994; for converting C2-benzoyloxy to other groups see, S. H. Chen et al, *Bioorganic and Medicinal Chemistry Letters*, Vol. 4, No. 3, pp 479–482 (1994); K. C. Nicolaou et al., *J. Am. Chem. Soc.*, 1995, 117, 2409 and European Patent Application 617,034A1 published Sep. 28, 1994; for modifying C10-acetyloxy see, K. V. Rao et al., *J. Med. Chem.*, 38, pp 3411–3414 (1995), J. Kant et al., *Tetrahedron Letters*, Vol. 35, No. 31, pp 5543–5546 (1994); and U.S. Pat. No. 5,294,637 issued Mar. 15, 1994; for making C10 and/or C7 unsubstituted (deoxy) derivatives see, European Patent Application 590,267A2 published Apr. 6, 1994 and PCT application WO 93/06093 published Apr. 1, 1993; for making C-10 epi hydroxy or acyloxy compounds see PCT application WO 96/03394; for making C-10 deoxy-C-10 alkyl analogs see PCT application WO95/33740; for making 7b, 8b-methano, 6a, 7a-dihydroxy and 6,7-olefinic groups see, R. A. Johnson, *Tetrahedron Letters*, Vol. 35, No 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingston, *Tetrahedron Letters*, Vol. 36, No. 17, pp 2901–2904 (1995); for making C7-epi-fluoro see, G. Roth et al, *Tetrahedron Letters*, Vol 36, pp 1609–1612 (1995); for forming C7 esters and carbonates see, U.S. Pat. No. 5,272,171 issued Dec. 21, 1993 and S. H. Chen et al., *Tetrahedron*, 49, No. 14, pp 2805–2828 (1993); for 9a- and 9b-hydroxy taxanes see, L. L. Klein, *Tetrahedron Letters*, Vol 34, No 13, pp 2047–2050 (1993), PCT application WO 94/08984 published Apr. 28, 1994, U.S. Pat. No. 5,352,806 issued Oct. 4, 1994, PCT application WO 94/20485 published Sep. 15, 1994, and G. I. Georg et. al. *Tetrahedron Letters*, Vol 36, No 11, pp 1783–1786 (1995). Substituents containing a sulfur atom attached to the taxane core have been reported in European Publication 0604910A1 published on Jul. 6, 1994 and PCT Application WO 96/00724 published on Jan. 11, 1996. However, such sulfur atoms are not directly bonded to the taxane core as are the compounds herein invented.

DESCRIPTION OF SPECIFIC EMBODIMENTS

The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); $(DHQ)_2PHAL$ (hydroquinine 1,4-phthalazinediyl diether). Tf=triflate=trifluoromethanesulfonate; LRMS (low resolution mass spectrometry); ESI (electrospray ionization); MCPBA (meta-chloroperoxybenzoic acid).

Also isometric substituent orientations on the taxane molecule are indicated as "a" or "α" meaning in the down position from the planar position of the taxane molecule (e.g. 6a- or 6α- or 6-alpha); "b" or "β" means the up position for the substituent relative to the taxane molecular plane (e.g. 7b - or 7β- or 7-beta).

PREPARATION OF STARTING MATERIALS
(SCHEME I)

2'-O-(triethylsilyl)-paclitaxel [1]

Paclitaxel (15 g, 17.57 mmol) was dissolved in a solution of 60 mL of pyridine and 60 mL of dichloromethane and then the mixture was cooled to 0° C. Triethylsilyl chloride (11.8 mL, 70.3 mmol) and the reaction was stirred for 90 min at 0°. The reaction was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.0 g (99%) of the title compound.

2'-O-(tertbutyldimethylsilyl)-paclitaxel [1a]

Paclitaxel (146.0 mg, 0.17 mmol) was dissolved in dry N,N-dimethylformamide (1 mL). To this solution imidazole (116.1 mg, 1.7 mmol) and t-butyldimethylsilyl chloride (128.8 mg, 0.85 mmol) were added successively and the mixture was stirred at 60° C. for 1 hour. The reaction mixture was then diluted with ethyl acetate (2 mL), followed by water. The aqueous layer was washed with additional ethyl acetate (2×2 mL). The combined organic layers were then washed with water and brine, dried over sodium sulfate, and evaporated to give crude product. Purification of the crude product by preparative TLC (silica gel, 7:3 hexane-:ethyl acetate) furnished 2'-O-(t-btuyldimethylsilyl)-paclitaxel (157 mg, 95% yield). $^1H$ NMR ($CDCl_3$, TMS, 400 MHz) δ 8.13 (d, 2H, J=7.0), 7.73 (d, 2H, J=7.0), 7.62–7.23 (m, 11H), 7.06 (d, 1H, J=8.9, $H_{NH}$), 6.28 (t, 2H, J=8.9, $H_{10}$, $H_{13'}$), 5.74–5.67(m, 2H, $H_{3'}$, $H_2$), 1H, J=7.7, $H_5$), 4.65 (d, 1H, J=2.2, $H_{2'}$), 4.50–4.40 (m, 1H, $H_7$), 4.32 (d, 1H, J=8.4, $H_{20}$), 4.21 (d, 1H, J=8.4, $H_{20}$), 3.83 (d, 1H, J=7.1, $H_3$), 2.57 (s, 3H, —$CH_3$), 2.54 (m, 1H, $H_6$), 2.45–2.35 (m, 2H, 7—OH, $H_{14}$), 2.22 (s, 3H, —$CH_3$), 2.10 (m, 1H, $H_{14}$), 1.89 (s, 3H, —$CH_3$), 1.85 (m, 1H, $H_6$), 1.68 (s, 3H, —$CH_3$), 1.23 (s, 3H, —$CH_3$), 1.12 (s, 3H, —$CH_3$), 0.80 (s, 9H), –0.05 (s, 3H), –0.3 (s, 3H). LRFABMS m/z calcd for $C_{47}H_{52}NO_{15}$ [MH]$^+$ 968, found 968.

2'-O-(triethylsilyl)-7b-O-trifluoromethanesulfonylpaclitaxel [2]

The alcohol 1 (17 g, 17.5 mmol) and DMAP (8.55 g, 70 mmol) was dissolved in dichloromethane and then the mixture was cooled to 0° C. Trifluoromethanesulfonic anhydride (3.39 mL, 20.1 mmol) was added via syringe and then reaction was allow ed to warm to ambient temperature. The reaction was stirred for 2 hours, was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.6 g (91%) of the title compound.

2'-O-(tertbutyldimethylsilyl)-7b-O-trfluoromethanesulfonylpaclitaxel [2a]

2'-O-(t-butyldimethylsilyl)paclitaxel [1a] (180.0 mg, 0.19 mmol) was dissolved in dry $CH_2Cl_2$ (2 ml.). To this solution 4-dimethylaminopyridine (61.0 mg, 0.5 mmol) and trifluoromethanesulfonyl chloride (50 mL, 0.5 mmol) were added successively at 0° C. and the mixture was stirred at room temperature for 1 hour. Then to this solution addtional 4-dimethylamino pyridine (61.0 mg, 0.5 mmol) and trifluoromethanesulfonyl chloride (50 mL, 0.5 mmol) were added successively and the mixture was stirred at room temperature for additional 1.5 hours. The reaction mixture then was diuted with EtOAc (4.0 mL) and the precipitate was filtered off on Celite. The solvent was evaporated, and the residue was purified by preparative TLC (silica gel, 6:4 hexane:EtOAc) to furnish 2'-O-(t-butyldimethylsilyl)-7-O-trifluoromethaneslfonylpaclitaxel (187.0 mg, 92% yield). $^1H$ NMR ($CDCl_3$, TMS, 400 MHz) δ 8.12 (d, 2H), 7.73 (d, 2H), 7.60 (t, 1H), 7.53–7.30 (m, 10H), 7.09 (d, 1H, J=8.9, $H_{NH}$), 6.62 (s, 1H, $H_{10}$), 6.25 (t, 1H, J=9.2, $H_{13}$), 5.76 (q, 1H, J=8.9, 2.6, $H_3$), 5.74 (d, 1H J=7.0, $H_2$), 5.49 (dd, 1H, J=7.5, 10.1, $H_7$), 4.94 (d 1H, J=8.6, $H_5$) 4.67 (d, 1H, J=2.0, $H_{2'}$), 4.37 (d, 1H, J=8.5, $H_{20}$), 4.22 (d, 1H, J=8.5, $H_{20}$), 3.97 (d, 1H, J=7.0, $H_3$),2.85 (m, 1H, $H_6$) 2.60 (s, 3H, —$CH_3$), 2.39 (m, 1H, $H_{14}$), 2.19 (s, 3H, —$CH_3$), 2.18 (m, 2H, $H_6$, $H_{14}$), 2.08 (s, 3H, —$CH_3$), 1.89 (s, 3H, —$CH_3$), 1.22 (s, 3H, —$CH_3$), 1.18 (s, 3H, —$CH_3$), 0.8 (s, 9H), –0.02 (s, 3H), –0.29 (s, 3H). $^{13}C$ NMR ($CDCL_3$, TMS, 100 MHz) δ 200.97, 171.89, 171.16, 169.34, 167.71, 167.42, 141.75, 138.77, 134.66, 134.45, 133.43, 132.46, 130.84, 129.52, 129.47, 129.40, 129.38, 128.65, 127.59, 127.00, 86.39, 83.68, 80.64, 79.25, 76.94, 75.77, 75.74, 74.92, 71.69, 57.97, 56.23, 47.55, 43.75, 36.32, 34.67, 26.76, 26.23, 26.13, 23.47, 22.01, 21.29, 18.75, 14.87, 14.80, 11.538, –4.54, –5.20. LRFABMS m/z calcd for $C_{54}H_{65}NO_{16}F_3SiS$ [MH]$^+$ 1100, found 1100.

2'-O-(triethylsilyl)-6,7-dehydropaclitaxel [3]

The triflate 2 (17.6 g, 16 mmol) was dissolved in 75 mL of dry THF and then 12.18 g (80 mmol) of DBU was added. The reaction was heated at reflux for 2 hours and then diluted with ethyl acetate. The organic layer was washed five times with water and then brine, dried over anhydrous magnesium sulfate, filtered, and concentrated in vacuo. The crude product was dissovled in methylene chloride and then 16 mmol of imidazole and 8 mmol of triethylsilyl chloride were added. The reaction was stirred for 1.5 h at ambient temperature, diluted with ethyl acetate, washed with two portions of water, dried over anhydrous magnesium sulfate and concentrated in vacuo. The crude material was purified by flash chromatography over silica gel using 2:1 hexane/ethyl acetate as eluent to provide 15.0 g (99%) of the title compound.

2'-O-(tertbutyldimethylsilyl)-6,7-dehydropaclitaxel [3a]

To a stirred solution of 2'-(t-butyldimethylsilyl)-7b-trifluoromethanesulfonylpaclitaxel [2a], (202.0 mg, 0.18 mmol) in dry dichloromethane (1.0 mL) was added 1,8-diazabicyclo (5,4,0) undec-7-ene (DBU, 300.0 ml, 2.0 mmol). The mixture was kept stirring at 40° C. for 4 hours. The reaction mixture then was diluted with ethyl acetate (2.0 ml) and washed with diluted HCl, diluted NaHCO$_3$ solution, water and brine. The aqueous layer was extracted with additional ethyl acetate (2×2 mL). The combined organic layers were dried over sodium sulfate and evaporated to give crude product. Purification of the crude product by preparative silica gel TLC (7:3 hexane:ethyl acetate) furnished two compounds: 2'-(t-butyldimethylsilyl)-6,7-dehydropaclitaxel [3a] (150.0 mg, 86%) and 6,7-dehydropaclitaxel (21.3 mg, 13.9%). Spectoscopic data for 3a: $^1$H-NMR (CDCl$_3$, TMS, 400 MHz) δ 8.12 (d, 2H), 7.73 (d, 2H), 7.60 (t, 1H), 7.53–7.30 (m, 5H), 7.07 (d, 1H), J=8.9, H$_{NH}$), 6.24 (s, 1H, H$_{10}$), 6.25 (t, 1H, J=9.2, H$_{13}$), 6.08 (dd, 1H, J=9.9, 5.6, H$_6$), 5.87 (d, 1H, J=9.9, H$_7$), 5.86 (d, 1H, J=6.5, H$_2$), 5.72 (d, 1H, J=8.6, H$_3$), 5.12 (d 1H, J=5.5, H$_5$), 4.65 (d, 1H, J=2.0, H$_{2'}$), 4.45 (d, 1H, J=8.1, H$_{20}$), 4.34 (d, 1H, J=8.1, H$_{20}$), 4.03 (d, 1H, J=6.5, H$_3$), 2.58 (s, 3H, —CH$_3$), 2.44 (m, 1H, H$_{14}$), 2.22 (s, 3H, —CH$_3$), 2.18 (m, 2 H, H$_6$, H$_{14}$), 1.88 (s, 3H, —CH$_3$), 1.83 (s, 3H, —CH$_3$), 1.24 (s, 3H, —CH$_3$), 1.14 (s, 3H, —CH$_3$), 0.79 (s, 9H), −0.05 (s, 3H), −0.32 (s, 3H). $^{13}$C NMR (CDCl$_3$, TMS, 100 MHz) δ 205.44, 171.32, 169.56, 169.39, 166.91, 166.87, 141.60, 140.03, 138.27, 134.06, 133.67, 133.61, 131.76, 130.19, 129.16, 128.80, 128.73, 128.71, 128.69, 127.92, 126.96, 126.36, 126.126, 81.22, 81.12, 76.31, 75.82, 75.64, 75.12, 71.23, 60.36, 55.65, 55.40, 35.98, 26.29, 25.49, 23.14, 22.12, 22.02, 20.744, 20.46, 18.09, 14.62, 14.17, −5.28, −5.89. LRFABMS m/z calcd for C$_{53}$H$_{64}$NO$_{13}$Si [MH]$^+$ 950, found 950.

2'-O-(triethylsilyl)-6a-hydroxy-7-epi-paclitaxel [4]

The olefin 3 was dissolved in 180 mL of acetone and 22.5 mL of water. NMO (4.06 g, 34.74 mmol) and OsO$_4$ (0.200 g, 0.79 mmol) were added and the reaction was stirred for 12 days. Silica gel was added and the reaction was concentrated in vacuo to provide a near free flowing powder which was placed on top of a flash chromatography silica gel column. Elution with 1:1 hexane/ethyl acetate provided 13.35 g (86%) of the desired diol.

2'-O-(tertbutyldimethylsilyl)-6a-hydroxy-7-epi-paclitaxel [4a]

To a solution of 2'-O-(t-butyldimethylsilyl)-6,7-dehydropaclitaxel [3a], (60.0 mg, 0.063 mmol) in THF (500 mL, 10 drops H$_2$O) were added osmium tetraoxide (2.5 wt. 2.5% solution in 2-methyl-2-propanol, 150 mL, 0.015 mmol) and 4-methyl morpholine-N-oxide (NMO, 50 mg, 0.42 mmol). The mixture was kept stirring at room temperature for 4 hours. Additional osmium tetraoxide solution (150 mL, 0.015 mmol) was then added to the reaction mixture to accelerate the reaction. The reaction mixture was kept stirring at room temperature for additional 5 hours. To the reaction solution was added sodium bisulfite (25 mg) and the mixture was stirred for 10 minutes, then diluted with EtOAc (1 mL), filtered through Celite, and washed with H$_2$O and brine. The aqueous layer was extracted with additional EtOAc (2×2 mL). The combined organic layers were dried over Na$_2$SO$_4$ and evaporated. Isolation of the residue oln preparative TLC plate (silica gel, 1:1 hexane:EtOAc) furnished starting material (7.2 mg, 12%) and a more polar compound 2'-O-(t-butyldimethylsilyl)-6a-hydroxy-7-epi-paclitaxel [4a] (48.0 mg, 78% yield). $^1$H NMR (CDCl$_3$, TMS, 400 MHz) δ 8.15 (d, 2H), 7.70 (d, 2H), 7.64–7.26 (m, 6H), 7.07 (d, 1H, J=8.8, H$_{NH}$), 6.83 (s, 1H, H$_{10}$), 6.29 (t, 1H, J=8.8, H$_{13}$), 5.79 (q, 1H, J=8.8, 2.4, H$_3$.), 5.74 (d, 1H, J=7.6, H$_2$), 4.71 (d, 1H, J=12.0, H$_{7—OH}$), 4.68 (d, 1H, J=2.0, H$_5$), 4.66 (bs, 2H, H$_{20}$), 4.36 (s, 1H, H$_{2'}$), 4.18 (m, 1H, H$_6$), 3.87 (d, 1H, J=7.6, H$_3$), 3.70 (q, 1H, J=5.2, 12.0, H$_7$), 2.90 (d, 1H, J=8.2, H$_{6—OH}$), 2.62 (s, 3H, —CH$_3$), 2.42–2.10 (m, 2H, H$_{14}$), 2.18 (s, 3H, —CH$_3$), 1.90 (s, 3H, —CH$_3$), 1.62 (s, 3H, —CH$_3$), 1.18 (s, 3H, —CH$_3$), 1.12 (s, 3H, —CH$_3$), 0.78 (s, 9H), −0.03 (s, 3H), −0.3 (s, 3H). HRFABMS m/z calcd for C$_{47}$H$_{52}$NO$_{15}$ [MH]$^+$ 870.3337, found 870.3336.

EXAMPLE 1

Preparation of 7-deoxy-6a-hydroxypaclitaxel[6]-(Scheme II)

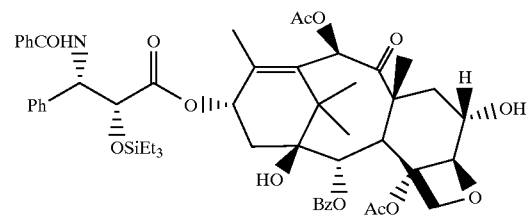

6

The diol 4 (1.773 g, 1.809 mmol), thiocarbonyldiimidazole(0.996 g, 5.427 mmol), DMAP (0.618 g, 5.065 mmol) were dissolved in 50 mL THF and allowed to stir overnight. The reaction was diluted with EtOAc, washed with NaHCO$_3$, and brine. The solution was dried over MgSO$_4$, filtered, and concentrated. The residue was chromatographed over silica gel (1:1 hexane/ethyl acetate) to yield 1.646 g of product 5 (89%).

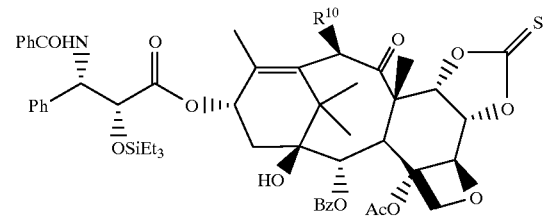

5

ESILRMS M+NH$_4$$^+$calcd. for C$_{54}$H$_{63}$O$_{15}$N$_2$S Si: 1043. Found: 1043. Anal. calcd. for C$_{54}$H$_{63}$O$_{15}$N S Si: C, 63.20; H, 6.19; N, 1.36. Found: C, 63.04; H, 6.22; N, 1.33. IR(KBr) 3438(br.), 2958, 1746, 1717, 1282, 1236 cm$^{-1}$.

$^1$H NMR (CDCl$_3$, 300 MHz) δ 8.15(d, J=7.2 Hz, 2H), 7.74(d, J=7.2 Hz, 2H), 7.63–7.32(m, 11H), 7.12(d, J=9.0 Hz, 1H), 6.87(s, 1H), 6.25(br. t., 1H), 5.83(d, J=6.9Hz, 1H), 5.70(d, J=9.0, 1H), 4.97(d, J=11.4 Hz, 1H), 4.87(s, 1H), 4.72(m, 2H), 4.39(d, J=8.1 Hz, 1H), 4.22(d, J=8.1 Hz, 1H), 4.00(D, J=6.9 Hz, 1H), 2.57(s, 3H), 2.43–2.35(m, 1H), 2.21(s, 3H), 2.16–2.08(m, 1H), 2.03(m, 4H), 1.87(s, 3H), 1.21(s, 3H), 1.17(s, 3H), 0.79(m, 9H), 0.44(m, 6H).

The thiocarbonate 5 (0.200 g, 0.196 mmol), AIBN(cat.), (aza-isobutyrylnitrile (catalytic)) and Bu₃GeH(0.479 g, 1.96 mmol) were dissolved in 3 mL toluene under Argon. The reaction mixture was frozen, dried in vacuo, and thawed three times to remove O₂. The reaction was heated to 85° C. for 1 hr. The reaction mixture was concentrated and chromatographed over silica gel (1.5:1 hexane/ethyl acetate) to yield 0.137 g of product 6 (72%).

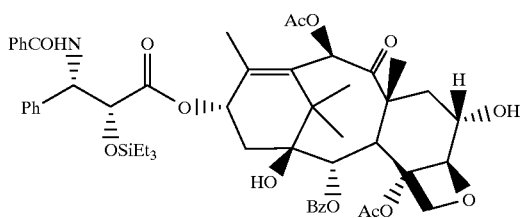

6

ESILRMS M+H calcd for $C_{53}H_{65}O_{14}N$ Si: 968. Found: 968. Anal. calcd. for $C_{53}H_{65}O_{14}NSi$—$H_2O$: C, 64.55; H, 6.85; H, 1.42. Found: C, 64.49; H, 6.82; N, 1.41. IR(KBr) 3442(br.), 2956, 1734, 1486, 1372, 1244, 710 cm⁻¹.

¹H NMR (CDCl₃, 300 MHz) δ 8.13(d, J=8.7 Hz, 2H), 7.72(d, J=8.4 Hz, 2H), 7.62–7.33(m, 11H), 7.10(d, J=8.7 Hz, 1H), 6.45(s, 1H), 6.24(t, J=8.7 Hz, 1H), 5.71–5.64(m, 2H), 4.80(s, 1H), 4.66(d, J=2.1 Hz, 1H), 4.31(d, J=8.4 Hz, 1H), 4.18–4.14(m, 2H), 3.78(d, J=7.5 Hz, 1H), 2.54(s, 3H), 2.48–2.39(m, 1H), 2.20(s, 3H), 2.17–2.08(m, 1H), 2.02(d, J=9.0 Hz, 2H), 1.90(s, 4H), 1.77(s, 1H), 1.71(s, 3H), 1.19(s, 3H), 1.10(s, 3H), 0.79(m, 9H), 0.41(m, 6H).

EXAMPLE 1a

Preparation of 2'-O-(tertbutyldimethylsilyl)-6a-hydroxy-7-deoxypaclitaxel[6a]-(Scheme II)

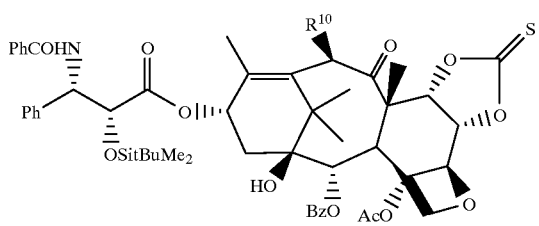

5a

A solution of (4a) (12.70 g, 12.9 mmoles) in anhydrous THF (300.0 mL) was treated with dimethylaminopyridine (4.73 g, 38.71 mmoles) and 1,1'-thiocarbonyl-diimidazole (7.0 g, 38.71 mmoles). After 3 days, the crude reaction mixture was poured into ethyl acetate (500 mL) and washed with a saturated solution of NaHCO₃ (2×100 mL) followed by brine (2×50 mL). The mixture was dried over anhydrous Na₂SO₄, filtered and concentrated in vacuo. Purification by column chromatography on silica eluting with 60%-50% hexanes/ethyl acetate afforded 12.9 g (97.4% yield, 92.7% pure by HPLC analysis) of compound 5a as an off-white, amorphous powder which exhibited the following physical properties: LRMS (ESI): 1084.5 ((M+NH₄+ACN)⁺, 35%), 1043.5 ((M+NH₄)⁺, 45%), 1026.5 ((M+1)⁺, 100%).

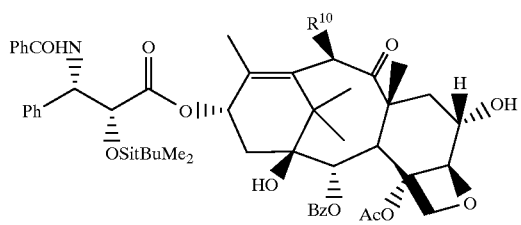

6a

A solution of compound 5a (13.4 g, 13.03 mmoles) in anhydrous THF (65.0 mL) was degassed three times using a vacuum freeze/thaw technique. The mixture was heated to reflux under an argon atmosphere and was treated with a solution containing tributylgermanium hydride (20.0 g, 81.65 mmoles) and AIBN (257.1 mg, 1.56 mmoles) in anhydrous THF (15.0 mL) dropwise via syringe over a 5 min. period. After 64 mins., the reaction mixture was allowed to cool to ambient temperature and concentrated in vacuo. The residue was dissolved in acetonitrile (300 mL) and washed with heptane (2×100 mL) and then concentrated in vacuo. Purification by column chromatography on silica eluting with 60% hexanes/ethyl acetate afforded 7.9 g (69.7% yield based on recovered starting material) of compound 6a as an off-white, amorphous powder which exhibited the following physical properties: ¹H NMR (CDCl₃, 300 MHz) δ 8.20 (d, 2H, J=7.1 Hz), 7.78(d, 2H, J=7.1 Hz), 7.68–7.34(m, 11H), 7.13(d, 1H, J=9.0 Hz), 6.52(s, 1H), 6.31(t, 1H, J=9.0 Hz), 5.80(dd, 1H, J=8.9, 1.6), 5.71 (d, 1H, J=7.4 Hz), 4.87(s, 1H), 4.70(d, 1H, J=2.1 Hz), 4.36(d, 1H, J=8.4 Hz), 4.25–4.11(m, 2H), 3.86(d, 1H, J=7.3 Hz), 2.71–0.25(m, 39H, incl. singlets at 2.64, 2.25, 1.97, 1.77, 1.25, 1.17, 0.00, −0.25 3H each and at 0.84 9H) ¹³C NMR (CDCl₃, 75.469 Mhz) δ: 205.05, 171.36, 170.64, 169.63, 167.19, 167.01, 140.92, 138.38, 134.19, 133.78, 133.38, 131.88, 130.34, 129.25, 128.92, 128.85, 128.82, 128.08, 127.09, 126.49, 92.89, 83.91, 79.14, 75.49, 75.35, 73.97, 71.29, 70.90, 55.71, 53.34, 45.04, 44.20, 43.06, 36.20, 26.23, 25.61, 23.06, 21.82, 18.24, 15.32, 14.65

IR(KBr) 3442(br.), 2953, 2858, 1731, 1719, 1485, 1371, 1244, 839, 710 cm⁻¹. LRESIMS m/z Calcd. for $C_{53}H_{65}NO_{14}Si$ [M—H]⁻ 967. Found 967

EXAMPLE 2

2'-O-(triethylsilyl)-7-deoxy-6α-triflouromethanesulphonyloxypaclitaxel [7]

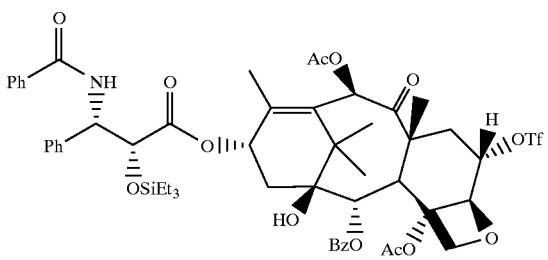

7

The alcohol 6 (0.950 g, 0.98 mmol) and DMAP (0.479 g, 3.92 mmol) were dissolved in 10 mL of dichloromethane and cooled to 0° C. under nitrogen. Triflic anhydride (198 μL, 1.18 mmol) was added via syringe, and the reaction was allowed to stir at 0° C. for 10 min. The crude reaction mixture was placed directly onto a vacuum funnel containing a 1.5 inch plug of silica gel wet with hexanes, and eluted with (3:1 hexanes/ethyl acetate) to provide the triflate 7 (0.842 g 78%) as a white powder.

$^1$H NMR (CDCl$_3$ 300 MHz)δ: 8.13 (d, 2H), 7.72 (d, 2H), 7.50–7.25 (m, 11H), 7.10 (d, 1H, J=9.1, H$_{NH}$), 6.41 (s, 1H, H$_{10}$), 6.25 (t, 1H, J=8.6 H$_{13}$), 5.73 (d, 1H, J=9.0, H$_3$.), 5.64 (d, 1H, J=7.5, H$_2$), 5.22 (dd, 1H, J=11.7, 7.5, H$_6$), 4.98 (s, 1H, H$_5$), 4.68 (d, 1H, J=2.0, H$_2$.), 4.33 (d, 1H, J=8.5, H$_{20}$), 4.26 (d, 1H, J=8.6, H$_{20}$), 3.89 (d, 1H, J=7.4, H$_3$), 2.58 (s, 3H, Ac), 2.50–2.40 (m, 2H), 2.21 (s, 3H, Ac), 2.19–2.04 (m, 2H), 1.92 (s, 3H, H$_{18}$), 1.71 (s, 3H, H$_{19}$), 1.21 (s, 3H, H$_{16}$), 1.10 (s, 3H, H$_{17}$), 0.78 (m, 9H), 0.43 (m, 6H)

$^{13}$C NMR (CDCl$_3$, 75.469 MHz)δ: 203.94, 171.47, 170.26, 169.58, 167.06, 167.01, 141.57, 138.39, 134.12, 133.93, 133.08, 131.87, 130.30, 128.97, 128.83, 128.77, 128.11, 127.09, 126.44, 88.38, 87.31, 84.00, 79.06, 75.05, 75.00, 73.93, 71.12, 55.66, 52.57, 44.41, 42.97, 40.16, 36.28, 26.19, 22.85, 21.86, 20.77, 15.56, 14.62, 14.40, 6.57, 4.42. LRESIMS m/z Calcd. for C$_{54}$H$_{64}$F$_3$NO$_{16}$SSi [M—H]$^-$ 1099, found 1099. IR (cm$^{-1}$): 3442.61, 2957.67, 1748.72, 1735.68, 1725.17, 1245.93, 1225.00, 1143.23, 925.19, 710.48.

EXAMPLE 2a
2'-O-(tertbutyldimethylsilyl)-7-deoxy-6α-trifluoromethanesulphonyloxypaclitaxel [7a]

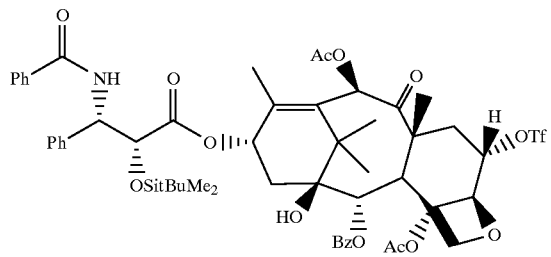

A solution of 2'-tert-butyldimethylsilyl-6-α-hydroxy-7-deoxy-paclitaxel (6a) (7.90 g, 8.16 mmoles) in anhydrous DCM (82.0 mL) was cooled to 0° C. and treated with dimethylaminopyridine (3.98 g, 32.63 mmoles) and trifluoromethanesulfonic anhydride (1.65 mL, 9.79 mmoles). After 10 mins. the crude reaction mixture was columned through a short pad of silica gel eluting with 75% hexanes/ethyl acetate to provide 7.56 g (84.2%,) of compound 7a as a white, amorphous powder which exhibited the following physical properties: $^1$H NMR (CDCl$_3$, 300 MHz) δ 8.12 (d, J=7.0 Hz, 2H), 7.70 (d, J=7.0 Hz, 2H), 7.61–7.24 (m, 11H), 7.05 (d, J=9.1 Hz, 1H), 6.40 (s, 1H), 6.25 (t, J=8.6 Hz, 1H), 5.75 (d, J=9.1 Hz, 1H), 5.64 (d, J=7.3 Hz, 1H), 5.20 (dd, J=7.6 Hz, J=11.5 Hz, 1H), 4.97 (s, 1H), 4.64 (d, J=2.1 Hz, 1H), 4.28 (dd, J=8.5 Hz, J=19.2, 2H), 3.88 (d, J=7.3 Hz, 1H), 2.60 (s, 3H), 2.54–2.37 (m, 2H), 2.19 (s, 3H), 2.16–2.02 (m, 2H), 1.94 (s, 1H), 1.91 (s, 3H), 1.72 (s, 3H), 1.19 (s, 3H), 1.09 (s, 3H), 0.77 (s, 9H), −0.07 (s, 3H), −0.31 (s, 3H); LRMS (ESI): 1117.5 ((M+NH$_4$)$^+$, 25%), 1100.5 ((M+1)$^+$, 100%). $^{13}$C NMR (CDCl$_3$, 75.469 MHz)δ: 203.96, 171.31, 170.34, 169.59, 167.06, 167.01, 141.59, 138.29, 134.16, 133.97, 133.09, 131.92, 130.34, 129.01, 128.97, 128.89, 128.83, 128.12, 127.08, 126.44, 88.41, 87.29, 84.03, 79.13, 75.36, 75.07, 73.95, 71.08, 55.64, 52.61, 44.46, 42.99, 40.21, 36.33, 26.22, 25.60, 22.93, 21.90, 20.79, 18.25, 15.59 and 14.72 IR (cm$^{-1}$): 3443.26, 2954.41, 2935.16, 1752.33, 1734.72, 1725.90, 1246.20, 1227.94, 1143.48, 925.48, 838.88, 710.31.

EXAMPLE 3
2'-O-(triethylsilyl)-7-deoxy-6β-thiomethylpaclitaxel [8]

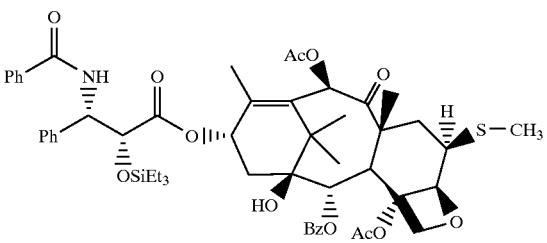

Triflate 7 (0.80 g, 0.73 mmol) was mixed with sodium thiomethoxide (0.05 g, 0.73 mmol) under nitrogen and cooled to 0° C. DMF (5 mL) was added and the solution was stirred at 0° C. for 20 min. Additional sodium thiomethoxide (0.005 g, 0.07 mmol) was added and stirring was continued for another 20 min. The reaction was diluted with ethyl acetate, washed with water, then brine and dried over MgSO$_4$. Concentration and sequential chromatography over silica gel (hexanes/ethyl acetate 2:1) followed by reversed phase C18 silica gel (acetonitrile/water 3:1) provided 0.04 g of the thiomethyl ether 8 5.5%.

Alternate procedure: Thiol 13 (0.535 g, 0.54 mmol) was dissolved in benzene (10 mL) and cooled to 5° C. Methyl iodide (37 μL, 0.60 mmol) and DBU (99 μL, 0.66 mmol) were added and the reaction was stirred 15 minutes at 0° C. The precipitated salts were filtered off and washed with benzene. The filtrate was stripped to a residue and chromatographed on silica gel (hexanes/ethyl acetate 2:1) to provide 0.507 g of the thiomethyl ether 8 94%.

$^1$H NMR (CDCl$_3$ 300 MHz)δ: 8.05 (d, 2H, J=7.2 H$_{arom}$.), 7.64 (d, 2H, J=7.2, H$_{arom}$.), 7.54–7.17 (m, 11H, H$_{arom}$.), 7.03 (d, 1H, J=8.9, H$_{NH}$), 6.40 (s, 1H, $_{10}$), 6.14 (t, 1H, J=8.6, H$_{13}$), 5.65 (overlapping doublets, 2H, H$_3$.+H$_2$), 4.90 (d, 1H, J=6.3, H$_5$), 4.60 (d, 1H, J=1.7, H$_2$.), 4.25 (d, 1H, J=8.0, H$_{20}$), 4.04 (d, 1H, J=7.9, H$_{20}$), 3.65 (d, 1H, J=6.8, H$_3$), 3.33 (m, 1H, H$_6$), 2.44 (s, 3H, H$_{S-CH3}$), 2.30 (m, 2H), 2.13 (s, 3H, H$_{4-Ac}$), 2.08–2.07 (m, 1H), 1.99 (s, 3H, H$_{10-Ac}$), 1.82 (s, 3H, H$_{CH3}$), 1.81 (s, 3H, H$_{CH3}$), 1.78–1.74 (m, 1H), 1.12 (s, 3H), 1.04 (s, 3H), 0.72 (t, 6H), 0.45–0.24 (m, 9H) $^{13}$C NMR (CDCl$_3$, 75.469 MHz)δ: 205.03, 171.58, 170.14, 169.84, 167.12, 140.85, 138.45, 134.13, 133.71, 133.51, 131.87, 130.27, 129.33, 128.81, 128.78, 128.05, 127.10, 126.52, 85.41, 80.43, 78.83, 75.84, 75.56, 74.95, 73.97, 71.33, 55.74, 53.07, 43.39, 43.15, 41.85, 40.36, 35.92, 26.16, 22.91, 21.85, 20.86, 16.98, 14.97, 14.54, 6.57, 4.43 ESILRMS Calcd. for C$_{54}$H$_{67}$NO$_{13}$SSi [M—H]$^-$ 997. Found 997. IR (cm$^{-1}$): 3441.39, 2956.35, 1747.79, 1732.04, 1716.84, 1484.09, 1371.64, 1267.01, 1241.71, 1108.90, 1069.79, 710.65

EXAMPLE 4

7-deoxy-6β-thiomethylpaclitaxel [9]

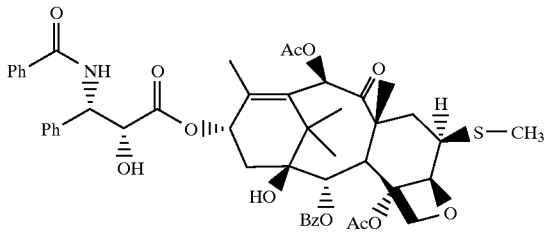

Triethylsilyl ether 8 (0.812 g, 0.81 mmol) was dissolved in acetonitrile (10 mL), cooled to 0° C and treated with 1M HCl (1.63 mL, 1.63 mmol) for 30 minutes. The reaction mixture was concentrated to a residue under vacuum, diluted with acetonitrile and stripped to a residue again. The crude material was chromatographed over silica gel (hexanes/ethyl acetate 1:1). The pure fractions were stripped to a residue, dissolved in a minimal amount of methylene chloride and precipitated with hexanes. This suspension was stripped to a solid residue under vacuum to provide the hydroxy thioether 9 (0.541 g) in 76% yield.

$^1$H NMR (CDCl$_3$ 300 MHz)δ: 8.12 (d, 2H, $_{arom.}$), 7.72 (d, 2H, $_{arom.}$) 7.63–7.30 (m, 11H, $_{arom.}$), 7.07 (d, 1H, J=9.0, $_{NH}$), 6.44 (s, 1H, H$_{10}$), 6.17 (t, 1H, J=8.6, H$_{13}$), 5.79 (d, 1H, J=9.0, H$_{3'}$), 5.72 (d, 1H, J=6.7, H$_2$), 4.96 (d, 1H, J=5.8, H$_5$), 4.78 (s, 1H, H$_{2'}$), 4.31 (d, 1H, J=8.0, H$_{20}$), 4.10 (d, 1H, J=8.0, H$_{20}$), 3.74 (d, 1H, J=6.6, H$_3$), 3.69 (d, 1H, J=4.8, $_{OH}$), 3.37 (m, 1H, H$_6$), 2.37 (s, 3H, $_{4Ac}$), 2.36–2.27 (m, 2H), 2.21 (s, 3H, $_{10Ac}$), 2.06 (s, 3H, $_{S-Me}$), 1.89 (s, 3H, H$_{18}$), 1.86–1.79 (m, 2H), 1.74 (s, 3H, H$_{19}$), 1.29–1.22 (m, 1H), 1.19 (s, 3H, H$_{16}$), 1.12 (s, 3H, H$_{17}$). $^{13}$C NMR (CDCl$_3$, 75.469 MHz)δ: 204.62, 172.38, 170.53, 169.77, 167.13, 166.97, 140.32, 138.10, 133.92, 133.81, 133.73, 132.02, 130.23, 129.23, 129.03, 128.77, 128.37, 127.13, 127.11, 85.61, 80.46, 78.68, 75.65, 73.99, 73.39, 72.08, 54.94, 53.11, 43.19, 43.08, 41.51, 39.86, 35.77, 26.28, 22.55, 21.30, 20.86, 17.39, 14.78, 14.63. LRESIMS m/z Calcd. for C$_{48}$H$_{53}$NO$_{13}$S [M—H]$^-$ 883, found 883. IR(cm$^{-1}$): 3432.18, 2923.28, 1731.96, 1716.03, 1662.18, 1485.68, 1371.89, 1270.91, 1240.56, 1069.82, 1024.85, 968.05, 711.09 Elemental calcd. for C$_{48}$H$_{53}$NO$_{13}$S: C, 65.22; H, 6.04; N, 1.58; S, 3.63. Found: C, 65.38; H, 6.28; N, 1.47; S, 3.44.

EXAMPLE 5

2'-O-(triethylsilyl)-7-deoxy-6β-thioacetoxyclaclitaxel [10]

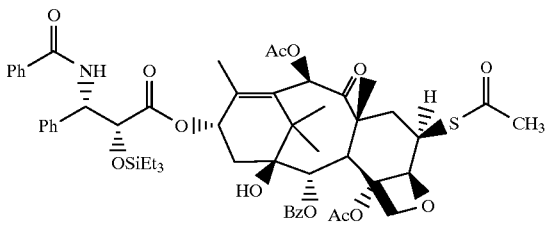

The triflate 7 (1.00 g, 0.91 mmol) was cooled to −10° C. and treated with a solution of potassium thioacetate (0.21 g, 1.82 mmol) in 5 mL DMF also at −10° C. The solution was allowed to warm to room temperature, and stirred for 1.5 hours. The reaction was diluted with ethyl acetate, washed with brine and dried over MgSO$_4$. Concentration followed by radial chromatography over silica gel (hexanes/ethyl acetate 1.5:1) provided (0.893 g, 94%) of the thioacetate 10.

$^1$H NMR (CDCl$_3$ 300 MHz)δ: 7.93 (d, 2H), 7.56 (d, 2H), 7.51–7.05 (m, 11H), 6.90 (d, 1H, J=8.9, H$_{NH}$), 6.26 (s, 1H, H$_{10}$), 6.03 (t, 1H, J=8.4 H$_{13}$), 5.50 (overlapping, 2H, H$_{3'}$+H$_2$), 4.76 (d, 1H, J=7.8, H$_5$), 4.49 (d, 1H, J=2.0, H$_{2'}$), 4.23 (t, 1H, J=7.6, H$_6$) 4.12 (d, 1H, J=8.1, H$_{20}$), 3.91 (d, 1H, J=8.1, H$_{20}$), 3.53 (d, 1H, J=7.0, H$_3$), 2.47 (dd, 1H, J=14.24, 9.1), 2.33 (s, 3H, H$_{SAc}$), 2.20 (m, 1H), 2.08 (s, 3H, H$_{4Ac}$), 1.99 (s, 3H, H$_{10Ac}$), 1.99–1.89 (m, 1H), 1.72 (s, 3H, H$_{18}$) 1.61–1.51 (overlapping, 4H, contains H$_{19}$), 1.00 (s, 3H, H$_{16}$), 0.91 (s, 3H, H$_{17}$), 0.61 (m, 9H), 0.24 (m, 6H) $^{13}$C NMR (CDCl$_3$, 75.469 MHz)δ: 205.10, 194.36, 171.55, 170.02, 169.63, 167.20, 167.02, 140.93, 138.47, 134.16, 133.74, 133.17, 131.83, 130.28, 129.26, 128.86, 128.78, 128.16, 128.05, 127.10, 126.50, 84.09, 80.11, 79.01, 75.59, 74.96, 74.07, 71.24, 60.45, 55.74, 53.01, 44.57, 43.06, 42.38, 38.67, 35.99, 30.20, 26.11, 22.79, 21.73, 21.10, 20.81, 15.59, 14.57, 14.26, 6.58, 4.44. LRESIMS m/z Calcd. for C$_{55}$H$_{67}$NO$_{14}$SSi [M—H]$^-$ 1025, found 1025. IR(cm$^-$): 3495.03, 2955.20, 2878.09, 1749.43, 1732.71, 1715.71, 1702.74, 1667.92, 1241.35, 1119.88, 1071.07, 709.56

EXAMPLE 6

2'-O-(tertbutyldimethylsilyl)-7-deoxy-6β-thioacetoxypaclitaxel [10a]

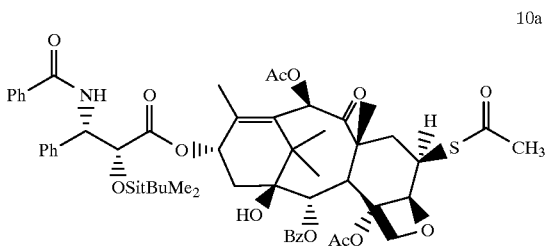

A solution of 2'-tert-butyldimethylsilyl-6-α-trifluoromethanesulfonyl-7-deoxy-paclitaxel (xx) (2.36 g, 2.14 mmoles) in anhydrous DMF (25.0 mL) was cooled to −25° C. using an immersion cooler and treated with potassium thioacetate (501.4 mg, 2.05 mmoles) in anhydrous DMF (10 mL). The temperature increased to −23° C. during the course of the addition. The immersion cooler was turned off, and the mixture was stirred for 5 hrs., as it warmed to ambient temperature. The reaction mixture was poured into water (200 mL) overlaid with ethyl acetate (300 mL). The aqueous phase was extracted with ethyl acetate (250 mL). The combined organic extracts were washed with brine (100 mL), dried over anhydrous Na$_2$SO$_4$, filtered and concentrated in vacuo. Purification by column chromatography on silica eluting with 75%, hexanes/ethyl acetate afforded 1.98 g (90.0%) of compound with formula xx as a white, amorphous powder which exhibited the following physical properties: LRMS (ESI): 1024.4 ((M-1)$^-$, 100%).

$^1$H NMR (CDCl$_3$ 300 MHz)δ: 8.18 (d, 2H), 7.76 (d, 2H), 7.66–7.32 (m, 11H), 7.10 (d, 1H, J=9.0), 6.50 (s, 1H), 6.30 (t, 1H, J=8.6), 5.80–5.73 (m, 2H), 5.01 (d, 1H, J=7.7), 4.70 (d, 1H, J=2.1), 4.51–4.45 (m, 1H) 4.36 (d, 1H, J=8.1), 4.15 (d, 1H, J=8.2), 3.78 (d, 1H, J=7.1), 2.76–0.26(m, 41H, include singlets at 2.61, 2.32, 2.23, 1.97, 1.86, 1.57, 1.04, 0.00, −0.26 3H each and at 0.83 9H) $^{13}$C NMR (CDCl$_3$, 75.469 MHz)δ: 205.11, 197.67, 171.39, 170.12, 169.63, 167.25, 166.96, 140.96, 138.39, 134.20, 133.77, 133.20, 131.86, 130.32, 129.28, 128.90, 128.84, 128.81, 128.05, 127.08, 126.49, 84.19, 80.16, 79.09, 75.64, 75.32, 74.09, 71.20, 55.71, 53.04, 44.55, 43.10, 42.35, 38.70, 36.05, 30.23, 26.15, 25.61, 22.86, 21.80, 20.82, 18.23, 15.73 and 14.66 IR (cm$^{-1}$): 3442.20, 29543.03, 2931.14, 1748.69, 1732.16, 1717.89, 1314.57, 1241.75, 1128.23, 1108.41, 1069.85, 971.04, 838.26, 710.67.

EXAMPLE 7

7-deoxy-6β-thioacetoxypaclitaxel [11]

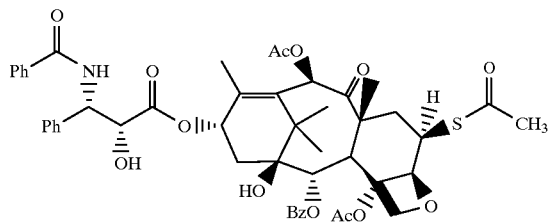

Triethylsilyl ether 10 (0.842 g, 0.82 mmol) was dissolved in acetonitrile (30 mL), cooled to 0° C. and treated with 1M HCl (1.64 mL, 1.64 mmol) for 40 minutes. The reaction mixture was concentrated to a residue under vacuum and purified via radial chromatography using hexanes/ethyl acetrate 1:1 as eluent. The pure fractions were stripped to a residue, dissolved in a minimum amount of methylene chloride and precipitated with hexanes. This suspension was stripped to a solid residue under vacuum to provide the hydroxy thioacetate 11 (0.578 g) in 76% yield.

$^1$H NMR (CDCl$_3$ 300 MHz)δ: 8.13 (d, 2H$_{arom.}$), 7.72 (d, 2H$_{arom.}$), 7.63–7.31 (m, 11H$_{arom.}$), 7.03 (d, 1H, J=9.0, H$_{NH}$), 6.42 (s, 1H, H$_{10}$), 6.19 (t, 1H, J=8.6, H$_{13}$), 5.79 (dd, 1H, J=8.9, 2.4, H$_3$), 5.68 (d, 1H, J=7.0, H$_2$), 4.93 (d, 1H, J=7.5, H$_5$), 4.78 (d, 1H, J=2.4, H$_2'$), 4.40 (m, 1H, H$_6$), 4.30 (d, 1H, J=8.1H$_{20}$), 4.08 (d, 1H, J=8.1, H$_{20}$), 3.73 (d, 1H, J=7.0, H$_3$), 3.63 (br, 1H, $_{OH}$), 2.60 (dd, 1H, J=14.6, 8.8), 2.38 (s, 3H, $_{SAc}$), 2.32 (d, 2H), 2.27 (s, 3H, $_{Ac}$), 2.20 (s, 3H, $_{Ac}$), 1.80 (s, 6H, H$_{18}$+H$_{19}$), 1.73 (dd, 1H, J=14.9, 2.5), 1.25 (br, 1H, $_{OH}$), 1.19 (s, 3H, H$_{16}$), 1.12 (s, 3H, H$_{17}$) $^{13}$C NMR (CDCl$_3$, 75.469 MHz)δ: 204.84, 194.28, 172.63, 170.34, 169.62, 167.16, 167.07, 140.46, 138.09, 133.81, 133.71, 133.50, 132.02, 130.26, 129.24, 129.08, 128.82, 128.76, 128.39, 127.12, 127.08, 84.28, 80.13, 78.86, 75.70, 75.47, 74.13, 73.30, 72.18, 54.98, 53.06, 44.44, 43.02, 41.99, 38.60, 35.87, 30.21, 26.25, 22.47, 21.34, 20.82, 15.86, 14.61 LRESIMS m/z Calcd. for C$_{49}$H$_{53}$NO$_{14}$S [M+H]$^+$ 912, found 912 IR (cm$^{-1}$): 3436.11, 2946.38, 1731.81, 1720.30, 1695.57, 1665.13, 1371.88, 1240.79, 1107.89, 711.43 Elemental calcd. for C$_{49}$H$_{53}$NO$_{14}$S: C, 64.53; H, 5.86; N, 1.54; S, 3.52. Found: C, 64.12; H, 6.13; N, 1.46; S, 3.28.

EXAMPLE 8
2'-O-(triethylsilyl)-7-deoxy-6β-thio-paclitaxel [12]

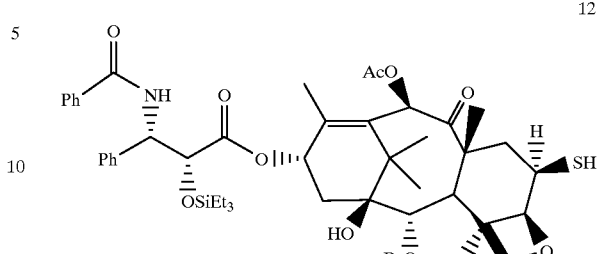

Thioacetate 10 (1.76 g, 1.71 mmol) was dissolved in ethanol (150 mL) and degassed under vacuum with stirring for 5 minutes. Anhydrous ammonia gas was then slowly bubbled into the reaction flask for 1.5 hours. During this time the progress of the reaction was monitored by TLC (hexanes/ethyl acetate 1:1). When no more starting material remained, the excess ammonia was gently stripped off under vacuum. Concentration to a residue followed by radial chromatography (hexanes/ethyl acetate 2:1) provided the free thiol 12 (1.16 g) in 68.9% yield.

$^1$H NMR (CDCl$_3$ 300 MHz)δ: 8.12 (d, 2H, $_{arom.}$), 7.72 (d, 2H, $_{arom.}$) 7.61–7.28 (m, 11H, $_{arom.}$), 7.09 (d, 1H, J=8.9 H$_{NH}$), 6.43 (s, 1H, H$_{10}$), 6.22 (t, 1H, J=8.7, H$_{13}$), 5.71 (m, 2H, H$_3$.+H$_2$), 4.82 (d, 1H, J=5.9, H$_5$), 4.67 (d, 1H, J=2.0, H$_2'$) 4.31 (d, 1H, J=8.0, H$_{20}$) 4.08 (d, 1H, J=8.0, H$_{20}$), 3.73 (d, 1H, J=6.7, H$_3$), 3.60 (m, 1H, H$_6$), 2.81–2.51 (m, 4H, contains H$_{4-Ac}$), 2.39–2.26 (m, 1H), 2.19–2.09 (m, 4H, contains H$_{10-Ac}$), 1.98–1.88 (m, 7H, contains H$_{18}$+H$_{19}$), 1.19 (s, 3H, H$_{16}$), 1.10 (s, 3H, H$_{17}$), 0.94–0.87 (m, 1H), 0.79 (t, 9H), 0.52–0.31 (m, 6H). $^{13}$C NMR (CDCl$_3$, 75.469 MHz)δ: 204.78, 171.56, 170.11, 169.76, 167.11, 167.05, 141.02, 138.49, 134.16, 133.75, 133.45, 131.84, 130.27, 130.13, 129.03, 128.78, 128.75, 128.04, 127.10, 126.51, 86.10, 79.98, 78.82, 75.75, 74.98, 74.86, 73.95, 71.25, 55.74, 53.27, 44.83, 43.14, 42.88, 35.94, 33.80, 26.17, 22.87, 21.84, 20.84, 17.67, 14.58, 6.58, 4.37. LRESIMS m/z Calcd. for C$_{53}$H$_{65}$NO$_{13}$SSi [M+H]+984, found 984. IR (cm$^{-1}$): 3442.01, 2956.12, 1745.88, 1732.46, 1718.19, 1667.90, 1484.36, 1271.54, 1240.63, 1069.86, 970.22, 710.50.

EXAMPLE 9
2'-O-(tertbutyldimethylsilyl)-7-deoxy-6b-thiopaclitaxel (12a)

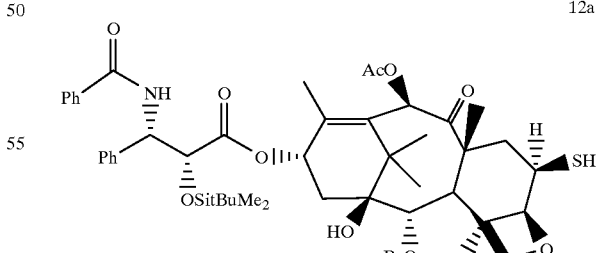

Thioacetate (6.55 g, 6.38 mmol) was dissolved in ethanol (351 mL) and degassed under house vacuum with stirring for 20 minutes, then backfilled with nitrogen. Anhydrous ammonia gas was then slowly bubbled into the reaction flask for 1 hour. The excess ammonia was gently stripped off under vacuum. Concentration to a residue followed by chromatography on silica gel (hexanes/ethyl acetate 4:1, 3:1) to provide 5.65 g of the free thiol as a white solid in 91% yield $^{1}$H NMR (CDCl$_{3}$ 300 MHz)δ: 8.19 (d, 2H), 7.79 (d, 2H) 7.76–7.33 (m, 11H), 7.11 (d, 1H, J=9.0), 6.50 (s, 1H), 6.30 (t, 1H, J=8.7), 5.79 (m, 1H, J=6.9), 4.90 (d, 1H, ,J=5.9), 4.70 (d, 1H, J=2.1) 4.38 (d, 1H, J=8.0) 4.16 (d, 1H, J=7.4), 3.79 (d, 1H, J=6.7), 3.72–3.62 (m, 1H), 2.62–0.29 (m, 39H, include singlets at 2.62, 2.26, 1.95, 1.94, 1.26, 1.16, 0.00, −0.29, 3H each and at 0.84 9H) $^{13}$C NMR (CDCl$_{3}$, 75.469 MHz)δ: 204.79, 171.41, 170.22, 169.78, 167.16, 167.01, 141.03, 138.38, 134.1.8, 133.80, 133.47, 131.90, 130.31, 129.26, 128.88, 128.84, 128.06, 127.09, 126.49, 86.14, 80.02, 78.88, 75.81, 75.33, 74.90, 73.95, 71.20, 55.71, 53.31, 44.86, 43.16, 42.92, 35.97, 33.84, 26.20, 25.61, 22.95, 21.89, 20.86, 18.23, 17.72, 14.69 LRESIMS m/z Calcd. for C$_{53}$H$_{65}$NO$_{13}$SSi [M+H]$^{-}$ 983, found 983. IR (cm$^{-1}$): 3442.10, 2953.51, 2931.34, 1746.52, 1732.37, 1718.10, 1668.17, 1484.54, 1371.86, 1270.11, 1241.06, 1127.17, 1108.70, 1070.00, 970.46, 710.62

EXAMPLE 10

7-deoxy-6β-thio-paclitaxel [13]

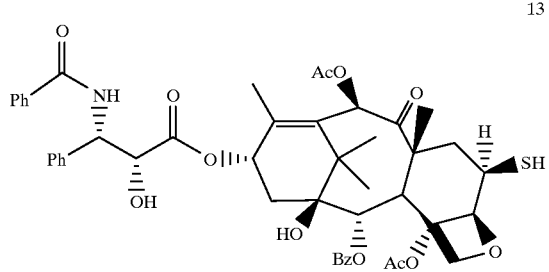

Triethylsilyl ether 12 (0.277 g, 0.28 mmol) was dissolved in acetonitrile (5 mL), degassed under vacuum and cooled to 0° C. 1M HCl (0.56 mL, 0.56 mmol) was added and the reaction was stirred for 40 minutes. Concentration followed by chromatography over silica gel (hexanes/ethyl acetate 1:1) provided the product 13 as a white solid (172 mg, 71%).

$^{1}$H NMR (CDCl$_{3}$ 300 MHz)δ: 8.06 (d, 2H, $_{arom.}$), 7.68 (d, 2H, $_{arom.}$) 7.58–7.24 (m, 11H, $_{arom.}$), 7.02 (d, 1H, J=8.8, H$_{NH}$), 6.34 (s, 1H, H$_{10}$), 6.10 (t, 1H, J=8.6, H$_{13}$), 5.73 (d, 1H, J=8.3, H$_{3'}$), 5.66 (d, 1H, J=6.6, H$_{2}$), 4.75 (d, 1H, J=5.4, H$_{5}$), 4.72 (s, 1H, H$_{2'}$), 4.25 (d, 1H, J=7.9, H$_{20}$), 4.02 (d, 1H, J=8.0, H$_{20}$), 3.67 (d, 1H, J=6.5, H$_{3}$), 3.50 (m, 1H, H$_{6}$), 2.39 (dd, 1H, J=15.1, 9.1), 2.31 (s, 3H, $_{4Ac}$), 2.23 (s, 1H), 2.21 (s, 1H), 2.15 (s, 3H, $_{10Ac}$), 1.89–1.74 (m, 7H, contains H$_{18}$), 1.66 (s, 3H, H$_{19}$), 1.13 (s, 3H, H$_{16}$), 1.05 (s, 3H, H$_{17}$). $^{13}$C NMR (CDCl$_{3}$, 75.469 MHz)δ: 204.39, 172.34, 170.55, 169.73, 167.10, 166.96, 140.45, 138.10, 133.88, 133.73, 132.02, 130.22, 129.19, 129.04, 128.80, 128.77, 128.37, 127.13, 127.11, 86.47, 80.04, 78.62, 75.59, 75.00, 73.97, 73.41, 72.00, 54.93, 53.33, 44.39, 43.07, 42.71, 35.80, 33.75, 26.29, 22.52, 21.31, 20.85, 18.03, 14.66. LRESIMS m/z Calcd. for C$_{47}$H$_{51}$NO$_{13}$S [M+H]$^{+'}$ 870, found 870. IR (cm$^{-1}$): 3424.76, 1732.65, 1719.50, 1659.96, 1485.84, 1239.78, 1107.76, 1070.11, 969.58, 711.14

EXAMPLE 11

2'-O-(triethylsilyl)-7-deoxy-6β-(2-hydroxyethyl)thio-paclitaxel [14]

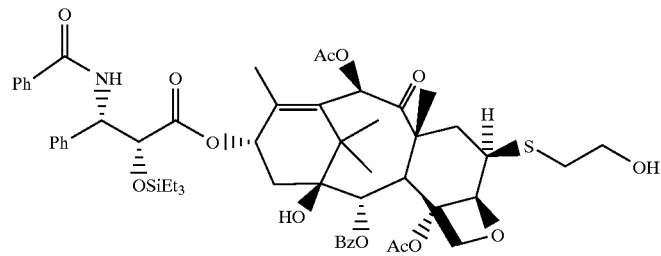

Thiol 12 (1.40 g, 1.42 mmol) was dissolved in benzene (30 mL) and degassed under house vacuum for 20 minutes, then backfilled with nitrogen. This solution was then saturated with ethylene oxide gas via a subsurface feed tube, and treated with DBU (21.7 uL, 0.14 mmol) for 2 hours. The reaction mixture was then concentrated to a residue and chromatographed over silica gel (hexanes/ethyl acetate 1.5:1) to provide the hydroxyethyl thioether 14 (1.18 g, 80.8%) as a white solid.

$^{1}$H NMR (CDCl$_{3}$ 300 MHZ)δ: 8.14 (d, 2H, H$_{arom.}$), 7.74 (d, 2H, H$_{arom.}$) 7.64–7.30 (m, 11H, H$_{arom.}$), 7.11 (d, 1H, J=8.9, H$_{NH}$), 6.45 (s, 1H, H$_{10}$), 6.24 (t, 1H, J=8.8, H$_{13}$), 5.72 (m, 2H, H$_{2}$+H$_{3'}$), 4.94 (d, 1H, J=6.4, H$_{5}$), 4.69 (d, 1H, J=2.0, H$_{2'}$), 4.36 (d, 1H, J=8.0, H$_{20}$), 4.14 (d, 1H, J=8.0, H$_{20}$), 3.74 (d, 1H, J=6.8, H$_{3}$), 3.65 (m, 2H), 3.56 (m, 1H, H$_{6}$), 2.67–2.58 (m, 2H), 2.54 (s, 3H, H$_{4Ac}$), 2.51–2.34 (m, 2H), 2.22 (s, 3H, H$_{10Ac}$), 2.19–2.04 (m, 2H), 1.90 (s, 3H, H$_{18}$), 1.89 (s, 3H, H$_{19}$), 1.22 (s, 3H, H$_{16}$), 1.12 (s, 3H, H$_{17}$), 0.81 (t, 9H), 0.54–0.34 (m, 6H). $^{13}$C NMR (CDCl$_{3}$, 75.469 MHz)δ: 205.00, 171.54, 170.20, 169.87, 167.12, 167.04, 141.03, 138.47, 134.15, 133.76, 133.44, 131.84, 130.27, 129.24, 128.84, 128.78, 128.76, 128.04, 127.09, 126.50, 85.45, 80.30, 78.90, 75.74, 75.57, 74.96, 74.14, 71.25, 61.39, 55.73, 52.89, 43.52, 43.13, 41.63, 40.68, 35.95, 35.72, 26.18, 22.88, 21.88, 20.86, 17.07, 14.54, 6.57, 4.43. LRESIMS m/z Calcd. for C$_{55}$H$_{69}$NO$_{14}$SSi [M+H]$^{+}$ 1027, found 1027. IR (cm$^{-1}$): 3441.09, 2955.74, 2877.85, 1747.01, 1731.81, 1716.67, 1667.63, 1484.78, 1242.11, 1108.45, 970.12, 711.01. Elemental calcd. for C$_{55}$H$_{69}$NO$_{14}$SSi: C, 64.24; H, 6.76; N, 1.36; S, 3.12. Found: C, 64.57; H, 7.16; N, 1.31; S, 3.07.

EXAMPLE 12

7-deoxy-6β-(2-hydroxyethyl)thio-paclitaxel [15]

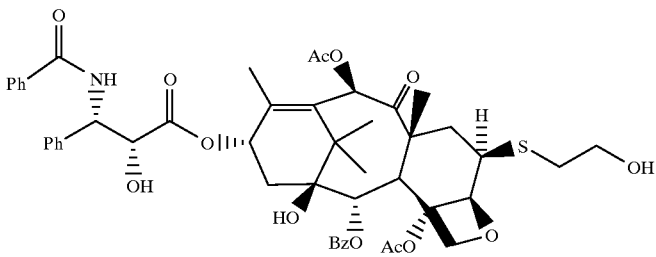

Silyl ether 14 (1.11 g, 1.08 mmol) was dissolved in acetonitrile (50 mL), cooled to 0° C. and treated with 1M HCl (2.16 mL, 2.16 mmol) for 5 minutes. The reaction mixture was stripped to a residue under vacuum, dissolved in acetonitrile and stripped to a residue again. This residue was taken up in a minimal amount of $CH_2Cl_2$ and passed through a short plug of silica gel (hexanes/ethyl acetate 1:3) to provide the alcohol 15 (0.685 g, 69%) as a white solid.

$^1$H NMR ($CDCl_3$ 300 MHz)δ: 8.11 (d, 2H, $H_{arom.}$), 7.72 (d, 2H, $H_{arom.}$) 7.63–7.30 (m, 11H, $H_{arom.}$), 7.08 (d, 1H, J=8.9, $H_{NH}$), 6.39 (s, 1H, $H_{10}$), 6.16 (t, 1H, J=8.5, $H_{13}$), 5.77 (dd, 1H, $H_3$), 5.70 (d, 1H, J=6.7, $H_2$), 4.90 (d, 1H, J=5.9, $H_5$), 4.77 (d, 1H, J=2.5, $H_{2'}$), 4.31 (d, 1H, J=8.1, $H_{20}$), 4.10 (d, 1H, J=8.3, $H_{20}$), 3.71 (d, 1H, J=6.7, $H_3$), 3.65 (m, 2H), 3.52 (br, 1H, $H_6$), 2.71–2.41 (br, 3H), 2.36 (s, 3H, $H_{4Ac}$), 2.28 (d, 2H, J=8.9), 2.20 (s, 3H, $H_{10Ac}$), 1.85 (s, 3H, $H_{18}$), 1.74 (s, 3H, $H_{19}$), 1.29–1.22 (m, 2H), 1.19 (s, 3H, $H_{16}$), 1.11 (s, 3H, $H_{17}$) $^{13}$C NMR ($CDCl_3$, 75.469 MHz)δ: 204.68, 172.47, 170.53, 169.88, 167.08, 140.53, 138.09, 133.83, 133.72, 132.02, 130.23, 129.21, 129.04, 128.79, 128.75, 128.37, 127.11, 85.67, 80.31, 78.70, 75.66, 75.59, 74.19, 73.35, 72.08, 61.50, 54.99, 52.93, 43.30, 43.07, 41.20, 40.46, 35.82, 35.51, 31.65, 26.29, 22.71, 22.54, 21.41, 20.87, 17.45, 14.62, 14.18. IR LRESIMS m/z Calcd. for $C_{49}H_{55}NO_{14}S$ [M+H]$^+$ 913, found 913. IR (cm$^{-1}$): 3425.97, 2932.16, 1732.38, 1716.61, 1652.17, 1486.96, 1372.16, 1241.40, 1107.79, 1069.54, 969.11, 711.17. Elemental calcd. for $C_{49}H_{55}NO_{14}S$: C, 64.39; H, 6.06; N, 1.53; S, 3.51. Found: C, 64.55; H, 6.49; N, 1.43; S, 3.35.

EXAMPLE 13

2'-O-(triethylsilyl)-7-deoxy-6β-thiocyanato-paclitaxel [16] and 7-deoxy-6β-thiocyanato-paclitaxel [17]

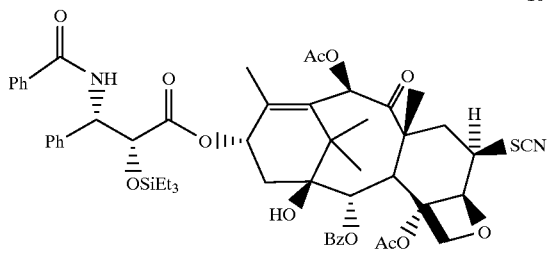

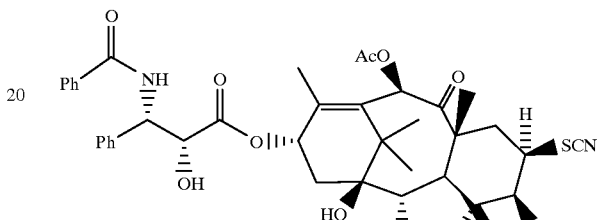

Triflate 7 (1.09 g, 0.99 mmol) and potassium thiocyanate (0.195 g, 2.0 mmol) were dissolved in DMF (10 mL) and heated to 80–100° C. for 5 minutes. The DMF was stripped off under vacuum, and the residue was taken up in a minimum amount of $CH_2Cl_2$. This suspension of products and salts was passed through a plug of silica gel using hexanes/ethyl acetate 2:1 to elute the fast moving product, followed by hexanes/ethyl acetate 1:3 to elute the slower moving product. Separate radial chromatography of each of these materials (hexanes/ethyl acetate 2:1 for the fast moving product and hexanes/ethyl acetate 1:1 for the slow moving spot) provided the 2'-silyl protected thiocyanate 16 (0.341 g, 34%), as well as the 2'-hydroxy thiocyanate 17 (0.392 g, 44%).

Alternate procedure for preparation of 17: Silyl ether 16 (0.63 g, 0.62 mmol) was dissolved in acetonitrile (10 mL), cooled to 0° C. and treated with 1M HCl (1.25 mL, 1.25 mmol) for 30 minutes. The reaction mixture was stripped to a residue under vacuum, dissolved in acetonitrile and stripped to a residue again. This residue was taken up in a minimal amount of $CH_2Cl_2$ and passed through a short plug of silica gel (hexanes/ethyl acetate 2:1–1:1) to provide the alcohol 17 (0.521 g, 94%) as a white solid.

2'-triethylsilyl thiocyanate [16]

$^1$H NMR ($CDCl_3$ 300 MHz)δ: 8.13 (d, 2H, $H_{arom.}$), 7.72 (d, 2H, $H_{arom.}$) 7.63–7.29 (m, 11H, $H_{arom.}$), 7.09 (d, 1H, J=9.0, $H_{NH}$), 6.45 (s, 1H, $H_{10}$), 6.24 (t, 1H, J=8.6, $H_{13}$), 5.70 (m, 2H, $H_3$+$H_2$), 5.02 (d, 1H, J=5.8, $H_5$), 468 (d, 1H, J=2.1, $H_{2'}$), 4.37 (d, 1H, J=8.2, $H_{20}$), 4.21 (dt, 1H, J=9.7, 2.1, $H_6$), 4.15 (d, 1H, J=8.1, $H_{20}$), 3.71 (d, 1H, J=6.9, $H_3$), 2.59 (dd, 1H, J=15.4, 8.4), 2.55 (s, 3H, $H_{4Ac}$), 2.37 (dd, 1H, J=15.4, 9.6), 2.21 (s, 3H, $H_{10Ac}$), 2.18–2.07 (m, 2H), 1.88 (s, 6H, $H_{18}$+$H_{19}$), 1.21 (s, 3H, $H_{16}$), 1.12 (s, 3H, $H_{17}$), 0.79 (t, 9H), 0.63–0.33 (m, 6H). $^{13}$C NMR ($CDCl_3$, 75.469 MHz)δ: 204.26, 171.48, 170.43, 169.60, 167.12, 166.98, 141.08, 138.41, 134.13, 133.89, 133.26, 131.85, 130.28, 129.06, 128.93, 128.81, 128.75, 128.09, 127.09, 126.49, 112.01, 82.78, 79.49, 79.01, 76.11, 75.36, 74.98, 73.75, 71.10, 55.67, 52.84, 45.39, 44.06, 43.03, 40.97, 36.03, 26.08, 22.73, 21.80, 20.79, 16.13, 14.53, 6.58, 4.44. LRESIMS m/z Calcd. for $C_{54}H_{64}N_2O_{13}SSi$ [M–H]⁻ 1008, found 1008. IR (cm⁻¹): 3441.46, 2956.01, 2878.14, 2155.82, 1746.50, 1731.59, 1667.86, 1484.42, 1270.35, 1240.33, 1107.41, 1070.34, 971.27, 710.42

2'-hydroxy thiocyanate [17]

$^1$H NMR (CDCl₃ 300 MHz)δ: 8.12 (d, 2H, $H_{arom.}$), 7.71 (d, 2H, $H_{arom.}$) 7.64–7.32 (m, 11H, $H_{arom.}$), 7.01 (d, 1H, J=8.9, $H_{NH}$), 6.41 (s, 1H, $H_{10}$), 6.19 (t, 1H, J=8.5, $H_{13}$), 5.76 (dd, 1H, J=8.9, 2.5, $H_3$), 5.70 (d, 1H, J=7.0, $H_2$), 4.98 (d, 1H, J=7.3, $H_5$), 4.77 (d, 1H, J=2.5, $H_{2'}$), 4.35 (d, 1H, J=8.2, $H_{20}$), 4.19–4.09 (m, 2H, $H_6$+$H_{20}$), 3.69 (d, 1H, J=6.9, $H_3$), 3.62 (br, 1H, $H_{OH}$), 2.54 (dd, 1H, J=15.4, 8.5), 2.41 (s, 3H, $H_{4Ac}$), 2.35–2.24 (m, 2H), 2.21 (s, 3H, $H_{10Ac}$), 1.87 (s, 3H, $H_{18}$), 1.77 (s, 3H, $H_{19}$), 1.19 (s, 3H, $H_{16}$), 1.12 (s, 3H, $H_{17}$). $^{13}$C NMR (CDCl₃, 75.469 MHz)δ: 204.08, 172.72, 170.66, 169.61, 167.17, 167.07, 140.63, 138.01, 133.93, 133.67, 133.53, 132.06, 130.26, 129.11, 128.88, 128.76, 128.44, 127.13, 127.06, 111.91, 82.85, 79.46, 78.87, 76.14, 75.27, 73.79, 73.27, 72.08, 55.10, 52.87, 45.22, 44.03, 42.99, 40.75, 35.91, 26.18, 22.39, 21.48, 20.80, 16.21, 14.51, 14.26. LRESIMS m/z Calcd. for $C_{48}H_{50}N_2O_{13}S$ [M–H]⁻ 894, found 894. IR (cm⁻¹): 3432.14, 299 0.13, 2155.51, 1728.732, 1661.84, 1270.10, 1239.85, 1070.49, 970.27, 710.95.

EXAMPLE 14

2'-O-(triethylsilyl)-7-deoxy-6β-methyl sulfoxide-paclitaxel 18

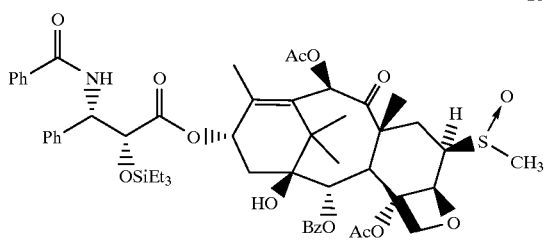

Thiomethyl ether 8 (2.0 9 g, 2.09 mmol) was dissolved in methylene chloride (30 mL), cooled to −40° C. (acetonitrile/dry ice) and treated with m-CPBA (0.36 g, ~2.09 mmol) in small portions over two hours. The reaction was allowed to warm to room temperature then washed with excess satd. NaHCO₃. Concentration followed by MPLC (acetonitrile/ether 1:1) in portions provided the slow eluting sulfoxide 18 (1.62 g, 76%) as a white solid contaminated with a trace of the faster eluting minor diastereomer. Additionally (0.38 g 18%) of the faster eluting minor diastereomer contaminated with a small amount of starting material, and a trace of the slower eluting sulfoxide was also recovered.

$^1$H NMR (CDCl₃ 300 MHz)δ: 8.13 (d, 2H, $H_{arom.}$), 7.73 (d, 2H, $H_{arom.}$) 7.64–7.31 (m, 11H, $H_{arom.}$), 7.10 (d, 1H, J=9.0, $H_{NH}$), 6.48 (s, 1H, $H_{10}$), 6.22 (t, 1H, J=8.7, $H_{13}$), 5.75 (d, 1H, J=6.9, $H_2$), 5.69 (d, 1H, J=8.9, $H_3$), 5.26 (d, 1H, J=6.2, $H_5$), 4.67 (d, 1H, J=2.0, $H_{2'}$), 4.43 (d, 1H, J=8.0, $H_{20}$), 4.22 (d, 1H, J=7.9, $H_{20}$), 3.77 (d, 1H, J=6.8, $H_3$), 3.52 (br, 1H, $H_6$), 2.58 (s, 3H, $H_{CH3S}$), 2.52 (s, 3H, $H_{4Ac}$), 2.43–2.24 (m, 2H), 2.21 (s, 3H, $H_{10Ac}$), 2.18–2.12 (m, 2H), 1.90 (s, 3H, $H_{18}$), 1.89 (s, 3H, $H_{19}$), 1.34–1.24 (m, 2H), 1.21 (s, 3H, $H_{16}$), 1.12 (s, 3H, $H_{17}$) 0.80 (t, 9H), 0.51–0.35 (m, 6H). $^{13}$C NMR (CDCl₃, 75.469 MHz)δ: 204.70, 171.57, 170.26, 169.93, 167.18, 167.04, 141.33, 138.42, 134.15, 133.87, 133.23, 131.86, 130.28, 128.81, 128.68, 128.10, 127.23, 127.10, 126.49, 82.84, 79.70, 78.85, 75.63, 74.96, 73.74, 71.19, 59.69, 55.72, 52.39, 43.05, 42.99, 37.30, 35.99, 34.16, 31.65, 26.08, 22.70, 21.87, 20.82, 16.96, 14.62, 6.58, 4.44. LRESIMS m/z Calcd. for $C_{54}H_{67}NO_{14}SSi$ [M+H]⁺ 1013, found 1013. IR (cm⁻¹): 3440.47, 2955.72, 1732.05, 1667.24, 1484.18, 1371.92, 1239.95, 1070.56,970.24, 710.87 Elemental calcd. for: $C_{54}H_{67}NO_{14}SSi$: C, 63.95; H, 6.66; N, 1.38; S, 3.16. Found: C, 63.88; H, 6.89; N, 1.26; S, 3.06.

EXAMPLE 15

7-deoxy-6β-methyl sulfoxide-paclitaxel diastereomers 19 and 19a

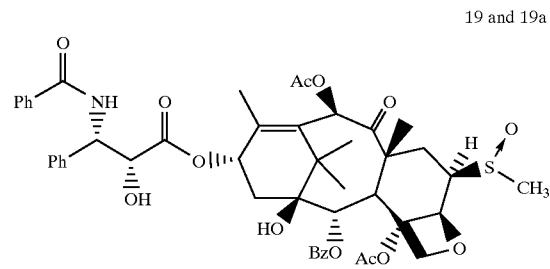

19 and 19a

Silyl ether 18 (1.0 g, 0.99 mmol) was dissolved in acetonitrile (40 mL), cooled to 0° C. and treated with 1M HCl (1.97 mL, 1.97 mmol) for 10 minutes. The reaction mixture was stripped to a residue under vacuum, dissolved in acetonitrile and stripped to a residue again. This residue was chromatographed over silica gel (acetonitrile/ether 1:1) to provide the alcohol 19 (0.363 g, 41%) as a white solid. Mixed fractions containing a small amount of the faster eluting minor diastereomer (19a) amounted to (0.438 g 49%).

$^1$H NMR (CDCl₃ 300 MHz)δ: 8.13 (d, 2H, $H_{arom.}$), 7.77 (d, 2H, $H_{arom.}$) 7.73–7.30 (m, 11H, $H_{arom.}$), 7.23 (d, 1H, J=9.0, $H_{NH}$), 6.45 (s, 1H, $H_{10}$), 6.17 (t, 1H, J=8.6, $H_{13}$), 5.78–5.73 (m, 2H, $H_2$+$H_{3'}$), 5.22 (d, 1H, J=6.2, $H_5$), 4.75 (dd, 1H, J=5.9, 2.7, $H_{2'}$), 4.37 (d, 1H, J=8.1, $H_{20}$), 4.18 (d, 1H, J=8.0, $H_{20}$), 4.01 (d, 1H, J=6.1, $H_{OH}$) 3.74 (d, 1H, J=6.7, $H_3$), 3.51 (br, 1H, $H_6$), 2.53 (s, 3H, $H_{CH3S}$), 2.36 (s, 3H, $H_{4Ac}$), 2.32–2.27 (m, 2H), 2.22 (s, 3H, $H_{10Ac}$), 1.94 (s, 3H, $H_{18}$), 1.84 (s, 3H, $H_{19}$), 1.41–1.24 (m, 4H), 1.20 (s, 3H, $H_{16}$), 1.12 (s, 3H, $H_{17}$). $^{13}$C NMR (CDCl₃, 75.469 Mhz)δ: 204.51, 172.69, 170.50, 169.96, 167.22, 167.10, 141.01, 138.24, 133.92, 133.81, 133.39, 131.94, 130.26, 129.12, 129.00, 128.87, 128.69, 128.28, 127.23, 127.11, 82.75, 79.60, 78.70, 75.48, 73.80, 73.35, 71.82, 59.41, 55.17, 52.43, 43.16, 42.98, 37.00, 35.87, 33.93, 31.65, 26.16, 22.72, 22.35, 20.84, 16.94, 14.62. LRESIMS m/z Calcd. for $C_{48}H_{53}NO_{14}S$ [M–H]⁻ 899, found 899. IR (cm⁻¹): 3424.70, 2952.86, 1731.93, 1662.46, 1486.09, 1372.19, 1238.92, 1107.55, 1025.47, 711.09 Elemental calcd. for: $C_{48}H_{53}NO_{14}S$: C, 64.06; H, 5.94; N, 1.56; S, 3.56. Found: C, 64.12; H, 6.04; N, 1.44; S, 3.41.

EXAMPLE 16

2'-O-(triethylsilyl)-7-deoxy-6β-methyl sulfone-paclitaxel [20]

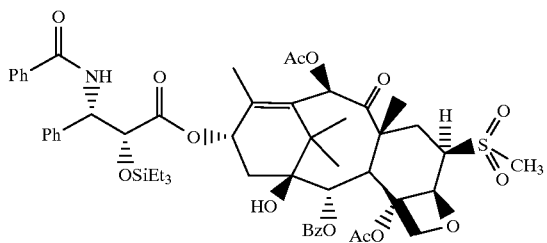

20

Thiomethyl ether 8 (1.50 g, 1.50 mmol) was dissolved in $CH_2Cl_2$ (50 mL), cooled to 0° C. and treated with m-cpba (1.09 g, @ 50%, 3.15 mmol) in portions over 30 minutes. The reaction was allowed to warm to 25° C. and stirred for an additional 30 minutes. The mixture was washed with saturated $NaHCO_3$, brine, dried over $MgSO_4$, and concentrated to a residue. This residue was dissolved in a minimal amount of $CH_2Cl_2$ and passed through a short plug of silica gel using hexanes/ethyl acetate 2:1 as eluent. Concentration of the clean fractions provided the sulfone 20 (1.396 g 90.2%) as a white solid.

$^1$H NMR ($CDCl_3$ 300 MHz)δ: 8.11 (d, 2H, $H_{arom.}$), 7.74 (d, 2H, $H_{arom.}$) 7.64–7.29 (m, 11H, $H_{arom.}$), 7.10 (d, 1H, J=9.0, $H_{NH}$), 6.52 (s, 1H, $H_{10}$), 6.22 (t, 1H, J=8.7, $H_{13}$), 5.79 (d, 1H, J=6.5, $H_2$), 5.70 (dd, 1H, J=90, 1.5, $H_3$·), 5.31 (d, 1H, J=4.1, $H_5$), 4.69 (d, 1H, J=2.0, $H_2$·), 4.42 (d, 1H, J=7.8, $H_{20}$), 4.21 (d, 1H, J=7.8, $H_{20}$), 3.88 (m, 1H, $H_6$), 3.81 (d, 1H, J=6.3, $H_3$), 2.86 (s, 3H, $H_{CH3S}$), 2.53 (s, 3H, $H_{4Ac}$), 2.42–2.29 (m, 2H), 2.21 (s, 3H, $H_{10Ac}$), 2.19–2.03 (m, 2H), 1.99 (s, 3H, $H_{18}$), 1.90 (s, 3H, $H_{19}$), 1.22 (s, 3H $H_{16}$), 1.14 (s, 3H, $H_{17}$) 0.81 (t, 9H), 0.54–0.33 (m, 6H). $^{13}$C NMR ($CDCl_3$, 75.469 MHz)δ: 203.82, 171.61, 170.14, 169.57, 167.15, 166.99, 141.48, 138.38, 134.17, 133.92, 133.28, 131.88, 130.23, 129.01, 128.89, 128.81, 128.78, 128.08, 127.09, 126.49, 82.41, 79.63, 78.50, 75.63, 74.89, 73.56, 71.09, 59.08, 55.71, 52.08, 43.13, 41.79, 39.60, 35.88, 32.83, 26.08, 22.75, 21.82, 20.76, 18.96, 14.71, 14.18, 6.58, 4.44. LRESIMS m/z Calcd. for $C_{54}H_{67}NO_{15}SSi$ $[M+H]^+$ 1029, found 1029. IR (cm$^{-1}$): 3511.73, 3440.87, 295604, 1722.25, 1666.84, 1484.52, 1271.15, 1239.88, 1124.97, 968.97, 711.52 Elemental calcd. for $C_{54}H_{67}NO_{15}SSi$: C, 62.95; H, 6.55; N, 1.36; S, 3.11. Found: C, 63.16; H, 6.75; N, 1.31; S, 3.11.

EXAMPLE 17

7-deoxy6β-methyl sulfone-paclitaxel [21]

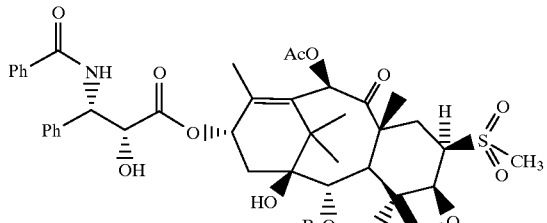

21

Silyl ether sulfone 20 (1.21 g, 1.17 mmol) was dissolved in acetonitrile (30 mL), cooled to 0° C. and treated with 1M HCl (2.35 mL, 2.35 mmol) for 35 minutes. The reaction mixture was stripped to a residue under vacuum, disolved in acetonitrile (60 mL) and stripped to a residue again. This residue was taken up in a minimal amount of $CH_2Cl_2$ and passed through a short plug of silica gel (hexanes/ethyl acetate 1:1–1:2) to provide the hydroxy sulfone 21 (0.975 g, 91%) as a white solid.

$^1$H NMR ($CDCl_3$ 300 MHz)δ: 8.08 (d, 2H, $H_{arom.}$), 7.73 (d, 2H, $H_{arom.}$) 7.64–7.31 (m, 11H, $H_{arom.}$), 7.16 (d, 1H, J=8.9, $H_{NH}$), 6.45 (s, 1H, $H_{10}$), 6.22 (t, 1H, J=8.5, $H_{13}$), 5.77 (s, 1H, $H_3$·), 5.75 (s, 1H, $H_2$), 5.29 (s, 1H, $H_5$), 4.78 (s, 1H, $H_2$·), 4.38 (d, 1H, J=7.9, $H_{20}$), 4.17 (d, 1H, J=7.9, $H_{20}$), 3.86–3.80 (m, 2H, H6+$H_{OH}$), 3.76 (d, 1H, J=6.2, $H_3$), 2.81 (s, 3H, $H_{CH3S}$), 2.36 (s, 3H, $H_{4Ac}$), 2.33–2.22 (m, 2H), 2.19 (s, 3H, $H_{10Ac}$), 2.08–2.00 (m, 2H), 1.95 (s, 3H, $H_{18}$), 1.72 (s, 3H, $H_{19}$), 1.18 (s, 3H, $H_{16}$), 1.11 (s, 3H, $H_{17}$). $^{13}$C NMR ($CDCl_3$, 75.469 MHz)δ: 203.57, 172.37, 170.69, 169.64, 167.16, 166.91, 141.00, 138.17, 133.98, 133.74, 133.56, 132.02, 130.19, 129.01, 128.85, 128.76, 128.31, 127.14, 127.12, 82.30, 79.64, 78.30, 77.20, 75.39, 73.63, 73.36, 71.72, 59.02, 55.04, 52.13, 43.03, 41.92, 39.53, 35.77, 32.54, 26.17, 22.36, 21.34, 20.77, 18.94, 14.76. LRESIMS m/z Calcd. for $C_{48}H_{53}NO_{15}S$ $[M+H]^+$ 915, found 915. IR (cm$^{-1}$): 3440.07, 2934.55, 1733.69, 1722.20, 1661.98, 1486.49, 1312.56, 1239.34, 1071.66, 967.83, 711.97

EXAMPLE 18

7-deoxy-6b-thiomethylbaccatin (22)

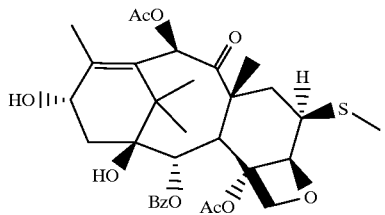

22

7-deoxy-6b-thiomethylpaclitaxel 8 (2.740 g, 3.010 mmol) was dissolved in methylene chloride (24 mL), cooled to 0° C. under nitrogen. Tetrabutyl ammonia borohydride (1.595 g, 6.199 mmol) was added in one portion. The reaction mixture was then warmed up to room temperature and kept stirring for 6.5 hours. The reaction mixture was cooled to 0° C., 24.3 mL of 1M acetic acid was then added. After the foam stopped, diluted with EtOAc, washed with $NaHCO_3$, water and brine. The solution was dried over $MgSO_4$, filtered and concentrated. The residue was chromatographed over silica gel (hexanes/ethyl acetate 3:1, 1:1, 1:1.5). The pure fractions were combined together and stripped to a residue, dissolved in a minimal amount of methylene chloride and precipitated with hexane. This suspension was stripped to a solid residue under vacuum to provide the baccatin 22 (1.693 g) as a white solid in 89% yield.

$^1$H-NMR ($CDCL_3$, 300.133 MHz) δ: 8.11 (d, 2H, J=7.0), 7.63–7.45 (m, 3H), 5.68(d, 1H, J=6.8), 4.98 (d, 1H, J=6.4), 4.90–4.80 (m, 1H), 4.32(d, 1H J=8.0), 4.07 (d, 1H, J=8.1), 3.83 (d, 1H, J=6.7), 3.45–3.39 (m, 1H), 2.45–1.08 (m, 27H, include singlets at 2.29, 2.22, 2.07, 2.05, 1.89, 1.10, 1.08, 3H each) $^{13}$C-NMR ($CDCL_3$, 75.469 MHz)δ: 205.22, 171.03, 169.84, 167.23, 144.54, 133.75, 132.52, 130.14, 129.42, 128.69, 85.23, 80.31, 78.83, 75.63, 75.56, 74.66, 67.95, 53.29, 43.91, 42.67, 41.97, 40.15, 38.81, 26.36, 22.72, 22.57, 20.94, 20.60, 16.72, 15.17 LRESIMS m/z Calcd. for C32H40O10S $[M+H]^+$ 616, found 616 IR (cm$^{-1}$): 3468.95, 2929.54, 1712.12, 1372.52, 1237.60, 1071.26, 710.72

EXAMPLE 19

2'-O-(triethylsilyl)-3'-NH-Boc-7-deoxy-6b-thiomethylpaclitaxel (23)

39

23

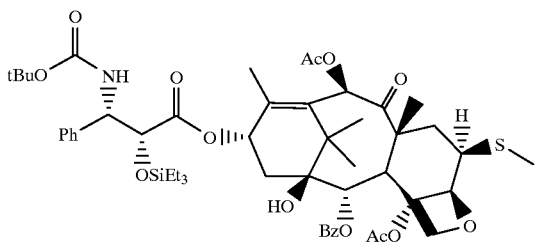

7-deoxy-6b-thiomethylbaccatin 22 (0.70 g, 1.135 mmol) was dissolved in tetrahydrofuran (28 mL), cooled to −40° C. and treated with lithium bis(trimethylsilyl)amide (1.7 mL, 1.702 mmol) for 15 minutes. A solution of (3R, 4S)-1-t-butoxycarbonyl-4-phenyl-3-triethylsilyloxy-2-azetidinone (0.857 g, 2.27 mmol) in THF (2.3 mL) was then added. After stirring for 15 minutes at −40° C., the reaction mixture was warmed up to 0° C. and allowed to stir overnight. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 4:1, 3:1) to provide 1.043 g of the desired product 23 as a white powder in 92% yield.

$^1$H-NMR (CDCL$_3$, 300.133 MHz) δ: 8.13 (d, 2H, J=7.1), 7.62–7.27 (m, 8H), 6.49 (s, 1H), 6.26 (t, 1H, J=8.8), 5.74 (d, 2H, J=6.9), 5.46 (d, 1H, J=9.6), 5.27 (d, 1H, J=9.3), 4.99 (d, 1H, J=6.4), 4.53(d, 1H, J=2.0), 4.33(d, 1H, J=8.0), 4.09 (d, 1H, J=8.0), 3.80 (d, 1H, J=6.8), 3.45–3.39 (m, 1H), 2.52–0.25 (m, 50H, include singlets at 2.51, 2.22, 2.08, 1.90, 1.89, 1.25, 1.14, 3H each, at 1.29, 9H and triplet at 0.80, 9H) $^{13}$C-NMR (CDCL$_3$, 75.469 MHz) δ: 205.06, 171.62, 170.09, 169.80, 167.27, 155.26, 141.29, 133.70, 133.19, 130.26, 129.27, 128.77, 128.61, 127.77, 126.47, 85.33, 80.37, 79.94, 79.06, 75.87, 75.52, 75.31, 73.96, 71.16, 53.06, 43.49, 43.15, 41.89, 40.40, 35.68, 31.65, 28.21, 26.08, 22.84, 22.71, 21.84, 20.86, 16.86, 15.02, 14.51, 6.55, 4.33 LRESIMS m/z Calcd. for C52H71NO14SSi [M+H]$^+$ 993, found 993 IR (cm$^{-1}$): 3446.18, 2957.23, 1732.32, 1715.97, 1494.56, 1369.48, 1271.31, 1242.18, 1164.38, 1110.84, 1069.72, 710.30

EXAMPLE 20
3'-NH-Boc-7-deoxy-6b-thiomethylpaclitaxel (24)

24

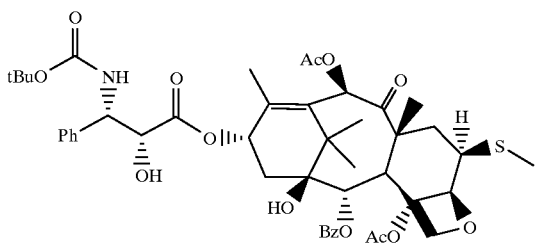

The triethylsilyl ether 23 (1.01 g, 1.016 mmol) was dissolved in acetonitrile (12 mL), cooled to 0° C. and treated with 1M HCl (2.03 mL, 2.032 mmol) for 1 hour. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 3:1, 2:1, 1:1). The pure fractions were combined together and stripped to a residue, dissolved in a minimal amount of methylene chloride and precipitated with hexane. This suspension was stripped to a solid residue under vacuum to provide the thiomethyl ether 24 (0.779 g) as a white solid in 87% yield.

$^1$H-NMR (CDCL$_3$, 300.133 MHz) δ: 8.11 (d, 2H, J=7.3), 7.64–7.28 (m, 8H), 6.47 (s, 1H), 6.18 (t, 1H, J=8.6), 5.73 (d, 1H, J=6.7), 5.39 (d, 1H, J=9.5), 5.25 (d, 1H, 9.1), 4.96 (d, 1H, J=5.9), 4.61 (bs, 1H,), 4.32(d, 1H, J=8.0), 4.08 (d, 1H, J=8.0), 3.75 (d, 1H, J=6.6), 3.42–3.35 (m, 2H), 2.44–1.14 (m, 35H, include singlets at 2.36, 2.23, 2.07, 1.89, 1.82, 1.22, 1.14, 3H each and 1.33 9H) $^{13}$C-NMR (CDCL$_3$, 75.469 MHz) δ: 204.72, 172.65, 170.33, 169.75, 1.67.22, 155.36, 140.62, 138.47, 133.79, 130.21, 129.21, 128,89, 128.75, 128.12, 126.82, 85.48, 80.42, 80.28, 78.77, 75.83, 75.68, 75.62, 74.00, 73.74, 72.16, 56.17, 53.10, 43.28, 43.11, 41.60, 39.97, 35.60, 31.63, 28.25, 26.18, 22.53, 21.38, 20.86, 17.23, 14.86 and 14.63 LRESIMS m/z Calcd. for C46H57NO14S [M+H]$^+$ 879, found 879 IR (cm$^{-1}$): 3446.08, 2979.41, 1735.61, 1715.79, 1370.28, 1241.55, 1168.26, 1107.14, 1069.88, 710.38

EXAMPLE 21
3'-NH-Boc-7-deoxy-6b-methylsulfoxidepaclitaxel (25 and 26)

25 and 26

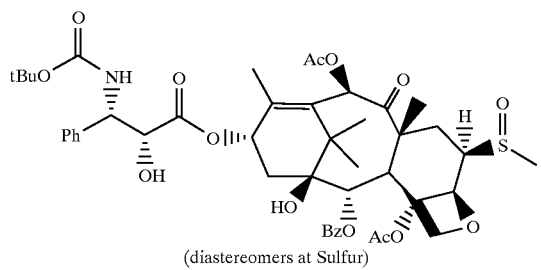

(diastereomers at Sulfur)

A solution of 3-chloroperoxybenzoic acid (0.136 g, 0.393 mmol) in methylene chloride (2 mL) at 25° C. was added dropwise via a syringe to a solution of 3'-NH-Boc-7-deoxy-6b-methylsulfidepaclitaxel 24 (0.346 g, 0.393 mmol) in methylene chloride (5 mL) at −78° C. over 2 minutes. The reaction mixture was stirred at −78° C. for 5 minutes and then warmed up to −15° C. TLC shows the reaction finished in 20 minutes. The reaction was quenched with DMSO (2 mL) and stirred for 5 minutes at −15° C. The reaction mixture was warmed up and diluted with EtOAc, washed with NaHCO$_3$, water and brine. The solution was dried over MgSO$_4$, filtered and concentrated. The residue was chromatographed over silica gel (methylene chloride/acetonitrile 10:1, 10:2, 10:3) to provide the pure minor sulfoxide 25 (8 mg, 2%) as a white solid. Mixed fractions containing a small amount of slower eluting major sulfoxide amounted to (32 mg, 9%), the major sulfoxide containing some of the minor (46 mg, 13%) and the pure slower eluting major sulfoxide 26 (119 mg, 34%)

minor:

$^1$H-NMR (CDCL$_3$, 300.133 MHz) δ: 8.10 (d, 2H, J=7.3), 7.63–7.25 (m, 8H), 6.47 (s, 1H), 6.20 (t, 1H, J=8.9), 5.71 (d, 1H, J=7.2), 5.45 (d, 1H, J=9.5), 5.26–5.12 (m, 2H), 4.61 (bs, 1H), 4.32 (d, 1H, J=8.3), 4.14 (d, 1H, J=8.2), 3.74 (d, 1H, J=7.0), 3.51 (bs, 1H), 3.25 (m, 1H), 2.58–1.15 (m, 35H, include singlets at 2.58, 2.40, 2.20, 1.90, 1.85, 1.23, 1.15, 3H each and 1.32, 9H) $^{13}$C-NMR (CDCL$_3$, 75.469 MHz) δ: 204.38, 170.54, 169.48, 167.33, 140.75, 134.00, 133.63, 130.41, 129.10, 128.99, 128.30, 126.94, 82.68, 80.72, 80.48, 79.17, 75.56, 73.97, 72.38, 62.15, 52.98, 44.83, 43.24, 38.66, 35.88, 33.60, 28.40, 26.27, 22.66, 21.62, 20.98, 15.58, 14.65 LRESIMS m/z Calcd. for C46H57NO15S [M–H]⁻ 895, found 895
major:
¹H-NMR (CDCL₃, 300.133 MHz) δ: 8.10 (d, 2H, J=7.3), 7.64–7.28 (m, 8H), 6.47 (s, 1H), 6.18 (t, 1H, J=8.6), 5.74 (d, 1H, J=6.8), 5.42 (d, 1H, J=9.2), 5.28–5.23 (m, 2H), 4.59 (bs, 1H), 4.41(d, 1H, J=8.0), 4.16 (d, 1H, J=8.1), 3.76 (d, 1H, J=6.6), 3.54–3.48 (m, 2H), 2.56–1.13 (m, 35H, include singlets at 2.56, 2.35, 2.22, 1.89, 1.83, 1.23, 1.13, 3H each and 1.32, 9H) ¹³C-NMR (CDCL₃, 75.469 MHz) δ: 204.66, 170.57, 170.13, 167.41, 141.35, 134.12, 133.50, 130.40, 129.21, 129.10, 129.03, 12832, 126.99, 82.94, 80.44, 79.83, 78.94, 75.66, 73.97, 72.23, 59.58, 52.64, 43.33, 43.20, 37.38, 35.84, 34.05, 28.42, 26.26, 22.50, 21.67, 21.01, 17.01, 14.84 LRESIMS m/z Calcd. for C46H57NO15S [M–H]⁻ 895, found 895 IR (cm⁻¹): 3441.71, 2979.89, 1731.97, 1716.10, 1370.03, 1272.20, 1240.27, 1169.47, 1107.78, 1071.34, 1025.53, 710.95

EXAMPLE 22
2'-O-Ctriethylsilyl)-3'-NH-ethylcarbonate-7-deoxy-6b-thiomethylpaclitaxel (27)

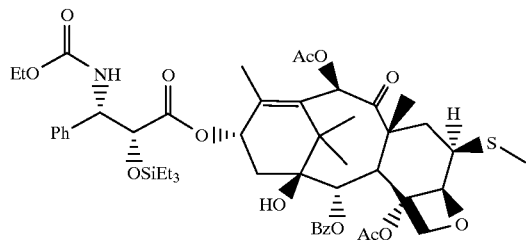

27

7-deoxy-6b-thiomethylbaccatin 22 (0.60 g, 0.973 mmol) was dissolved in tetrahydrofuran (24 mL), cooled to –40° C. and treated with lithium bis(trimethylsilyl)amide (1.5 mL, 1.459 mmol) for 15 minutes. A solution of (3R, 4S)-1-ethylcarbonyl-4-phenyl-3-triethylsilyloxy-2-azetidione (0.683 g, 1.946 mmol) in THF (2 mL) was then added. After stirring for 15 minutes at –40° C., the reaction mixture was warmed up to 0° C. and allowed to stir overnight. The reaction mixture was diluted with EtOAc, washed with NaHCO₃, water and brine. The solution was dried over MgSO₄, filtered and concentrated. The residue was chromatographed over silica gel (hexanes/ethyl acetate 4:1, 3:1, 2:1) to provide 0.743 g of the desired product 27 as a white powder in 79% yield.
¹H-NMR (CDCL₃, 300.133 MHz) δ: 8.13 (d, 2H, J=7.1), 7.62–7.25 (m, 8H), 6.49 (s, 1H), 6.28 (t, 1H, J=8.6), 5.74 (d, 2H, J=7.0), 5.60 (d, 1H, J=9.4), 5.27 (d, 1H, J=7.8), 4.98 (d, 1H, J=6.5), 4.55(d, 1H, J=2.3), 4.33(d, 1H, J=8.0), 4.09 (d, 1H, J=8.0), 3.97 (d, 2H, J=7.1), 3.75 (d, 1H, J=6.8), 3.45–3.38 (m, 1H), 2.50–0.27 (m, 44H, include singlets at 2.50, 2.22, 2.08, 1.90, 1.87, 1.26, 1.14, 3H each and triplet at 0.77, 9H) ¹³C-NMR (CDCL₃, 75.469 MHz) δ: 205.05, 171.41, 169.80, 167.30, 141.15, 138.87, 133.73, 133.23, 130.29, 129.26, 128.74, 128.68, 127.94, 126.44, 85.31, 80.37, 79.20, 79.06, 75.87, 75.52, 75.27, 73.92, 71.09, 61.32, 53.07, 43.56, 43.14, 41.94, 40.45, 35.72, 31.65, 26.16, 22.80, 21.87, 20.86, 16.80, 15.05, 14.48, 6.54, 4.34 LRESIMS m/z Calcd. for C52H71NO14SSi [M+H]⁺ 965, found 965 IR (cm⁻¹): 3445.26, 2956.24, 1730.91, 1718.04, 1275.07, 1243.34, 1112.19, 1070.70, 710.04

EXAMPLE 23
3'-NH-ethylcarbonate-7-deoxy-6b-thiomethylpaclitaxel (28)

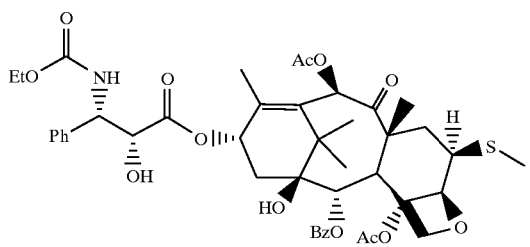

28

The triethylsilyl ether 27 (0.7198 g, 0.745 mmol) was dissolved in acetonitrile (12 mL), cooled to 0° C. and treated with 1M HCl (1.49 mL, 1.49 mmol) for 1 hour and 20 minutes. The reaction mixture was diluted with EtOAc, washed with NaHCO₃, water and brine. The solution was dried over MgSO₄, filtered and concentrated. The residue was chromatographed over silica gel (hexanes/ethyl acetate 3:1, 2:1, 1:1). The pure fractions were combined together and stripped to a residue, dissolved in a minimal amount of methylene chloride and precipitated with hexane. This suspension was stripped to a solid residue under vacuum to provide the thiomethyl ether 28 (0.546 g) as a white solid in 85% yield.
¹H-NMR (CDCL₃, 300.133 MHz) δ: 8.11 (d, 2H, J=7.3), 7.63–7.25 (m, 8H), 6.46 (s, 1H), 6.21 (t, 1H, J=8.4), 5.72 (d, 1H, J=6.7), 5.58 (d, 1H, J=9.4), 5.30 (d, 1H, J=8.7), 4.96 (d, 1H, J=5.8), 4.62 (bs, 1H), 4.31(d, 1H, J=8.0), 4.09 (d, 1H, J=8.0), 4.02 (q, 2H, J=7.1), 3.71 (d, 1H, J=6.6), 3.48 (bs, 1H), 3.41–3.34 (m, 1H), 2.38–1.12 (m, 29H, include. singlets at 2.35, 2.23, 2.07, 1.89, 1.80, 1.23, 1.14, 3H each) ¹³C-NMR (CDCL₃, 75.469 MHz) δ: 204.63, 170.50, 169.76, 167.21, 140.45, 133.82, 130.23, 129.18, 128.92, 128.73, 128.23, 126.85, 85.54, 80.47, 78.80, 75.65, 73.98, 73.79, 71.93, 61.48, 56.48, 53.12, 43.26, 43.09, 41.56, 39.90, 35.64, 31.65, 29.77, 26.28, 22.72, 22.52, 21.31, 20.87, 17.32, 14.83, 14.69, 14.54, 14.18 LRESIMS m/z Calcd. for C44H53NO14S [M+H]⁺ 851, found 851 IR (cm⁻¹): 3445.58, 2929.17, 1730.58, 1716.34, 1372.28, 1241.39, 1107.63, 1069.72, 868.26, 710.95

EXAMPLE 24
2'-O-(triethylsilyl)-7-deoxy-6b-thioethylpaclitaxel (29)

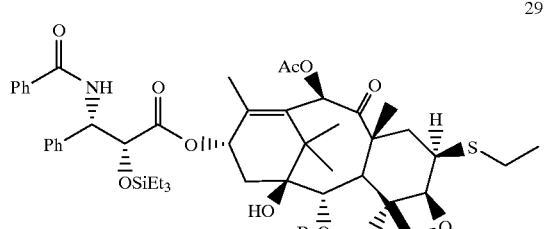

29

Thiol 12 (0.5 g, 0.508 mmol) was dissolved in benzene (9 mL) and degassed under house vacuum for 20 minutes, then backfilled with nitrogen. Iodoethane (61 uL, 0.762 mmol) and DBU (0.15 mL, 1.016 mmol) were then added and the reaction was stirred at room temperature for 20 minutes. The precipitated salts were filtered off on a short pass of silica gel and washed with 2:1 hexanes/ethyl acetate. The filtrate was stripped to a residue and chromatographed on silica gel (hexanes/ethyl acetate 4:1, 3:1) to provide 0.474 g of the thioethyl ether 29 as a white solid in 92% yield $^1$H-NMR (CDCL$_3$, 300.133 MHz) δ: 8.14 (d, 2H, J=7.1), 7.74 (d, 2H, J=7.0), 7.63–7.28 (m, 11H), 7.09 (d, 1H, J=8.8), 6.48 (s, 1H), 6.24 (t, 1H, J=8.4), 5.75–5.68 (m, 2H), 4.96 (d, 1H, J=6.4), 4.68(d, 1H, 2.0), 4.33 (d, 1H, J=8.0), 4.11 (d, 1H, J=8.1), 3.74 (d, 1H, 6.8), 3.54–3.47 (m, 1H), 2.59–0.33 (m, 43H, include singlets at 2.53, 2.21, 1.90, 1.21, 1.12, 3H each and triplet at 0.79, 9H) $^{13}$C-NMR (CDCL$_3$, 75.469 MHz) δ: 205.03, 171.54, 170.17, 169.81, 167.20, 166.96, 140.89, 138.53, 134.16, 133.74, 133.48, 131.82, 130.28, 129.26, 128.83, 128.75, 128.03, 127.11, 126.51, 85.48, 80.42, 78.98, 75.81, 75.45, 74.98, 73.98, 71.25, 55.75, 53.12, 43.45, 43.13, 41.39, 39.86, 35.90, 26.17, 25.77, 22.93, 21.82, 20.86, 16.94, 14.60, 14.54, 6.58, 4.44 LRESIMS m/z Calcd. for C55H69NO13SSi [M+H]$^+$ 1011, found 1011 IR (cm$^{-1}$): 3411.39, 2957.41, 1747.37, 1732.29, 1715.79, 1669.13, 1484.14, 1371.83, 1270.69, 1241.17, 1108.41, 1069.67, 968.92, 710.50

EXAMPLE 25
7-deoxy-6b-thioethylpaclitaxel (30)

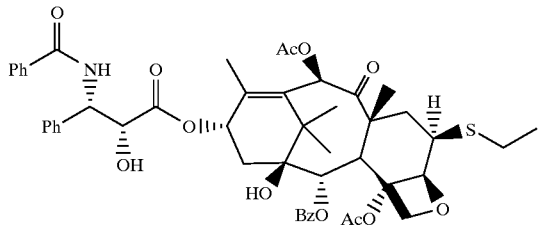

The triethylsilyl ether 29 (0.463 g, 0.457 mmol) was dissolved in acetonitrile (21 mL), cooled to 0° C. and treated with 1M HCl (0.9 mL, 0.915 mmol) for 20 minutes. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 2:1, 1:1). The pure fractions were combined together and stripped to a residue, dissolved in a minimal amount of methylene chloride and precipitated with hexane. This suspension was stripped to a solid residue under vacuum to provide the thioethyl ether 30 (0.368 g) as a white solid in 90% yield.

$^1$H-NMR (CDCL$_3$, 300.133 MHz) δ: 8.12 (d, 2H, J=7.1), 7.74 (d, 2H, J=7.1), 7.63–7.30 (m, 11H), 7.05 (d, 1H, J=9.0), 6.43 (s, 1H), 6.17 (t, 1H J=8.4), 5.78 (dd, 1H, J=2.5, 9.0), 5.72 (d, 1H, J=6.7), 4.92(d, 1H, J=5.8), 4.79–4.76 (m, 1H), 4.36 (d, 1H, J=8.0), 4.09 (d, 1H, J=7.9), 3.74 (d, 1H, 6.5), 3.65 (d, 1H, J=4.8, disappear with D$_2$O), 3.50–3.43 (m, 1H), 2.68–1.12 (m, 28H, include. singlets at 2.37, 2.27, 1.88, 1.74, 1.12, 3H each) $^{13}$C-NMR (CDCL$_3$, 75.469 MHz) δ: 204.64, 172.38, 170.54, 169.77, 167.16, 166.92, 140.30, 138.09, 133.94, 133.82, 133.73, 132.02, 130.23, 129.22, 129.04, 128.77, 128.38, 127.13, 127.10, 85.69, 80.45, 78.72, 75.64, 75.58, 74.02, 73.39, 72.10, 54.93, 55.14, 43.19, 43.09, 40.82, 39.61, 35.76, 31.65, 26.29, 25.64, 22.72, 22.58, 21.30, 20.87, 17.42, 14.61, 14.18 LRESIMS m/z Calcd. for C49H55NO13S [M−H]$^+$ 897, found 897 IR (cm$^{-1}$): 3435.69, 2930.07, 1733.39, 1718.09, 1664.00, 1654.44, 1487.03, 1372.82, 1270.69, 1239.54, 1106.80, 1069.56, 968.04, 711.06

EXAMPLE 26
2'-tert-butyldimethylsilyl-6-b-thiobenzyl-7-deoxypaclitaxel (31)

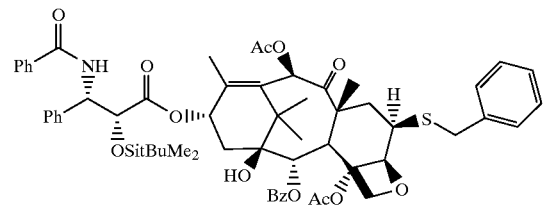

A solution of 2'-tert-butyldimethylsilyl-6-β-thio-7-deoxypaclitaxel (12a) (461.0 mg, 0.530 mmoles) in anhydrous benzene (4.5 mL) was treated with DBU (300.0 μL, 2.00 mmoles), then with benzyl bromide (125.0 μL, 1.05 mmoles) and stirred at ambient temperature under nitrogen until the reaction was complete according to analysis by TLC. The reaction mixture was diluted with ethyl acetate and washed with water followed by brine. The solution was dried over anhydrous Na$_2$SO$_4$, filtered and concentrated in vacuo. Purification by column chromatography on silica eluting with 75% hexanes/ethyl acetate afforded 361 mg (71.1%) of compound with formula 31 as a white, amorphous powder which exhibited the following physical properties: $^1$H NMR (CDCl$_3$, 300 MHz) δ 8.14 (d, J=7.8 Hz, 2H), 7.74 (d, J=7.7 Hz, 2H), 7.72–7.23 (m, 16H), 7.08 (d, J=9.0 Hz, 1H), 6.42 (s, 1H), 624 (t, J=8.3 Hz, 1H), 5.74 (m, 2H), 4.87 (d, J=6.2 Hz, 1H), 4.33 (d, J=8.0 Hz, 1H), 4.13 (d, J=8.0 Hz, 1H), 3.77–3.67 (m, 3H), 3.45–3.38 (m, 1H), 2.55 (s, 3H), 2.40–2.32 (m, 2H), 2.23 (s, 3H), 2.17–2.09 (m, 1H), 1.92 (s, 3H), 1.87 (s, 3H), 1.92–1.87 (m, 3H), 1.21 (s, 3H), 1.13 (s, 3H), 0.81 (s, 9H), −0.04 (s, 3H), −0.29 (s, 3H); $^{13}$C NMR (CDCl$_3$, 75 MHz) δ 205.49, 175.74, 171.87, 170.49, 170.27, 167.57, 141.34, 138.88, 138.28, 134.63, 134.19, 134.01, 132.39, 130.77, 129.81, 129.50, 129.32, 129.11, 128.56, 127.68, 127.57, 127.00, 86.09, 80.83, 79.30, 76.37, 76.10, 75.82, 74.52, 71.76, 56.23, 53.49, 43.74, 43.64, 41.38, 39.68, 36.35, 26.68, 26.12, 25.62, 23.45, 22.37, 21.39, 18.74, 17.92, 15.14, −4.61, −5.21.

EXAMPLE 27
6-b-thiobenzyl-7-deoxypaclitaxel (32).

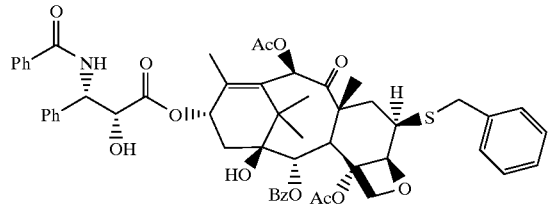

A solution of compound 31 (344 mg, 0.320 mmoles) in THF (5 mL) was cooled to −10° C. under nitrogen and treated with TBAF (1 M in THF, 150 μL, 0.150 mmoles). After stirring for 10 mins., the reaction was judged to be approximately 66% completed on the basis of TLC analysis and an additional amount of TBAF (50 μL, 0.050 mmoles) was added. After another 5 mins., the mixture diluted with ethyl acetate and washed with water, then brine. The solution was dried over anhydrous Na$_2$SO$_4$, filtered and concentrated in vacuo. Chromatography on silica eluting with 75% hexanes/ethyl acetate afforded 123 mg (40%) of compound with formula 32 as a white, amorphous solid which exhibited the following physical properties: $^1$H NMR (CDCl$_3$, 300 MHz) δ 8.12 (d, J=7.7 Hz, 2H), 7.76 (d, J=7.9 Hz, 2H), 7.64–7.21 m, 16H), 7.11 (d, J=9.1 Hz, 1H), 6.36 (s, 1H), 6.15 (t, J=7.0 Hz, 1H), 5.80 (dd, J=2.4 Hz, J=8.9 Hz, 1H), 5.72 (d, J=6.0 Hz, 1H), 4.83 (d, J=5.6 Hz, 1H), 4.78 (d, J=2.6 Hz, 1H), 4.31 (d, J=7.9 Hz, 1H), 4.12 (d, J=7.6 Hz, 1H), 3.75–3.65 (m, 3H), 3.38–3.31 (m, 1H), 2.35 (s, 3H), 2.31–2.26 (m, 2H), 2.23 (s, 3H), 2.00 (s, 1H), 1.89 (s, 3H), 1.87–1.80 (m, 2H), 1.64 (s, 3H), 1.19 (s, 3H), 1.12 (s, 3H); $^{13}$C NMR (CDCl$_3$, 75 MHz) δ 205.19, 172.83, 170.85, 170.28, 168.87, 167.52, 140.88, 138.67, 138.16, 134.26, 132.50, 130.71, 129.77, 129.47, 129.24, 129.12, 128.80, 127.66, 86.20, 80.82, 79.05, 78.85, 76.15, 74.54, 73.90, 72.38, 55.53, 53.51, 43.54, 40.91, 39.47, 36.28, 26.76, 25.61, 22.99, 21.82, 21.39, 18.74, 18.21, 15.09; LRMS (ESI): 958.3 ((M–1)$^-$, 100%).

EXAMPLE 28

2'-tert-butyldimethylsilyl-6-b-thiomethyl methyl keto-7-deoxypaclitaxel (33).

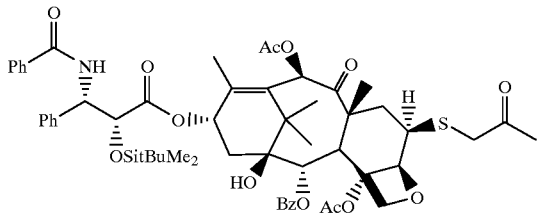

A solution of 2'-tert-butyldimethylsilyl-6-β-thio-7-deoxypaclitaxel (12a) (416.0 mg, 0.423 mmoles) in anhydrous benzene (4.0 mL) was treated with DBU (300.0 μL, 2.00 mmoles), then with α-chloroacetone (90.0 μL, 1.13 mmoles) and stirred at ambient temperature under for 10 mins. The reaction mixture was diluted with ethyl acetate and washed with water followed by brine. The solution was dried over anhydrous Na$_2$SO$_4$, filtered and concentrated in vacuo. Purification by column chromatography on silica eluting with 75% hexanes/ethyl acetate to 50% hexanes/ethyl acetate afforded 330 mg (75.0%) of compound with formula 33 as a white, amorphous powder which exhibited the following physical properties: $^1$H NMR (CDCl$_3$, 300 MHz) δ 8.15 (d, J=7.8 Hz, 2H), 7.73 (d, J=7.0 Hz, 2H), 7.61–7.34 (bm, 11H), 7.08 (d, J=8.9 Hz, 1H), 6.46 (s, 1H), 6.25 (t, J=9.0 Hz, 1H), 5.75–5.72 (m, 2H), 4.94 (d, J=6.7 Hz, 1H), 4.66 (d, J=1.9 Hz, 1H), 4.34 (d, J=8.0 Hz, 1H), 4.12 (d, J=8.3 Hz, 1H), 3.73 (d, J=7.0 Hz, 1H), 3.59–3.51 (m, 1H), 3.24 (d, J=14.1 Hz, 1H), 3.15 (d, J=14.0 Hz, 1H), 2.57 (s, 3H), 2.47–2.34 (m, 1H), 2.27 (s, 3H), 2.21 (s, 3H), 2.19–2.04 (m, 1H), 1.91 (s, 3H), 1.89 (s, 3H), 1.86–1.75 (m, 3H), 1.21 (s, 3H), 1.19 (s, 3H), 0.79 (s, 9H), –0.04 (s, 3H), –0.30 (s, 3H); $^{13}$C NMR (CDCl$_3$, 75 MHz) δ 205.48, 204.38, 171.88, 170.56, 170.22, 167.54, 153.91, 141.42, 138.81, 134.62, 134.17, 133.84, 132.36, 130.76, 129.81, 129.29, 128.54, 127.54, 129.99, 88.22, 80.67, 79.28, 76.27, 76.00, 75.78, 74.51, 71.76, 56.21, 53.44, 44.22, 43.59, 41.92, 41.46, 40.46, 36.45, 28.37, 26.65, 26.10, 23.36, 22.34, 21.33, 18.70, 17.11, 15.14, –4.66, –5.24.

EXAMPLE 29

6-b-thiomethyl methyl keto-7-deoxytaclitaxel (34).

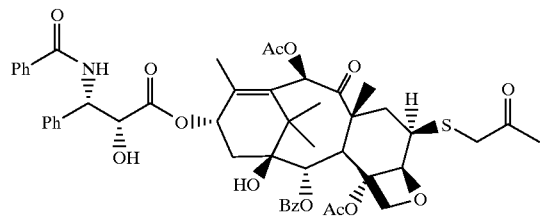

A solution of compound 33 (330 mg, 0.317 mmoles) in anhydrous THF (5.0 mL) was cooled to –10° C. under nitrogen and treated with TBAF (1M in THF, 250 μL, 0.250 mmoles). The mixture was removed from the cooling bath and stirred at ambient temperature for 15 mins. The mixture was diluted with ethyl acetate and washed with water, then brine. The solution was dried over anhydrous Na$_2$SO$_4$, and concentrated in vacuo. Chromatography on silica eluting with 75% hexanes/ethyl acetate afforded 178 mg of impure material that was subjected to chromatography on silica eluting with 90% hexanes/ethyl acetate to give 93 mg (31.7%) of compound with formula 34 as a white, amorphous solid which exhibited the following physical properties: $^1$H NMR (CDCl$_3$, 300 MHz) δ 8.13 (d, J=8.1 Hz, 2H), 7.75 (d, J=8.1 Hz, 2H), 7.62–7.36 (bm, 11H), 7.08 (d, J=8.9 Hz, 1H), 6.42 (s, 1H), 6.18 (t, J=8.4 Hz, 1H), 5.80 (dd, J=9.0 Hz, J=2.4 Hz 1H), 5.72 (d, J=6.6 Hz, 1H), 4.91 (d, J=6.2 Hz, 1H), 4.79 (d, J=2.5 Hz, 1H), 4.32 (d, J=8.0 Hz, 1H), 4.11 (d, J=8.3 Hz, 1H), 3.72 (d, J=6.8 Hz, 1H), 3.53–3.47 (m, 1H), 3.24 (d, J=18.6 Hz, 1H), 3.15 (d, J=13.2 Hz, 1H), 2.45 (m, 1H), 2.38 (s, 3H), 2.32 (s, 1H), 2.28 (s, 1H), 2.25 (s, 3H), 2.22 (s, 3H), 2.03 (s, 1H), 1.88 (s, 3H), 1.78 (s, 3H), 1.75 (m, 1H), 1.21 (s, 3H), 1.13 (s, 3H); $^{13}$C NMR (CDCl$_3$, 75 MHz) δ 205.27, 204.35, 173.03, 170.86, 170.26, 168.87, 167.69, 167.53, 141.07, 138.66, 134.27, 134.22, 134.09, 132.48, 130.72, 130.62, 129.78, 129.50, 129.26, 129.22, 128.80, 127.65, 127.60, 85.41, 80.68, 79.15, 76.10, 73.85, 74.59, 73.85, 72.50, 55.55, 53.49, 44.07, 43.53, 41.83, 41.08, 40.35, 36.32, 28.43, 26.75, 22.96, 21.89, 21.35, 17.38, 15.10, 14.75; LRMS (ESI): 926.4 ((M+1)$^+$, 100%).

EXAMPLE 30

2'-O-(triethylsilyl)-7-deoxy-6b-thioacetonitrilepaclitaxel (35)

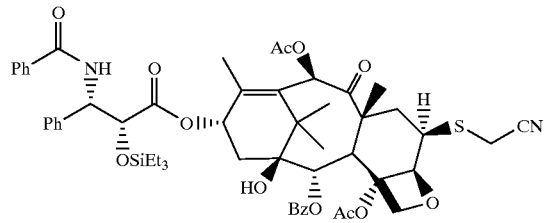

Thiol 12 (0.8 g, 0.813 mmol) was dissolved in benzene (15 mL) and degassed under house vacuum for 20 minutes, then backfilled with nitrogen. Iodoacetonitrile (88 uL, 1.219 mmol) and DBU (0.24 mL, 1.626 mmol) were then added and the reaction was stirred at room temperature for 30 minutes. The precipitated salts were filtered off on a short pass of silica gel and washed with 2:1 hexanes/ethyl acetate. The filtrate was stripped to a residue and chromatographed on silica gel (hexanes/ethyl acetate 3:1, 2:1) to provide 0.6954 g of the thioacetonitrile ether 35 as a white solid in 84% yield.

$^1$H-NMR (CDCl$_3$, 300.133 MHz) δ: 8.08 (d, 2H, J=7.0), 7.67 (d, 2H, J=7.0), 7.57–7.19 (m, 11H), 7.04 (d, 1H, J=8.9), 6.40 (s, 1H), 6.18 (t, 1H, J=8.7), 5.68–5.63 (m, 2H), 4.98 (d, 1H, J=7.0), 4.62(d, 1H, J=2.0), 4.31(d, 1H, J=8.1), 4.08(d, 1H, J=7.9), 3.76–3.61(m, 2H), 3.28–3.16 (m, 2H), 2.50–0.30 (m, 38H, include. singlets at 2.48, 2.15, 1.84, 1.82, 1.15, 1.06, 3H each and triplet at 0.74, 9H) $^{13}$C-NMR (CDCL$_3$, 75.469 MHz) δ: 204.85, 171.56, 170.18, 169.76, 167.17, 167.00, 141.14, 138.46, 134.16, 133.81, 133.23, 131.84, 130.93, 130.28, 129.18, 128.88, 128.80, 128.76, 128.06, 127.10, 126.50, 116.34, 84.52, 80.12, 78.97, 75.91, 75.61, 74.97, 73.99, 71.21, 68.22, 55.74, 52.96, 43.85, 43.08, 40.67, 40.31, 38.80, 35.99, 31.65, 30.43, 28.99, 26.13, 23.82, 23.04, 22.79, 22.71, 21.81, 20.82, 16.56, 16.40, 14.59, 14.18, 14.11, 11.02, 6.58, 4.44 LRESIMS m/z Calcd. for C55H66N2O13SSi [M+H]$^+$ 1022, found 1022

EXAMPLE 31
6b-thioacetonitrile-7-deoxypaclitaxel (36)

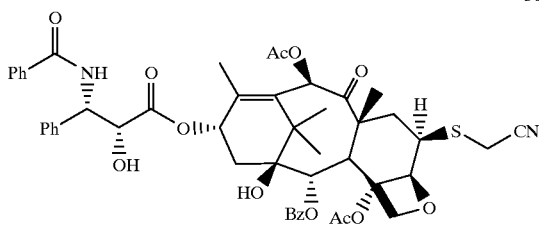

The triethylsilyl ether 35 (0.675 g, 0.660 mmol) was dissolved in acetonitrile (31 mL), cooled to 0° C. and treated with 1M HCl (1.3 mL, 1.319 mmol) for 30 minutes. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 2:1, 1:1). The pure fractions were combined together and stripped to a residue, dissolved in a minimal amount of methylene chloride and precipitated with hexane. This suspension was stripped to a solid residue under vacuum to provide the thioethyl ether 36 (0.585 g) as a white solid in 97% yield.

$^1$H-NMR (CDCL$_3$, 300.133 MHz) δ: 8.07 (d, 2H, J=7.1), 7.68 (d, 2H, J=7.0), 7.59–7.26 (m, 11H), 6.95 (d, 1H, J=8.9), 6.36 (s, 1H), 6.14 (t, 1H, J=8.5), 5.73 (dd, 1H, J=2.4, 8.9), 5.66 (d, 1H, J=6.8), 4.96(d, 1H, J=6.5), 4.74–4.71 (m, 1H), 4.29 (d, 1H, J=8.0), 4.07 (d, 1H, J=8.1), 3.73–3.66 (m, 2H), 3.53 (d, 1H, J=4.9, disappear with D$_2$O), 3.27–3.15 (m, 2H), 2.44–1.06 (m, 23H, include. singlets at 2.33, 2.15, 1.81, 1.72, 1.14, 1.06, 3H each) $^{13}$C-NMR (CDCL$_3$, 75.469 MHz) δ: 204.59, 172.64, 170.56, 169.80, 167.13, 140.68, 138.10, 133.90, 133.71, 133.64, 132.08, 130.28, 129.21, 129.13, 128.86, 128.81, 128.45, 127.14, 127.10, 116.37, 84.74, 80.16, 78.78, 76.03, 75.51, 74.06, 73.33, 72.18, 55.03, 52.99, 43.67, 43.08, 40.63, 40.02, 35.90, 26.29, 22.50, 21.46, 20.87, 16.80, 16.53, 14.68 LRESIMS m/z Calcd. for C49H52N2O13S [M+H]$^+$ 908, found 908 IR (cm$^{-1}$): 3432.48, 2953.79, 2245.30, 1733.46,1721.24, 1661.98, 1486.70 1372.15, 1271.12, 1240.36, 1107.31, 1070.11, 1023.99, 969.96, 711.34

EXAMPLE 32
6b-cyanomethylsulfoxo-7-deoxypaclitaxel (37 & 38)

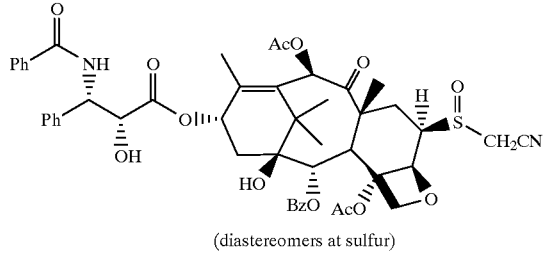

(diastereomers at sulfur)

A solution of 3-chloroperoxybenzoic acid (0.380 g, 1.10 mmol) in methylene chloride (5 mL) at 25° C. was added dropwise via a syringe to a solution of 36 (1.0 g, 1.10 mmol) in methylene chloride (20 mL) at –78° C. over 2 minutes. The reaction mixture was stirred at –78° C. for 5 minutes and then warmed up to –15° C. TLC shows the reaction finished in 20 minutes. The reaction was quenched with DMSO and stirred for 5 minutes at –15°. The reaction mixture was warmed up and diluted with EtOAc, washed with NaHCO$_3$, water and brine. The solution was dried over MgSO$_4$, filtered and concentrated. The residue was chromatographed over silica gel (methylene chloride/acetonitrile 10:1, 10:2) to provide the pure minor sulfoxide 37(190 mg, 19%) as a white solid, the pure slower eluting major sulfoxide 38 (373 mg, 37%) and an additional taxane (64.5 mg, 6%).

minor:
$^1$H-NMR (CDCL$_3$, 300.133 MHz) δ: 8.06 (d, 2H, J=7.1), 7.68 (d, 2H, J=7.0), 7.59–7.19 (m, 11H), 6.98 (d, 1H, J=8.7), 6.40 (s, 1H), 6.12 (t, 1H, J=8.9), 5.68 (dd, 1H, J=2.8, 8.7), 5.63 (d, 1H, J=7.2), 5.20 (d, 1H, J=8.4), 4.72 (d, 1H, J=2.4), 4.30 (d, 1H, J=8.3), 4.13 (d, 1H, J=8.4), 3.78–3.58 (m, 5H), 2.42–1.07 (m, 23H, include. singlets at 2.36, 2.13, 1.83, 1.76, 1.13, 1.07, 3H each) $^{13}$C-NMR (CDCL$_3$, 75.469 MHz) δ: 204.26, 173.03, 170.81, 170.05, 167.47, 167.23, 140.96, 138.23, 134.12, 133.96, 133.54, 132.19, 130.44, 129.21, 129.08, 129.08, 128.93, 128.55, 127.34, 127.18, 111.59, 81.94, 80.28, 79.13, 78.04, 75.45, 74.15, 73.43, 72.12, 60.43, 55.38, 52.83, 44.77, 43.16, 38.72, 36.07, 33.67, 26.35, 22.63, 21.70, 20.99, 15.84, 14.78 LRESIMS m/z Calcd. for C49H52N2O14S [M—H]$^+$ 924, found 924 IR (cm$^{-1}$): 3425.79, 2983.27, 2932.21, 2250.06, 1733.09, 1722.54, 1658.92, 1486.12, 1372.10, 1272.22, 1239.25, 1178.82, 1069.44, 1025.83, 972.55, 711.71 major:
$^1$H-NMR (CDCL$_3$, 300.133 MHz) δ: 8.12 (d, 2H, J=7.1), 7.73 (d, 2H, J=7.0), 7.65–7.25 (m, 11H), 7.04 (d, 1H, J=8.9), 6.41 (s, 1H), 6.18 (t, 1H, J=8.2), 5.79–5.72 (m, 2H), 5.27(d, 1H, J=5.9), 4.78 (s, 1H), 4.44 (d, 1H, J=8.1), 4.24 (d, 1H, J=8.0), 3.99–3.93 (m, 1H), 3.86–3.50 (m, 4H) 2.42–1.11 (m, 23H, include. singlets at 2.36, 2.20, 1.88, 1.80, 1.21, 1.11, 3H each) $^{13}$C-NMR (CDCL$_3$, 75.469 MHz) δ: 204.44, 172.85, 170.70, 170.12, 167.37, 167.25, 141.56, 138.28, 134.18, 133.88, 133.44, 132.22, 130.42, 129.30, 129.19, 129.09, 128.96, 128.59, 127.32, 127.26, 111.26, 82.67, 79.60, 78.79, 75.55, 74.19, 73.42, 72.16, 57.92, 55.22, 52.34, 43.19, 43.11, 37.90, 36.10, 33.38, 26.38, 22.48, 21.71, 20.99, 17.63, 14.97 IRESIMS m/z Calcd. for C49H52N2O14S [M–H]$^+$ 924, found 924 IR (cm$^{-1}$): 3424.86, 2983.48, 2930.13, 2250.05, 1734.98, 1719.49, 1656.30, 1518.89, 1486.80 1372.55, 1271.46, 1239.21, 1107.38, 1070.63, 1025.18, 969.56, 711.41

EXAMPLE 33
2'-triethylsilyl-6b-(2-thioacetic acid methyl ester)-7-deoxypaclitaxel (39).

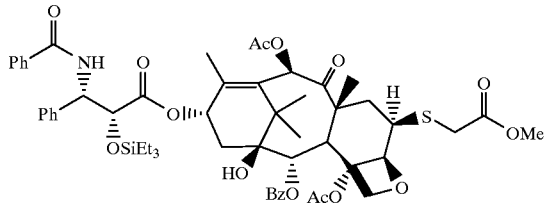

A solution of 2'-triethylsilyl-6-α-trifluoromethanesulfonyl-7-deoxy-paclitaxel ( ) (437.5 mg, 0.39 mmoles) in anhydrous benzene (10 mL) was treated with methyl thioglycolate (0.11 mL, 1.19 mmoles) and DBU (0.24 mL, 1.59 mmole) and stirred for 20 mins. at ambient temperature under nitrogen. The solution was transferred to a silica column packed with hexanes and eluted with 60% hexanes/ethyl acetate to give 371.8 mg (88.4%) of compound with formula 39 as a white, amorphous powder which exhibited the following physical properties: LRMS (ESI): 1073.6 ((M+NH$_4$)$^+$, 40%), 1056.0 ((M+1)$^+$, 100%).

EXAMPLE 34
6b-thioacetyl methyl ester-7-deoxypaclitaxel (40).

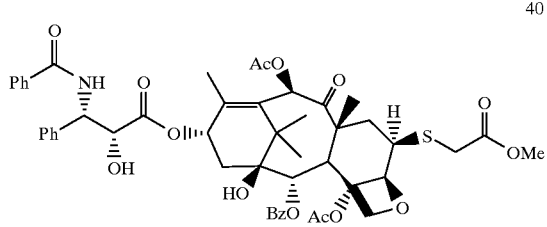

A solution of compound with formula 39 (370.0 mg, 0.350 mmoles) in acetonitrile (9.0 mL) was cooled to 0° C. under nitrogen and treated with 1N HCl (0.7 mL, 0.700 mmoles). After stirring at ambient temperature for 1.5 hrs., the mixture was concentrated in vacuo. Chromatography on silica eluting with 60% hexanes/ethyl acetate afforded 303.6 mg (92.1%) of compound with formula 40 as a white, amorphous solid which exhibited the following physical properties: $^1$H NMR (CDCl$_3$, 300 MHz) δ 8.12 (d, J=8.56 Hz, 2H), 7.73 (d, J=8.59 Hz, 2H), 7.63–7.30 (bm, 11H), 7.04 (d, J=8.97 Hz, 1H), 6.42 (s, 1H), 6.17 (m, 1H), 5.78 (dd, J=2.43 Hz, J=8.94 Hz, 1H), 5.70 (d, J=6.78 Hz, 1H), 4.98 (d, J=6.25 Hz, 1H), 4.77 (dd, J=2.65 Hz, J=4.71 Hz, 1H), 4.31 (d, J=8.03 Hz, 1H), 4.10 (d, J=7.01 Hz, 1H), 3.74–3.64 (m, 2H), 3.69 (s, 3H), 3.19 (dd, J=14.76 Hz, J=20.01 Hz, 2H), 2.40 (m, 1H), 2.38 (s, 3H), 2.30 (s, 1H), 2.28 (s, 1H), 2.21 (s, 3H), 2.03 (s, 1H), 1.87 (s, 3H), 1.76 (s, 3H), 1.66 (s, 2H), 1.19 (s, 3H), 1.12 (s, 3H); $^{13}$C NMR (CDCl$_3$, 75 MHz) δ 204.64, 172.49, 170.68, 170.44, 169.69, 167.13, 167.00, 140.39, 138.08, 133.82, 133.77, 133.72, 132.03, 130.24, 129.22, 129.05, 128.77, 128.38, 127.11, 85.03, 80.32, 78.73, 75.72, 75.56, 74.02, 73.33, 72.13, 54.95, 53.07, 52.56, 43.53, 43.06, 40.48, 40.36, 35.79, 32.96, 226.27, 22.52, 21.33, 20.85, 16.98, 14.60; LRMS (ESI): 942.4 ((M+1)$^+$, 42%), 286.3 (100%), 161.4 (60%), 105.3 (70%)

EXAMPLE 35
2'-O-(triethylsilyl)-7-deoxy-6b-allyl thioacetatepaclitaxel (41)

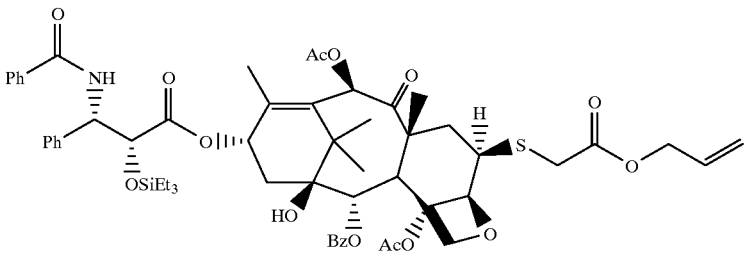

Thiol 12 (0.66 g, 0.670 mmol) was dissolved in benzene (11 mL) and degassed under house vacuum for 20 minutes, then backfilled with nitrogen. Allyl chloroacetate (93.5 uL, 1.005 mmol) and DBU (0.198 mL, 1.341 mmol) were then added and the reaction was stirred at room temperature for 20 minutes. The precipitated salts were filtered off on a short pass of silica gel and washed with 2:1 hexanes/ethyl acetate. The filtrate was stripped to a residue and chromatographed on silica gel (hexanes/ethyl acetate 3:1, 2:1) to provide 0.66 g of the desired product 41 as a white solid in 91% yield $^1$H-NMR (CDCL$_3$, 300.133 MHz) δ: 8.14 (d, 2H, J=7.0), 7.73 (d, 2H, J=7.0), 7.63–7.29 (m, 11H), 7.10 (d, 1H, J=8.9), 6.47 (s, 1H), 6.23 (t, 1H, J=9.3), 5.97–5.84 (m, 1H), 5.74–5.68 (m, 2H), 5.36–5.22 (m, 2H), 5.01 (d, 1H, J=6.9), 4.67(d, 1H, J=2.0), 4.60 (d, 1H, J=6.9), 4.34 (d, 1H, J=8.0), 411 (d, 1H, J=8.1), 3.79–3.71 (m, 2H), 3.27–3.15 (m, 2H), 2.52–0.35 (m, 38H, include. singlets at 2.52, 2.21, 1.89, 1.88, 1.25,1.15, 3H each and triplet at 0.80,9H) $^{13}$C-NMR (CDCL$_3$, 75.469 MHz) δ: 204.98, 171.55, 170.04, 169.94, 169.71, 167.19, 167.02, 140.89, 138.49, 134.14, 133.74, 133.35, 131.84, 131.80, 130.28, 129.27, 128.84, 128.76, 128.71, 128.04, 127.10, 126.50, 118.86, 84.77, 80.28, 78.96, 75.72, 75.585, 74.96, 73.96, 71.27, 66.06, 55.75, 53.08, 43.82, 43.10, 40.98, 40.48, 35.93, 33.19, 31.65, 26.14, 22.84, 22.72, 21.79, 20.85, 16.45, 14.55, 14.18 6.58,4.43 LRESIMS m/z Calcd. for C58H71NO15SSi [M+H]$^+$ 1081, found 1081 IR (cm$^{-1}$): 3442.25, 2956.06, 2878.21, 1731.90, 1668.09, 1484.27, 1371.75, 1272.40, 1241.49, 1127.26, 1069.92, 979.99, 711.04

EXAMPLE 36
7-deoxy-6b-allyl thioacetatepaclitaxel (42)

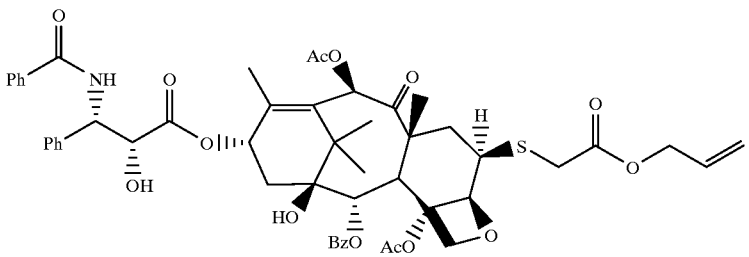

42

The triethylsilyl ether 41 (0.650 g, 0.600 mmol) was dissolved in acetonitrile (8 mL), cooled to 0° C. and treated with 1M HCl (1.2 mL, 1.20 mmol) for 1 hour. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 2:1, 1:1). The pure fractions were combined together and stripped to a residue, dissolved in a minimal amount of methylene chloride and precipitated with hexane. This suspension was stripped to a solid residue under vacuum to provide the thioethyl ether 42 (0.474 g) as a white solid in 82% yield.

$^1$H-NMR (CDCL$_3$, 300.133 MHz) δ: 8.12 (d, 2H, J=7.2), 7.74 (d, 2H, J=7.1), 7.64–7.25 (m, 11H), 7.04 (d, 1H, J=9.0), 6.43 (s, 1H), 6.17 (t, 1H, J=8.4), 5.94–5.83 (m, 1H), 5.78 (dd, 1H, J=2.4, 9.0), 5.71 (d, 1H, J=6.8), 5.36–5.21 (m, 2H), 4.98(d, 1H, J=6.3), 4.78–4.76 (m, 1H), 4.59 (d, 2H, J=5.6), 4.21(d, 1H, J=8.0), 4.10 (d, 1H, J=8.0), 3.75–3.68 (m, 2H), 3.62 (d, 1H, J=4.8), 3.27–3.15 (m, 2H), 2.45–1.12 (m, 23H, include. singlets at 2.37, 2.21, 1.87, 1.76, 1.19, 1.12, 3H each) $^{13}$C-NMR (CDCL$_3$, 75.469 MHz) δ: 204.62, 172.47, 170.41, 169.86, 169.65, 167.16, 166.96, 140.37, 138.09, 133.82, 133.76, 133.73, 132.02, 131.78, 130.25, 129.22, 129.05, 128.79, 128.76, 128.39, 127.11, 118.89, 84.99, 80.31, 78.77, 75.69, 75.57, 74.00, 73.35, 72.12, 66.08, 54.94, 53.11, 43.60, 43.05, 40.51, 40.30, 35.79, 33.09, 31.65, 26.28, 22.72, 22.51, 21.30, 20.85, 16.88, 14.62, 14.18 LRESIMS m/z Calcd. for C52H57NO15S [M+H]$^+$ 967, found 967 IR (cm$^{-1}$): 3449.31, 2930.08, 1733.76, 1663.85, 1372.03, 1273.56, 1241.51, 1108.57, 1070.60, 711.53

EXAMPLE 37
2'-O-(triethylsilyl)-7-deoxy-6b-thioacetamidepaclitaxel (43)

Thiol 12 (0.8 g, 0.813 mmol) was dissolved in benzene (15 mL) and degassed under house vacuum for 20 minutes, then backfilled with nitrogen. Iodoacetamide (226 uL, 1.219 mmol) and DBU (0.24 mL, 1.626 mmol) were then added and the reaction was stirred at room temperature for 35 minutes. The precipitated salts were filtered off on a short pass of silica gel and washed with 2:1 hexanes/ethyl acetate. The filtrate was stripped to a residue and chromatographed on silica gel (hexanes/ethyl acetate 1:1, 1:2, 1:3) to provide 0.720 g of the thioacetamide ether 43 as a white solid in 85% yield.

$^1$H-NMR (CDCL$_3$, 300.133 MHz) δ: 8.14 (d, 2H, J=7.1), 7.73 (d, 2H, J=7.1), 7.63–7.28 (m, 11H), 7.10 (d, 1H, J=8.9), 6.78 (broad s, 1H), 6.44 (s, 1H), 6.23 (t, 1H, J=8.7), 5.70 (t, 2H, J=8.1), 5.43 (broad s, 1H), 4.92 (d, 1H, J=6.6), 4.67(d, 1H, J=2.0), 4.34(d, 1H, J=8.0), 4.12 (d, 1H, J=8.0), 3.72 (d, 1H, J=6.8), 3.57–3.52 (m, 1H), 3.26–3.11 (m, 2H), 2.52–0.32 (m, 38H, include. singlets at 2.52, 2.20, 1.88, 1.86, 1.20, 1.00, 3H each and triplet at 0.80, 9H) $^{13}$C-NMR (CDCL$_3$, 75.469 MHz) δ: 204.86, 171.52, 171.38, 170.08, 169.75, 167.09, 166.98, 141.06, 138.36, 134.07, 133.76, 133.19, 131.80, 130.23, 129.12, 128.82, 128.75, 128.71, 128.02, 127.05, 126.43, 84.54, 79.94, 78.84, 75.56, 75.46, 74.86, 73.98, 71.13, 55.66, 52.76, 43.60, 43.02, 41.58, 41.11, 35.87, 35.72, 26.07, 22.77, 21.77, 20.80, 16.61, 14.53, 6.52, 4.34 LRESIMS m/z Calcd. for C55H68N2O14SSi [M+H]$^+$ 1040, found 1040 IR (cm$^{-1}$): 3442.50, 2956.22, 1734.02, 1717.28, 1667.60, 1486.49, 1371.71, 1272.58, 1241.77, 1112.59, 710.89

EXAMPLE 38
7-deoxy-6b-thioacetamidepaclitaxel (44)

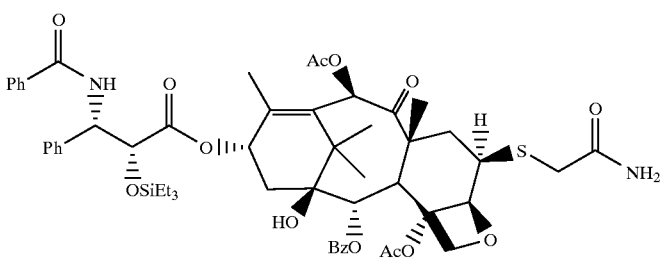

43

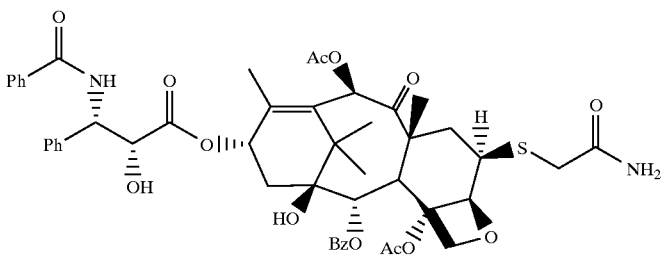

44

The triethylsilyl ether 43 (0.70 g, 0.672 mmol) was dissolved in acetonitrile (112 mL), cooled to 0° C. and treated with 1M HCl (1.3 mL, 1.344 mmol) for 30 minutes. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 1:2, 1:3, 1:6). The pure fractions were combined together and stripped to a residue, dissolved in a minimal amount of methylene chloride and precipitated with hexane. This suspension was stripped to a solid residue under vacuum to provide the thioacetamide ether 44 (0.514 g) as a white solid in 83% yield.

$^1$H-NMR (CDCL$_3$, 300.133 MHz) δ: 8.13 (d, 2H, J=7.4), 7.74 (d, 2H, J=7.2), 7.64–7.33 (m, 11H), 7.04 (d, 1H, J=9.0), 6.73 (bs, 1H), 6.40 (s, 1H), 6.18 (t, 1H, J=8.6), 5.79 (d, 1H, J=9.0), 5.71 (d, 1H, J=6.8), 5.45 (bs, 1H), 4.91(d, 1H, J=6.0), 4.79 (d, 1H, J=2.3), 4.33(d, 1H, J=8.0), 4.12 (d, 1H, J=8.0), 3.74 (d, 1H, J=6.7), 3.57–3.48 (m, 2H), 3.26–3.10 (m, 2H), 2.47–1.12 (m, 23H, include. singlets at 2.38, 2.21, 1.86, 1.77, 1.21, 1.12, 3H each) $^{13}$C-NMR (CDCL$_3$, 75.469 MHz) δ: 204.82, 172.98, 171.88, 170.59, 170.05, 167.42, 167.18, 140.96, 138.32, 134.00, 133.96, 133.79, 132.15, 130.40, 129.19, 129.10, 128.97, 128.88, 128.45, 127.34, 127.28, 84.95, 80.17, 78.77, 75.83, 75.70, 74.35, 73.54, 72.23, 55.25, 52.96, 43.38, 43.26, 41.28, 40.67, 35.98, 35.55, 26.41, 22.65, 21.63, 21.03, 17.53, 14.81 LRESIMS m/z Calcd. for C49H54N2O14S [M-H]$^+$ 926, found 926 IR (cm$^{-1}$): 3435.95, 2930.50, 1734.17,1717.17, 1670.34, 1372.53, 1241.32, 1070.36, 711.33

EXAMPLE 39
2'tertbutyldimethylsilyl-6-b-methylthiomethylthio ether-7-deoxy paclitaxel(45).

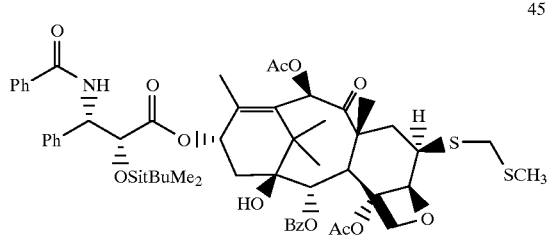

45

A solution of 2'-tert-butyldimethylsilyl-6β-thio-7-deoxy-paclitaxel (12a) (311.0 mg, 0.357 mmoles) in anhydrous benzene (3.0 mL) was treated with DBU (300.0 μL, 2.00 mmoles), then with chloromethyl methyl sulfide (60.0 μL, 0.715 mmoles) and stirred at ambient temperature under for 60 mins. The reaction mixture was diluted with ethyl acetate and washed with water followed by brine. The solution was dried over anhydrous Na$_2$SO$_4$, filtered and concentrated in vacuo. Purification by column chromatography on silica eluting with 75% hexanes/ethyl acetate to 50% hexanes/ethyl acetate afforded 178.0 mg (47.0%) of compound with formula 45 as a white, amorphous powder which exhibited the following physical properties: $^1$H NMR (CDCl$_3$, 300 MHz) δ 8.15 (d, J=7.8 Hz, 2H), 7.73 (d, J=7.8 Hz, 2H), 7.72–7.26 (m. 11H), 7.09 (d, J=8.9 Hz, 1H), 6.49 (s, 1H), 6.26 (t, J=8.8 Hz, 1H), 5.77–5.73 (m, 2H), 4.99 (d, J=6.8 Hz, 1H), 4.66 (d, J=2.1 Hz, 1H), 4.35 (d, J=8.1 Hz, 1H), 4.15–4.09 (m, 2H), 3.76 (d, J=6.9 Hz, 1H), 3.66–3.55 (m, 2H), 2.58 (s, 3H), 2.54–2.36 (m, 2H), 2.21 (s, 3H), 2.13 (s, 3H), 1.91 (s, 3H), 1.90 (s, 3H), 1.21 (s, 3H), 1.12 (s, 3H), 0.80 (s, 9H), '0.04 (s, 3H), –0.30 (s, 3H).

EXAMPLE 40
6-b-methylthiomethylthio ether-7-deoxy paclitaxel(46).

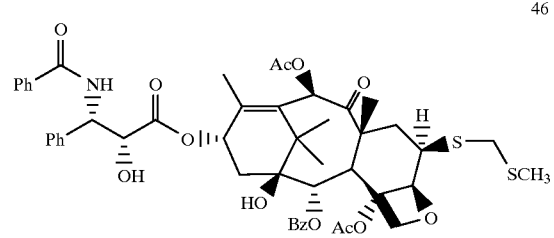

46

A solution of compound 45 (202 mg, 0.193 mmoles) in anhydrous THF (4.0 mL) was cooled to –10° C. under nitrogen and treated with TBAF (1M in THF, 250 μL, 0.250 mmoles). The mixture was removed from the cooling bath and stirred at ambient temperature for 5 mins. The mixture was diluted with ethyl acetate and washed with water, then brine. The solution was dried over anhydrous Na$_2$SO$_4$, and concentrated in vacuo. Chromatography on silica eluting with 75% hexanes/ethyl acetate to 50% hexanes/ethyl acetate afforded 132.0 mg (75.0%) of compound with formula 46 as a white, amorphous solid which exhibited the following physical properties: $^1$H NMR (CDCl$_3$, 300 MHz) δ 8.14 (d, J=7.8 Hz, 2H), 7.74 (m, 2H), 7.65–7.26 (m, 11H), 7.08 (d, J=9.0 Hz, 1H), 6.45 (s, 1H), 6.19 (t, J=8.6 Hz, 1H), 5.80 (dd, J=9.0 Hz, J=3.0 Hz, 1H), 5.73 (d, J=6.8 Hz, 1H), 4.96 (d, J=6.0 Hz, 1H), 4.79 (d, J=2.6 Hz, 1H), 4.34 (d, J=8.1 Hz, 1H), 4.13 (d, J=8.1 Hz, 1H), 3.83–3.75 (m, 2H), 3.65–3.55 (m, 2H), 2.43 (m, 1H), 2.39 (s, 3H), 2.32 (s, 1H), 2.29 (s, 1H), 2.22 (s, 3H), 2.13 (s, 3H), 1.89 (s, 3H), 1.88–1.78 (m, 3H), 1.78 (s, 3H), 1.21 (s, 3H), 1.13 (s, 3H); $^{13}$C NMR (CDCl$_3$, 75 MHz) δ 205.35, 172.95, 170.93, 170.28, 167.58, 140.98, 138.63, 134.27, 134.21, 132.47, 130.72, 129.77, 129.48, 129.26, 129.21, 128.80, 127.65, 127.60, 100.68, 85.98, 80.85, 79.21, 76.13, 74.62, 73.89, 72.48, 55.53, 53.62, 44.12, 43.54, 41.37, 39.08, 38.00, 36.31, 26.76, 23.01, 21.86, 21.36, 17.44, 15.11, 14.92; LRMS (ESI): 930.4 ((M+1)$^+$, 100%).

EXAMPLE 41
2'tertbutyldimethylsilyl-6-b-methylthiomethylether-7-deoxy paclitaxel (47).

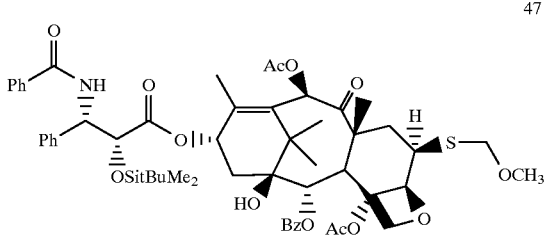

A solution of 2'-tert-butyldimethylsilyl-6-β-thio-7-deoxy-paclitaxel (12a) (440.0 mg, 0.447 mmoles) in anhydrous benzene (4.0 mL) was treated with DBU (270.0 µL, 1.80 mmoles), then with bromomethyl methyl ether (75.0 µL, 0.894 mmoles) and stirred at ambient temperature under for 10 mins. The reaction mixture was diluted with ethyl acetate and washed with water followed by brine. The solution was dried over anhydrous $Na_2SO_4$, filtered and concentrated in vacuo. Purification by column chromatography on silica eluting with 75% hexanes/ethyl acetate to 50% hexanes/ethyl acetate afforded 450.0 mg (96.4%) of compound with formula 47 as a white, amorphous powder which exhibited the following physical properties: $^1$H NMR (CDCl$_3$, 300 MHz) δ 8.15 (d, J=6.9 Hz, 2H), 7.45 (dd, J=1.5 Hz, J=6.9 Hz, 2H), 7.61–7.31 (m, 11H), 7.06 (d, J=8.9 Hz, 1H), 6.48 (s, 1H), 6.26 (m, 1H), 5.75–5.72 (m, 2H), 4.99 (d, J=7.0 Hz, 1H), 4.68–4.52 (m, 3H), 4.34 (d, J=7.7 Hz, 1H), 4.13 (m, 2H), 3.74 (m, 2H), 3.32 (s, 3H), 2.57 (s, 3H), 2.56–2.36 (m, 2H), 2.21 (s, 3H), 2.18–2.08 (m, 1H), 2.04 (s, 3H), 1.90 (s, 3H), 1.22 (s, 3H), 1.13 (s, 3H), 0.79 (s, 9H).

EXAMPLE 42
6-b-methylthiomethylether-7-deoxy paclitaxel (48).

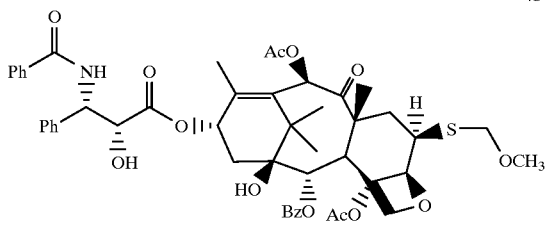

A solution of compound with formula 47 (450 mg, 0.438 mmoles) in anhydrous THF (4.0 mL) was cooled to −10° C. under nitrogen and treated with TBAF (1M in THF, 200 µL, 0.200 mmoles). The mixture was removed from the cooling bath and stirred at ambient temperature for 10 mins. The reaction was judged to be incomplete by TLC analysis, so additional TBAF (100 µL, 0.100 mmoles) was added and the reaction was stirred at ambient temperature for another 10 mins. The mixture was diluted with ethyl acetate and washed with saturated NaHCO$_3$ solution, water, then brine. The solution was dried over anhydrous Na$_2$SO$_4$, and concentrated in vacuo. Chromatography on silica eluting with 75% hexanes/ethyl acetate to 50% hexanes/ethyl acetate afforded 200.2 mg (50.0%) of compound with formula 48 as a white, amorphous solid which exhibited the following physical properties: $^1$H NMR (CDCl$_3$, 300 MHz) δ 8.13 (d, J=7.7 Hz, 2H), 7.75–7.72 (m, 2H), 7.64–7.26 (m, 11H), 7.12 (d, J=9.0 Hz, 1H), 6.43 (s, 1H), 6.17 (t, J=8.1 Hz, 1H), 5.79 (dd, J=9.0 Hz, J=2.5 Hz, 1H), 5.72 (d, J=6.9 Hz, 1H), 4.96 (d, J=6.2 Hz, 1H), 4.78 (dd, J=5.0 Hz, J=2.6 Hz, 1H), 4.64 (d, J=11.7 Hz, 1H), 4.53 (d, J=11.8 Hz, 1H), 4.31 (d, J=8.0 Hz, 1H), 4.10 (d, J=8.0 Hz, 1H), 3.78 (d, J=5.0 Hz, 1H), 3.73 (d, J=6.7 Hz, 1H), 3.70–3.63 (m, 1H), 3.30 (s, 3H), 2.45 (m, 1H), 2.37 (s, 3H), 2.31 (s, 1H), 2.28 (s, 1H), 2.21 (s, 3H), 1.99 (s, 1H), 1.92–1.84 (m, 2H), 1.88 (s, 3H), 1.76 (s, 3H), 1.19 (s, 3H), 1.13 (s, 3H); $^{13}$C NMR (CDCl$_3$, 75 MHz) δ 205.30, 172.97, 170.93, 170.23, 167.58, 140.85, 138.63, 134.24, 132.49, 130.72, 129.79, 129.50, 129.23, 128.81, 127.61, 86.03, 80.82, 79.20, 76.09, 75.98, 75.52, 74.55, 73.85, 72.56, 56.36, 55.50, 54.02, 53.65, 44.15, 43.54, 41.96, 39.54, 36.30, 26.74, 23.00, 21.84, 21.35, 17.26, 15.06; LRMS (ESI): 914.4 ((M+1)$^+$, 100%).

EXAMPLE 43
2'-O-(triethylsilyl)-6b-thioethenyl-7-deoxypaclitaxel (49) and 6b-thioethenyl-7-deoxypaclitaxel (50)

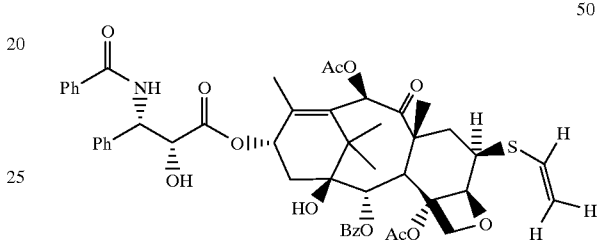

Thiol 12 (0.90 g, 0.912 mmol) was dissolved in toluene (27 mL) and degassed under house vacuum for 20 minutes, then backfilled with nitrogen. Vinyl sulfoxide (0.128 mL, 0.957 mmol) and DBU (0.20 mL, 1.368 mmol) were then added and the reaction was stirred at room temperature for 3 hours. The reaction mixture was then placed in an oil bath and reflux for 5 hours and 30 minutes. The reaction mixture was then cooled and diluted with EtOAc, washed with NaHCO$_3$, water and brine. The solution was dried over MgSO$_4$, filtered and concentrated. The residue was chromatographed on silica gel (hexanes/ethyl acetate 3:1, 2:1) to provide 0.43 g of the impure vinyl sulfide 49 in 47% yield which was used directly for the next step reaction.

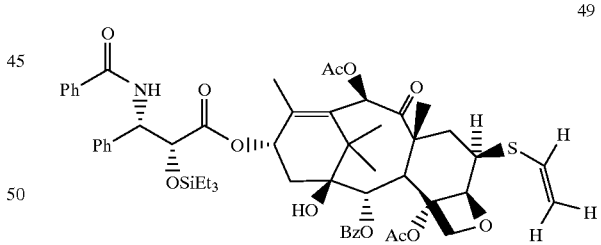

LRESIMS m/z Calcd. for C55H67NO13SSi [M+H]$^+$ 1009, found 1009

The triethylsilyl ether 49 (0.43 g, 0.426 mmol) was dissolved in acetonitrile (16 mL), cooled to 0° C. and treated with 1M HCl (0.85 mL, 0.851 mmol) for 1 hour and 20 minutes. The reaction mixture was diluted with EtOAc, washed with NaHCO$_3$, water and brine. The solution was dried over MgSO$_4$, filtered and concentrated. The residue was chromatographed over silica gel (hexanes/ethyl acetate 2:1, 1.5:1) to provide the vinylsulfide 50 (0.265g, 70%) as a white solid. Also recovered were some mixed fractions (44 mg, 12%) and a slower eluting compound (32 mg, 8%).

$^1$H-NMR (CDCL$_3$, 300.133 MHz) δ: 8.12 (d, 2H, J=7.0), 7.74 (d, 2H, J=7.0), 7.64–7.30 (m, 11H), 7.04 (d, 1H, J=9.0), 6.43 (s, 1H), 6.32–6.23 (m, 1H) 6.18 (t, 1H, J=8.1), 5.79 (dd, 1H, J=2.4, 9.0), 5.73 (d, 1H, J=6.7), 5.29–5.17 (m, 2H), 4.98(d, 1H, J=5.8), 4.79–4.77 (m, 1H), 4.32 (d, 1H, J=8.0), 4.12 (d, 1H, J=7.9), 3.78–3.71 (m, 2H), 3.64 (d, 1H, J=4.8), 2.42–1.13 (m, 23H, include. singlets at 2.38, 2.21, 1.89, 1.75, 1.20, 1.13, 3H each) $^{13}$C-NMR (CDCL$_3$, 75.469 MHz) δ: 204.48, 172.46, 170.60, 169.76, 167.16, 167.01, 140.41, 138.12, 133.94, 133.86, 133.75, 132.06, 130.51, 130.26, 129.23, 129.08, 128.80, 128.42, 127.14, 127.13, 114.25, 85.26, 80.31, 78.74, 75.80, 75.63, 74.02, 73.40, 72.13, 54.98, 53.06, 43.20, 43.11, 40.29, 40.16, 35.82, 34.48, 32.00, 29.79, 26.31, 22.57, 22.22, 21.37, 20.88, 17.48, 14.67 LRESIMS m/z Calcd. for C49H53NO13S [M+H]$^+$ 895, found 895 IR (cm$^{-1}$): 3432.06, 2932.39, 1732.82, 1717.31, 1663.32, 1372.00, 1271.17, 1240.10, 1107.20, 1069.66, 1025.06, 968.22, 710.50

EXAMPLE 44

2'-O-(triethylsilyl)-6b-thiophenyl-7-deoxy-paclitaxel (51).

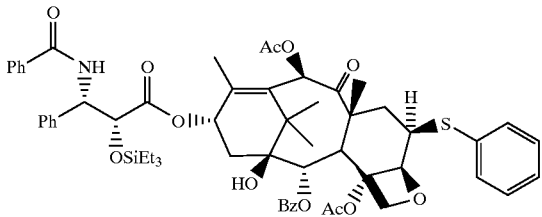

A solution of 2'-triethylsilyl-6-α-trifluoromethanesulfonyl-7-deoxy-paclitaxel (7) (261.1 mg, 0.237 mmoles) in anhydrous benzene (4.4 mL) was treated with thiophenol (73.0 μL, 0.711 mmoles) and DBU (142.0 μL, 0.949 mmoles) and stirred for 40 mins. at ambient temperature under nitrogen. The solution was transferred to a silica column packed with hexanes and eluted with 70% hexanes/ethyl acetate to give 210.6 mg (83.8%) of compound with formula 51 as a white, amorphous powder which exhibited the following physical properties: $^1$H NMR (CDCl$_3$, 300 MHz) δ 8.14 (d, J=7.1 Hz, 2H), 7.72 (d, J=7.1 Hz, 2H), 7.63–7.18 (bm, 16H), 7.10 (d, J=8.8 Hz, 1H), 6.45 (s, 1H), 6.22 (m, 1H), 5.74 (d, J=6.9 Hz, 1H), 5.68 (d, J=8.9 Hz, 1H), 5.00 (d, J=6.8 Hz, 1H), 4.67 (d, J=2.0 Hz, 1H), 4.34 (d, J=7.9 Hz, 1H), 4.14 (d, J=8.1 Hz, 1H), 3.94 (m, 1H), 3.73 (d, J=6.9 Hz, 1H), 2.51 (s, 3H), 2.47–2.34 (m, 2H), 2.20 (s, 3H), 2.17 (m, 1H), 1.97–1.92 (m, 1H), 1.95 (s, 3H), 1.88 (s, 3H), 120 (s, 3H), 1.13 (s, 3H), 0.81 (t, J=7.87 Hz, 9H), 0.53–0.32 (bm, 6H); LRMS (ESI): 1060 ((M+1)$^+$, 10%).

EXAMPLE 45

6b-thiophenyl-7-deoxy-paclitaxel (52).

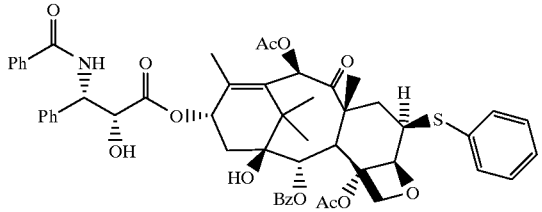

A solution of compound with formula 51 (206 mg, 0.195 mmoles) in acetonitrile (5.0 mL) was cooled to 0° C. under nitrogen and treated with 1N HCl (0.40 mL, 0.389 mmoles).

After stirring at ambient temperature for 1.25 hrs., the mixture was concentrated in vacuo. Chromatography on silica eluting with 50% hexanes/ethyl acetate afforded 151.8 mg (82.3%) of compound with formula 52 as a white, amorphous solid which exhibited the following physical properties: $^1$H NMR (CDCl$_3$, 300 MHz) δ 8.12 (d, J=7.3 Hz, 2H), 7.72 (d, J=7.2 Hz, 2H), 7.61–7.18 (bm, 16H), 7.04 (d, J=9.0 Hz, 1H), 6.41 (s, 1H), 6.17 (m, 1H), 5.78–5.72 (m, 2H), 4.95 (d, J=6.3 Hz, 1H), 4.76 (dd, J=2.6 Hz, J=5.0 Hz, 1H), 4.32 (d, J=8.0 Hz, 1H), 4.12 (d, J=8.0 Hz, 1H), 3.92 (ddd, J=4.5 Hz, J=5.4 Hz, J=9.8 Hz, 1H), 3.73 (d, J=6.5 Hz, 1H), 3.66 (d, J=5.0 Hz, 1H), 2.41 (m, 1H), 2.35 (s, 3H), 2.30 (s, 1H), 2.28 (s, 1H), 2.20 (s, 3H), 1.98 (s, 1H), 1.88 (m, 1H), 1.75 (s, 3H), 1.69 (s, 3H), 1.19 (s, 3H), 1.13 (s, 3H); $^{13}$C NMR (CDCl$_3$, 75 MHz) δ 204.64, 172.52, 170.48, 169.67, 167.15, 167.06, 140.24, 138.07, 134.62, 133.85, 133.80, 133.70, 132.04, 131.57, 130.24, 129.25, 129.18, 129.06, 128.77, 128.39, 127.26, 127.11, 84.74, 80.38, 78.72, 77.29, 75.60, 73.98, 73.33, 72.17, 60.47, 54.99, 53.20, 43.59, 43.55, 43.06, 40.70, 35.79, 26.26, 22.52, 21.35, 21.11, 20.86, 17.05, 14.57, 14.26; LRMS (ESI): 944.8 ((M-1)$^-$, 10%).

EXAMPLE 46

2'-O-(tertbutyldimethylsilyl)-6-b-thio-(2-thienyl)-7-deoxypaclitaxel(53).

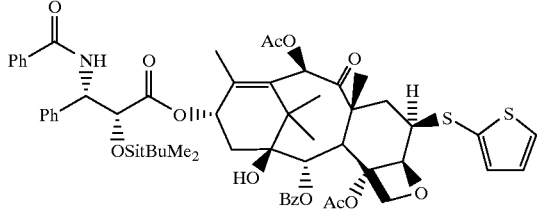

A solution of 2'-tert-butyldimethylsilyl-6-α-trifluoromethanesulfonyl-7-deoxy-paclitaxel (7a) (500.0 mg, 0.454 mmoles) in anhydrous benzene (15.0 mL) was treated with thiophenethiol (50.0 μL, 0.500 mmoles) and DBU (85.0 μL, 0.540 mmoles) and stirred for 50 mins. at ambient temperature under nitrogen. The solution was concentrated in vacuo and subjected to column chromatography on silica eluting with 70% hexanes/ethyl acetate to give 476.4 mg (98.4%) of compound with formula 53 as a white, amorphous powder which exhibited the following physical properties: $^1$H NMR (CDCl$_3$, 300 MHz) δ 8.12 (d, J=7.2 Hz, 2H), 7.69 (d, J=7.2 Hz, 2H), 7.58–7.28 (bm, 12H), 7.13 (d, J=2.4 Hz, 1H), 7.03 (d, J=9.0 Hz, 1H), 6.93 (dd, J=3.4 Hz, J=5.4 Hz, 1H), 6.43 (s, 1H), 6.21 (m, 1H), 5.71 (m, 2H), 4.99 (d, J=7.1 Hz, 1H), 4.62 (d, J=2.1 Hz, 1H), 4.34 (d, J=8.1 Hz, 1H), 4.12 (d, J=8.1 Hz, 1H), 3.74–3.67 (m, 2H), 2.52 (s, 3H), 2.41–2.31 (m, 2H), 2.18 (s, 3H), 2.13–2.05 (m, 2H), 2.01 (s, 1H), 1.93 (s, 3H), 1.84 (s, 3H), 1.17 (s, 3H), 1.09 (s, 3H), 0.76 (s, 9H), −0.076 (s, 3H), −0.33 (s, 3H); $^{13}$C NMR (CDCl$_3$, 75 MHz) δ 205.10, 171.52, 170.35, 169.84, 167.36, 167.16, 140.87, 138.49, 135.63, 134.30, 133.90, 133.56, 132.95, 132.03, 130.66, 130.46, 129.45, 129.00, 128.97, 128.20, 127.95, 127.22, 126.64, 84.51, 80.60, 79.11, 77.46, 75.86, 75.80, 75.44, 74.02, 71.39, 60.62, 55.85, 53.39, 48.02, 44.20, 43.25, 40.84, 36.09, 26.28, 25.74, 23.04, 21.97, 21.27, 21.03, 19.45, 18.37, 16.53, 14.73, 14.43; LRMS (ESI): 1067.5 ((M+1)$^+$, 100%), 400.3 (60%).

EXAMPLE 47
6-b-thio-(2-thienyl)-7-deoxypaclitaxel (54)

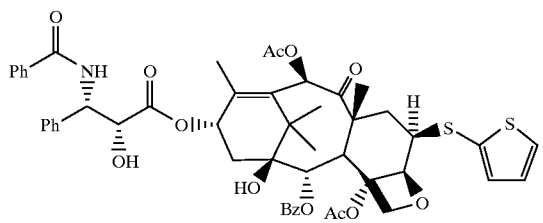

A solution of compound 53 (456.4 mg, 0.428 mmoles) in THF (21.4 mL) was cooled to −10° C. under nitrogen and treated with TBAF (1M in THF, 0.40 mL, 0.40 mmoles). After stirring in the cold for 10 mins., the mixture was diluted with ethyl acetate (100 mL) and washed with brine (20 mL). The solution was dried over anhydrous $Na_2SO_4$, and concentrated in vacuo. Chromatography on silica eluting with 60% hexanes/ethyl acetate afforded 381 mg (93.5%) of compound with formula 54 as a white, amorphous solid which exhibited the following physical properties: $^1$H NMR ($CDCl_3$, 300 MHz) δ 8.05 (d, J=7.1 Hz, 2H), 7.65 (d, J=7.1 Hz, 2H), 7.55–7.26 (bm, 12H), 7.07 (dd, J=1.2 Hz, J=3.5 Hz, 1H), 6.96 (d, J=8.9 Hz, 1H), 6.88 (dd, J=3.6 Hz, J=5.3 Hz, 1H), 6.34 (s, 1H), 6.10 (t, J=8.1 Hz, 1H), 5.70 (dd, J=2.4 Hz, J=9.0 Hz, 1H), 5.65 (d, J=6.9 Hz, 1H), 4.90 (d, J=6.7 Hz, 1H), 4.69 (dd, J=2.6 Hz, J=5.0 Hz, 1H), 4.27 (d, J=8.1 Hz, 1H), 4.05 (d, J=8.0 Hz, 1H), 3.67–3.57 (bm, 2H), 2.28 (s, 3H), 2.24 (s, 1H), 2.21 (s, 1H), 2.14 (s, 3H), 1.97 (s, 1H), 1.84 (s, 3H), 1.63 (s, 3H), 1.12 (s, 3H), 1.06 (s, 3H);); $^{13}$C NMR ($CDCl_3$, 75 MHz) δ 204.66, 172.57, 170.43, 169.67, 167.11, 140.24, 138.10, 135.52, 133.81, 133.75, 132.53, 132.06, 130.57, 130.27, 129.31, 129.08, 128.80, 128.41, 127.80, 127.12, 84.48, 80.46, 78.76, 77.31, 75.73, 75.60, 73.96, 73.33, 72.21, 64.46, 55.01, 53.27, 55.01, 53.27, 47.56, 43.89, 43.07, 40.28, 35.83, 26.27. 22.51, 21.37, 21.09, 20.89, 19.21, 16.72, 14.54; LRMS (ESI): 952.4 ((M+1)$^+$, 100%).

EXAMPLE 48
2'-O-(tertbutyldimethylsilyl)-6-b-(2-thioacetic acid)-7-deoxy-paclitaxel (55)

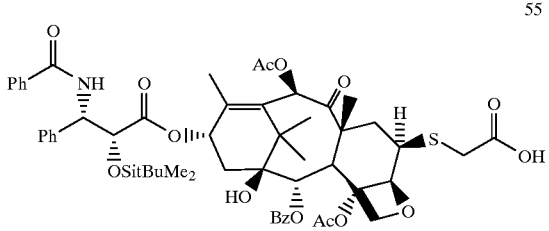

A solution of compound 42 (121.5 mg, 0.126 mmoles) in DCM (2.0 mL) was treated with palladium acetate (3.3 mg, 0.015 mmoles), triphenylphosphine (23 mg, 0.700 mmoles) and 2-ethyl hexanoic acid (0.5 M solution in ethyl acetate, 0.38 mL, 0.188 mmoles). The mixture was stirred at ambient temperature for 23 hrs., then diluted with DCM (20 mL) and washed with 1 N HCl, water, then brine (5.0 mL each). The solution was dried over anhydrous $Na_2SO_4$, and concentrated in vacuo. Chromatography on silica eluting with 50% hexanes/ethyl acetate plus 1% formic acid afforded 114.8 mg (98.2%) of compound with formula 55 as a white, amorphous solid which exhibited the following physical properties: $^1$H NMR ($CDCl_3$, 300 MHz) δ 8.06 (d, J=7.1 Hz, 2H), 7.67 (d, J=7.0 Hz, 2H), 7.59–7.21 m, 12H), 6.35 (s, 1H), 6.08 (t, J=8.9 Hz, 2H), 5.70–5.65 (m, 2H), 4.93 (d, J=6.0 Hz, 1H), 4.71 (m, 1H), 4.24 (d, J=8.0 Hz, 1H), 4.08–3.96 (m, 2H), 3.64 (m, 2H), 3.15–3.03 (dd, J=14.7 Hz, J=21.5 Hz, 2H), 2.50 (bs, 1H), 2.36–2.20 (m, 3H), 2.29 (s, 3H), 2.15 (s, 3H), 1.97 (s, 1H), 1.81 (s, 3H), 1.77–1.75 (m, 1H), 1.73 (s, 3H), 1.13 (s, 3H), 1.06 (s, 3H); $^{13}$C NMR ($CDCl_3$, 75 MHz) δ 205.02, 172.88, 172.48, 170.62, 170.45, 167.95, 166.98, 151.85, 140.77, 138.24, 133.86, 133.81, 132.35, 132.24, 130.35, 129.63, 129.15, 128.93, 128.85, 128.75, 128.44, 128.16, 127.29, 127.19, 85.50, 80.50, 78.27, 75.88, 75.76, 74.53, 73.28, 72.25, 55.30, 55.21, 53.15, 43.29, 40.90, 40.79, 35.87, 35.58, 26.33, 22.60, 21.69, 21.24, 21.05, 17.20, 14.66; LRMS (ESI): 928.5 ((M+1)$^+$, 100%).

The compounds of this invention exhibit antitumor activities in in vivo and/or in vitro models. For example, the following test describes the in vitro test used to evaluate some representative compounds of this invention.

Cytoxicity

The epoxide taxane derivatives possessed cytoxicity in vitro against human colon carcinoma cells HCT-116. Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," *Mol. Biol. Cell* 3 (Suppl.):184a, 1992. Cells were plated at 4,000 cell/well in 96 well microtiter plates and 24 hours later drugs were added and serial diluted. The cells were incubated at 37° for 72 hours at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an $IC_{50}$, which is the drug concentration required to inhibit cell proliferation (i.e. absorbance at 450 nM) to 50% of that of untreated control cells. The $IC_{50}$ values for compounds evaluated in this assay are evaluated in Table I.

TABLE I

| Compound | Cytotoxicity Assay $IC_{50}$ (nM) against HCT 116 Human colon tumor cell line[1] |
|---|---|
| 9 | 1.1 |
| 11 | 1.84 |
| 13 | 26.12 |
| 15 | 1.80 |
| 17 | 3.80 |
| 19 | 50.9 |
| 19a | >111 |
| 21 | >109 |
| 24 | 0.2 |
| 26 | 0.66 |
| 28 | 0.7 |
| 30 | 0.9 |
| 32 | 5.27 |
| 34 | 1.2 |
| 36 | 4.4 |
| 38 | 28.0 |
| 40 | 2.5 |
| 42 | 9.0 |
| 44 | 11.0 |

TABLE I-continued

| Compound | Cytotoxicity Assay $IC_{50}$ (nM) against HCT 116 Human colon tumor cell line[1] |
|---|---|
| 46 | 3.5 |
| 48 | 1.9 |
| 50 | 0.3 |
| 52 | 0.58 |
| 54 | 1.1 |
| 55 | >107.8 |

[1]Cytotoxicity was determined after a 72 h exposure by MTS assay.

The following results describes the in vivo tests used to evaluate representative compounds of this invention.

Mice M109 Model (In-Vivo)

Balb/c×DBA/2 $F_1$ hybrid mice were implanted intraperitoneally, as described by William Rose in Evaluation of Madison 109 Lung Carcinoma as a Model for Screening Antitumor Drugs, *Cancer Treatment Reports*, 65, No. 3–4 (1981), with 0.5 mL of a 2% (w/v) brei of M109 lung carcinoma.

Mice were treated with compounds under study by receiving intraperitoneal injections of various doses on days 5 and 8 post-implant. Mice were followed daily for survival until approximately 75 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e. % T/C) in the following Table II for representative compounds.

TABLE II

Paclitaxel & Derivatives vs ip M109

| Compd | O.D.[a] m/k/i | Deriv. Maximum % TC |
|---|---|---|
| 17 | 50 | 194 |
| 19 | 200 | 169 |
| 21 | 200 | 147 |
| 34 | 25 | 168 |
| 40 | 60 | 103 |
| 42 | 50 | 106 |
| 52 | 16 | 114 |
| 54 | 25 | 148 |
| 55 | 80 | 107 |

[a]Optimal dose (mg/kg/inj) if active, otherwise, maximal tolerated dose (MTD) or highest dose tested.

M5076: Taxane derivatives were tested in the M5076 murine sarcoma model using the general materials and methods described by Rose, W. C. in Anticancer Research 6: 557–562, 1986, for subcutaneous M5076 implants, with the following modifications: treatments were administered intravenously on Days 1, 3, 5, 7, and 9 post-tumor implant using eight mice per treatment and untreated control group. Activity was determined based on an increase in lifespan (as described in the preceding reference) of ≦135%, and, in particular, on a delay in tumor growth equivalent to at least 1 gross log cell kill (LCK). The latter was calculated as described in Rose, W. C. and Basler, G. A. in In Vivo 4: 391–396, 1990. The results are provided in Table III.

TABLE III

Paclitaxel & Derivatives vs Sc M5076

| Compd | O.D.[a] m/k/i | Deriv. Maximum T-C in LCK |
|---|---|---|
| 9 | 50 | 1.1 |
| 11 | 36 | 0.5 |
| 13 | 40 | 0.5 |
| 15 | 48 | 0.3 |
| 17 | 35 | 0.7 |
| 19 | 75 | 0.4 |
| 21 | 65 | 0 |
| 24 | 13 | 1.2 |
| 28 | 50 | 1.1 |
| 30 | 20 | 0.4 |
| 36 | 50 | 1.1 |
| 38 | 70 | 0 |
| 44 | 20 | 0 |
| 46 | 60 | 0 |
| 48 | 25 | 0.2 |
| 50 | 30 | 1.0 |

[a]Optimal dose (mg/kg/inj) if active, otherwise, maximal tolerated dose (MTD) or highest dose tested.

Thus, another aspect of the instant invention concerns a method for inhibiting human and/or other mammalian tumors which comprising administering to a tumor bearing host an antitumor effective amount of a compound of formula I.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 $mg/m^2$ over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof

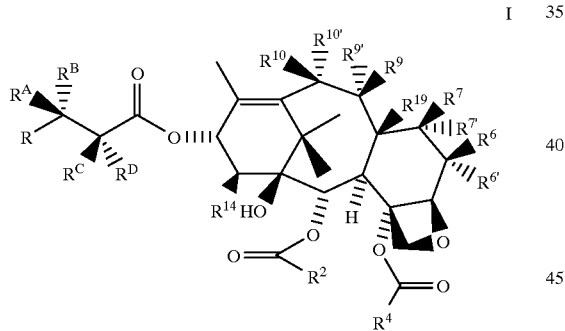

I wherein:

R is aryl, substituted aryl, $C_{1-6}$ alkyl, $C_{2-6}$ alkenyl, $C_{3-6}$ cycloalkyl, or heteroaryl;

$R^A$ is hydrogen;

$R^B$ is —NHC(O)-aryl, —NHC(O)-substituted aryl, —NHC(O)-heteroaryl, —NHC(O)OCH$_2$Ph, —NHC(O)O—($C_{1-6}$ alkyl), or —NHC(O)O—($C_{3-6}$ cycloalkyl);

$R^C$ is hydrogen;

$R^D$ is hydroxy, —OC(O)R$^x$, —OC(O)OR$^x$, OP(O)(OH)$_2$, OCH$_2$OP(O)(OH)$_2$, —OCH$_2$OCH$_2$OP(=O)(OH)$_2$, OP(O)(OH)$_2$ base, OCH$_2$OP(O)(OH)$_2$ base, —OCH$_2$OCH$_2$OP(=O)(OH)$_2$ base, —(OCH$_2$)$_m$OC=OCH$_2$NHR$^x$, —(OCH$_2$)$_m$OC(=O)CH(R'')NR'$_6$R'$_7$, —OCOCH$_2$CH$_2$NH$_3^+$HCOO$^-$, —OCOCH$_2$CH$_2$COOH, —OCO(CH$_2$)$_3$COOH, —OC(O)(CH$_2$)$_a$NR$^F$R$^G$, where a is 0–3, —OC(O)CH$_2$CH$_2$C(O)OCH$_2$CH$_2$OH or —OC(O)—Z—C(O)—R';

R$^x$ is $C_{1-6}$ alkyl, optionally substituted with one to six of the same or different halogen atoms, $C_{2-6}$ alkenyl or $C_{3-6}$ cycloalkyl;

Z is —CH$_2$CH$_2$—, —CH$_2$CH$_2$CH$_2$—, —CH=CH—, 1,2-cyclohexane or 1,2-phenylene;

R' is —OH, —OH base, —NR'$_2$R'$_3$, —OR'$_3$, —SR'$_3$, or —OCH$_2$C(O)NR'$_4$R'$_5$;

R'$_2$ is —H or —CH$_3$;

R'$_3$ is —(CH$_2$)$_j$NR'$_6$R'$_7$ or (CH$_2$)$_n$N$^+$R'$_6$R'$_7$R'8X$^-$, where j is 1–3;

R'$_4$ is —H or —C$_1$–C$_4$ alkyl;

R'$_5$ is —H, —C$_1$–C$_4$ alkyl, benzyl, hydroxyethyl, —CH$_2$CO$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X$^-$ is halide;

base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH;

R$^F$ and R$^G$ are independently —H or —C$_1$–C$_3$ alkyl, or R$^F$ and R$^G$ taken together with the nitrogen of NR$^F$R$^G$ form a pyrrolidino, piperidino, morpholino or N-methylpiperizino groups;

R'' is —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O)NHCH$_2$CH$_2$SO$_3$—Y+ or —OC(O)CH$_2$CH$_2$C(O)NHCH$_2$CH$_2$SO$_3$—Y+;

Y+ is Na+ or N+(Bu)$_4$;

R$^2$ is phenyl or substituted phenyl;

R$^4$ is $C_{1-4}$ alkyl, $C_{3-5}$ cycloalkyl or —O—($C_1$–C$_4$ alkyl);

L is O or S;

R$^6$ and R$^{6'}$ are independently hydrogen, —SH, —S—[$C_{1-6}$ alkyl(OH)$_m$], —S—ethenyl, —S-substituted ethenyl, —S(O)$_n$CH$_2$CN, —S(O)$_n$CH$_2$C(O)Q, —SCH$_2$ halogen, —SC(O)—($C_{1-6}$ alkyl(OH)$_m$), —SC(O)O($C_1$–C$_6$ alkyl), —SC(O)N(W)$_2$, —SC(S)—($C_1$–C$_6$ alkyl), —SC(S)O($C_1$–C$_6$ alkyl), —SC(S)N(W)$_2$, —S(O)$_n$—($C_{1-6}$ alkyl(OH)$_m$), —S(C$_1$–C$_6$ alkyl)$_2^{+X-}$, —S(O)$_2$OH, —S(O)$_2$NH($C_{1-6}$ alkyl(OH)$_m$), —S(O)$_2$N($C_{1-6}$ alkyl(OH)$_m$)$_2$, —S—S—($C_{1-6}$ alkyl(OH)$_m$), —S—S-substituted phenyl, —S(O)—CN, —S(O)$_2$—CN, —SCH$_2$O($C_{1-6}$ alkyl(OH)$_m$), —SCH($C_1$–C$_6$ alkyl)O($C_{1-6}$ alkyl(OH)$_m$), —SCH$_2$OCH$_2$OCH$_3$, —SCH$_2$S($C_{1-6}$ alkyl(OH)$_m$), —SCH$_2$S(O)($C_{1-6}$ alkyl(OH)$_m$), —SCH$_2$S(O)$_2$($C_{1-6}$ alkyl(OH)$_m$), —S-heteroaryl or —SCN; provided R$^6$ and R$^{6'}$ are not both hydrogen at the same time;

m is 0, 1, 2 or 3;

n is 0, 1, or 2;

S-substituted ethenyl is —S—C(R$^H$)=C(R$^J$)(R$^K$), wherein two of R$^H$, R$^J$ and R$^K$ are each H and the other of R$^H$, R$^J$ and R$^K$ is $C_{1-3}$ alkyl, CN, COOC$_{1-3}$ alkyl, S(O)$_2$CH$_3$ or C(O)CH$_3$;

W is H or $C_{1-6}$ alkyl;

Q is —($C_{1-6}$ alkyl(OH)$_m$), —O($C_{1-6}$ alkyl), —OCH$_2$CCl$_3$, —N(W)$_2$ or —C(O)OH;

R$^{7'}$ is hydrogen;

R$^7$ is hydrogen, hydroxy or when taken together with R$^{19}$ forms a cyclopropane ring;

$R^9$ and $R^{9'}$ are independently hydrogen or hydroxy or $R^9$ and $R^{9'}$ together form an oxo (keto) group;

$R^{10}$ is hydrogen, hydroxy or —OC(O)—($C_1$–$C_6$ alkyl);

$R^{10'}$ is hydrogen;

$R^{14}$ is hydrogen or hydroxy; and $R^{19}$ is methyl or when taken together with $R^7$ forms a cyclopropane ring.

2. A compound of claim 1 or a pharmaceutically acceptable salt thereof wherein:

R is phenyl, p-fluorophenyl, p-chlorophenyl, p-hydroxyphenyl, p-tolyl, isopropyl, isopropenyl, isobutenyl, isobutyl, cyclopropyl, furyl, or thienyl;

$R^2$ is phenyl;

L is O;

$R^{6'}$ is hydrogen;

$R^6$ is —SH, —S—($C_{1-6}$ alkyl$(OH)_m$), —S-ethenyl, —S-substituted ethenyl, —S(O)$_n$CH$_2$CN, —S(O)$_n$CH$_2$C(O)Q, —SCH$_2$ halogen, —SC(O)—($C_{1-6}$ alkyl$(OH)_m$), —SC(O)O($C_1$–$C_6$ alkyl), —SC(O)N(W)$_2$, —SC(S)—($C_1$–$C_6$ alkyl), —SC(S)O($C_{1-6}$ alkyl), —SC(S)N(W)$_2$, —S(O)$_n$-($C_{1-6}$ alkyl$(OH)_m$), —S($C_1$–$C_6$ alkyl)$_2$$^{+X^-}$, —S(O)$_2$OH, —S(O)$_2$NH($C_{1-6}$ alkyl$(OH)_m$), —S(O)$_2$N($C_{1-6}$ alkyl$(OH)_m$)$_2$, —S—S—($C_{1-6}$ alkyl$(OH)_m$), —S—S-substituted phenyl, —S(O)—CN, —S(O)$_2$—CN, —SCH$_2$O($C_{1-6}$ alkyl$(OH)_m$), —SCH($C_1$–$C_6$ alkyl)O($C_{1-6}$ alkyl$(OH)_m$), —SCH$_2$OCH$_2$OCH$_3$, —SCH$_2$S($C_{1-6}$ alkyl$(OH)_m$), —SCH$_2$S(O) ($C_{1-6}$ alkyl$(OH)_m$), —SCH$_2$S(O)$_2$($C_{1-6}$ alkyl$(OH)_m$), —S-heteroaryl or —SCN;

m is 0, 1, 2 or 3;

n is 0, 1, or 2;

W is H or $C_{1-6}$ alkyl;

$R^9$ and $R^{9'}$ together form an oxo (keto) group;

$R^{10}$ is hydroxy or —OC(O)CH$_3$; and $R^{14}$ is hydrogen.

3. A compound of claim 2 or pharmaceutically acceptable salts there of wherein:

$R^6$ is —SH, —S—($C_{1-6}$ alkyl$(OH)_m$), —S(O)$_n$—($C_{1-6}$ alkyl$(OH)_m$), —S-ethenyl, —S-substituted ethenyl, —SCH$_2$CN, —S(O)CH$_2$CN, —SCH$_2$C(O)Q, —SC(O)—($C_{1-6}$ alkyl$(OH)_m$), —SCH$_2$O($C_{1-6}$ alkyl$(OH)_m$), —SCH($C_1$–$C_6$ alkyl)O($C_{1-6}$ alkyl$(OH)_m$), —SCH$_2$OCH$_2$OCH$_3$, —SCH$_2$S($C_{1-6}$ alkyl$(OH)_m$), —SCH$_2$S(O)($C_{1-6}$ alkyl$(OH)_m$), —SCH$_2$S(O)$_2$($C_{1-6}$ alkyl$(OH)_m$), or —SCN.

4. A compound of claim 3 or pharmaceutically acceptable salts thereof wherein:

$R^B$ is —NHC(O)—Ph or —NHC(O)O—($C_{1-6}$ alkyl);

$R^D$ is hydroxy;

$R^4$ is methyl;

$R^6$ is —S—($C_{1-6}$ alkyl$(OH)_m$), —S-ethenyl, —S-substituted ethenyl, —SCH$_2$CN, —S(O)CH$_2$CN, —SCH$_2$C(O)Q, —S(O)($C_{1-6}$ alkyl), —SC(O)—($C_{1-6}$ alkyl$(OH)_m$), —SCH$_2$OCH$_3$, —SCH$_2$OCH$_2$OCH$_3$, —SCH$_2$S($C_{1-6}$ alkyl), —SCH$_2$S(O)($C_{1-6}$ alkyl), or —SCN; and $R^7$ is hydrogen or when taken together with $R^{19}$ forms a cyclopropane ring.

5. A compound of claim 4 or pharmaceutically acceptable salts thereof wherein:

$R^7$ is hydrogen; and $R^{19}$ is methyl.

6. A compound of claim 5 or pharmaceutically acceptable salts thereof wherein:

R is phenyl;

$R^6$ is —S-methyl, —S-ethyl, —S-ethenyl, —SCH$_2$CN, —S(O)CH$_2$CN, —SCH$_2$C(O)—($C_{1-6}$ alkyl), —S(O)—($C_{1-6}$ alkyl), —SC(O)—($C_{1-6}$ alkyl$(OH)_m$), —SCH$_2$OCH$_3$, —SCH$_2$OCH$_2$OCH$_3$, —SCH$_2$SCH$_3$, —SCH$_2$S(O)(CH$_3$), or —SCN; and $R^{10}$ is —OC(O)CH$_3$.

7. A compound of claim 1, wherein:

R is phenyl or substituted phenyl;

$R^A$ is hydrogen;

$R^B$ is —NHC(O)Ph or —NHC(O)O($C_{1-6}$ alkyl);

$R^C$ is hydrogen;

$R^D$ is hydroxy;

$R^2$ is phenyl;

$R^4$ is methyl;

L is O;

$R^{6'}$ is hydrogen;

$R^6$ is —SH, —S($C_{1-3}$ alkyl), —SCN, —S-ethenyl, —SCH$_2$CN, —SCH$_2$CH$_2$OH, —SCH$_2$(O)—($C_{1-6}$ alkyl $(OH)_m$) or —S—(2-thienyl);

$R^{7'}$ and $R^7$ are each hydrogen;

$R^9$ and $R^{9'}$ together form an oxo (keto) group;

$R^{10}$ is —OC(O)CH$_3$ or OH;

$R^{10'}$ is hydrogen;

$R^{14}$ is hydrogen; and $R^{19}$ is methyl.

8. A compound of claim 7 wherein:

R is phenyl, p-chlorophenyl, p-methylphenyl, p-fluorophenyl or p-hydroxyphenyl.

9. A pharmaceutical formulation which comprises an antitumor effective amount of a compound of formula I as claimed in any one of claims 1–8.

10. A method for inhibiting tumor growth in a mammalian host which comprises administering to said mammal a tumor-growth inhibiting amount of a compound of formula I as claimed in any one of claims 1–8.

* * * * *